US012060435B2

United States Patent
Williams et al.

(10) Patent No.: US 12,060,435 B2
(45) Date of Patent: Aug. 13, 2024

(54) MULTI-SPECIFIC LIGAND BINDERS

(71) Applicant: CITY OF HOPE, Duarte, CA (US)

(72) Inventors: John C. Williams, Monrovia, CA (US); Jeremy King, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 475 days.

(21) Appl. No.: 16/959,981

(22) PCT Filed: Jan. 7, 2019

(86) PCT No.: PCT/US2019/012584
§ 371 (c)(1),
(2) Date: Jul. 2, 2020

(87) PCT Pub. No.: WO2019/136405
PCT Pub. Date: Jul. 11, 2019

(65) Prior Publication Data
US 2021/0061922 A1    Mar. 4, 2021

Related U.S. Application Data

(60) Provisional application No. 62/731,781, filed on Sep. 14, 2018, provisional application No. 62/614,267, filed on Jan. 5, 2018.

(51) Int. Cl.
*C07K 16/18* (2006.01)
*A61K 47/65* (2017.01)
(Continued)

(52) U.S. Cl.
CPC .............. *C07K 16/32* (2013.01); *A61K 47/65* (2017.08); *A61P 35/00* (2018.01);
(Continued)

(58) Field of Classification Search
None
See application file for complete search history.

(56) References Cited

U.S. PATENT DOCUMENTS 8,987,417 B2   3/2015 Zwaagstra et al.
9,951,145 B2   4/2018 Kim et al.
(Continued)

FOREIGN PATENT DOCUMENTS

CN       104955953 A    9/2015
WO    WO-2016/202457 A1   12/2016
(Continued)

OTHER PUBLICATIONS

Chan et al., Therapeutic antibodies for autoimmunity and inflammation, Nat. Rev. Immunol. 10:301-316, May 2010.*
(Continued)

*Primary Examiner* — Claire Kaufman
(74) *Attorney, Agent, or Firm* — Mintz Levin Cohn Ferris Glovsky and Popeo PC

(57) ABSTRACT

Provided herein are, inter alia, novel peptide compositions having multi-specific binding capabilities useful for therapeutic and diagnostic purposes. The peptide compositions provided herein are polypeptide conjugates including at least two ligand binding domains able to target (bind) two or more ligands (e.g., antigens) at the same time. The peptide compositions provided herein can be produced at very high yields and are therefore easy to manufacture.

10 Claims, 21 Drawing Sheets

Specification includes a Sequence Listing.

(51) Int. Cl.
| | |
|---|---|
| *A61P 35/00* | (2006.01) |
| *C07K 16/28* | (2006.01) |
| *C07K 16/30* | (2006.01) |
| *C07K 16/32* | (2006.01) |
| *C12N 5/0783* | (2010.01) |

(52) U.S. Cl.
CPC ...... *C07K 16/2803* (2013.01); *C07K 16/2809* (2013.01); *C07K 16/283* (2013.01); *C07K 16/2866* (2013.01); *C07K 16/2875* (2013.01); *C07K 16/2878* (2013.01); *C07K 16/2887* (2013.01); *C07K 16/3092* (2013.01); *C12N 5/0636* (2013.01); *C07K 2317/31* (2013.01); *C07K 2317/51* (2013.01); *C07K 2317/515* (2013.01); *C07K 2317/52* (2013.01); *C07K 2317/524* (2013.01); *C07K 2317/526* (2013.01); *C07K 2317/55* (2013.01); *C07K 2317/569* (2013.01); *C07K 2317/64* (2013.01)

(56) References Cited

U.S. PATENT DOCUMENTS

| | | | |
|---|---|---|---|
| 11,285,207 | B2 * | 3/2022 | Codarri Deak ......... A61P 35/00 |
| 2010/0189727 | A1 | 7/2010 | Rodeck et al. |
| 2014/0127210 | A1 * | 5/2014 | Kim .................. A61P 43/00 |
| | | | 435/69.6 |
| 2015/0045540 | A1 | 2/2015 | Howowitz et al. |
| 2015/0284463 | A1 | 10/2015 | Tamaskovic et al. |
| 2016/0145354 | A1 * | 5/2016 | Bacac .................... C07K 16/32 |
| | | | 435/254.2 |
| 2017/0313759 | A1 | 11/2017 | Batuwangala et al. |
| 2019/0233519 | A1 * | 8/2019 | Zhang ................ A61K 39/3955 |
| 2019/0389971 | A1 * | 12/2019 | Dengl .................... C07K 16/00 |

FOREIGN PATENT DOCUMENTS

| | | |
|---|---|---|
| WO | WO-2017/191101 A1 | 11/2017 |
| WO | WO-2019/086395 A1 | 5/2019 |
| WO | WO-2019/086499 A1 | 5/2019 |
| WO | WO-2019/086500 A2 | 5/2019 |
| WO | WO-2019/086500 A3 | 5/2019 |

OTHER PUBLICATIONS

InvivoGen, Cartalog and Data Sheet for: pFUSE-hIgG1e5-Fc_Cloning vector with emgineered human IgG1 heavy chain constant region , Retrieved online: <URL:https://www.invivogen.com/pfuse-higg1e5-fc>, Retreived on Aug. 29, 2022.*

Qasemi et al., Construction and expression of an anti-VEGFR2 Nanobody-Fc fusionbody in NS0 host cell, Prot. Express. Purif. 123: 19-25, Mar. 2016.*

Onuoha et al., Rational Design of Antirheumatic Prodrugs Specific for Sites of Inflammation, Arth. Rheumatol. 67(10), 2661-2672, 2015.*

Brinkmann et al., The making of bispecific antibodies, MAbs., Feb.-Mar.; 9(2): 182-212, 2017.*

Dimasi et al., Guiding bispecific monovalent antibody formation through proteolysis of IgG1 single-chain, Mabs, 9(3): 438-454, Apr. 2017.*

Li et al., A single-domain antibody-linked Fab bispecific antibody Her2-S-Fab has potent cytotoxicity against Her2-expressing tumor cells, AMB Expr. 6:32, 8 pages, 2016.*

Georges, G.Y. et al. (May 14, 2020). "The Contorsbody, an antibody format for agonism: Design, structure, and function," *Comput Struct Biotechnol J.* 18:1210-1220.

International Search Report mailed on Apr. 8, 2019, for PCT Application No. PCT/US2019/012584, filed Jan. 7, 2019, 3 pages.

Moek, K.L. et al. (Sep. 2017). "Theranostics Using Antibodies and Antibody-Related Therapeutics," *J Nucl Med* 58(Suppl 2):83S-90S.

Written Opinion mailed on Apr. 8, 2019, for PCT Application No. PCT/US2019/012584, filed Jan. 7, 2019, 14 pages.

Wu, A.M. (Jan. 1, 2014, e-published Oct. 1, 2013). "Engineered antibodies for molecular imaging of cancer," *Methods* 65(1):139-147.

Kontermann, R.E. (Mar./Apr. 2012, e-published Mar. 1, 2012). "Dual targeting strategies with bispecific antibodies," *mAbs* 4(2):182-197.

Tuscano, J.M. et al. (Jun. 2011, e-published Feb. 24, 2011). "The Bs20x22 anti-CD20-CD22 bispecific antibody has more lymphomacidal activity than do the parent antibodies alone," *Cancer Immunol Immunother* 60(6):771-780.

Stamova, S. et al. (Dec. 2011, e-published Oct. 19, 2011). "Unexpected recombinations in single chain bispecific anti-CD3-anti-CD33 antibodies can be avoided by a novel linker module," *Molecular Immunology* 49(3):474-482.

* cited by examiner

Meditope-Fluorescein conjugated to αCD33-αCD123-αCD20

SEQUENCE LISTING

<160> NUMBER OF SEQ ID NOS: 74

<210> SEQ ID NO 1
<211> LENGTH: 583

```
<212> TYPE: PRT
<213> ORGANISM: Artificial sequence
<220> FEATURE:
<223> OTHER INFORMATION: Synthetic polypeptide

<400> SEQUENCE: 1
```

| | | | | | | | | | | | | | | |
|---|---|---|---|---|---|---|---|---|---|---|---|---|---|---|
| Asp | Ile | Gln | Met | Thr | Gln | Ser | Pro | Ile | Leu | Leu | Ser | Ala | Ser | Val | Gly |
| 1 | | | | 5 | | | | | 10 | | | | | 15 | |

| Asp | Arg | Val | Thr | Ile | Thr | Cys | Arg | Ala | Ser | Gln | Asp | Val | Asn | Thr | Ala |
|---|---|---|---|---|---|---|---|---|---|---|---|---|---|---|---|
| | | | 20 | | | | | 25 | | | | | 30 | | |

| Val | Ala | Trp | Tyr | Gln | Gln | Arg | Thr | Asn | Gly | Ser | Pro | Arg | Leu | Leu | Ile |
|---|---|---|---|---|---|---|---|---|---|---|---|---|---|---|---|
| | | 35 | | | | | 40 | | | | | 45 | | | |

| Tyr | Ser | Ala | Ser | Phe | Leu | Tyr | Ser | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Arg | Ser | Gly | Thr | Asp | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Glu | Asp | Ile | Ala | Asp | Tyr | Tyr | Cys | Gln | Gln | His | Tyr | Thr | Thr | Pro | Pro |
|---|---|---|---|---|---|---|---|---|---|---|---|---|---|---|---|
| | | | 85 | | | | | 90 | | | | | 95 | | |

| Thr | Phe | Gly | Ala | Gly | Thr | Lys | Val | Glu | Ile | Lys | Arg | Thr | Val | Ala | Ala |
|---|---|---|---|---|---|---|---|---|---|---|---|---|---|---|---|
| | | 100 | | | | | 105 | | | | | 110 | | | |

| Pro | Ser | Val | Phe | Ile | Phe | Pro | Pro | Ser | Asp | Glu | Gln | Leu | Lys | Ser | Gly |
|---|---|---|---|---|---|---|---|---|---|---|---|---|---|---|---|
| | 115 | | | | | 120 | | | | | 125 | | | | |

| Thr | Ala | Ser | Val | Val | Cys | Leu | Leu | Asn | Asn | Phe | Tyr | Pro | Arg | Glu | Ala |
|---|---|---|---|---|---|---|---|---|---|---|---|---|---|---|---|
| 130 | | | | | 135 | | | | | 140 | | | | | |

| Lys | Val | Gln | Trp | Lys | Val | Asp | Asn | Ala | Leu | Gln | Ser | Gly | Asn | Ser | Gln |
|---|---|---|---|---|---|---|---|---|---|---|---|---|---|---|---|
| 145 | | | | | 150 | | | | | 155 | | | | | 160 |

| Glu | Ser | Val | Thr | Glu | Gln | Asp | Ser | Lys | Asp | Ser | Thr | Tyr | Ser | Leu | Ser |
|---|---|---|---|---|---|---|---|---|---|---|---|---|---|---|---|
| | | | 165 | | | | | 170 | | | | | 175 | | |

| Ser | Thr | Leu | Thr | Leu | Ser | Lys | Ala | Asp | Tyr | Glu | Lys | His | Lys | Val | Tyr |
|---|---|---|---|---|---|---|---|---|---|---|---|---|---|---|---|
| | | 180 | | | | | 185 | | | | | 190 | | | |

| Ala | Cys | Glu | Val | Thr | His | Gln | Gly | Leu | Ser | Ser | Pro | Val | Thr | Lys | Ser |
|---|---|---|---|---|---|---|---|---|---|---|---|---|---|---|---|
| | 195 | | | | | 200 | | | | | 205 | | | | |

| Phe | Asn | Arg | Gly | Glu | Cys | Gly | Gly | Ala | Gly | Gly | Ser | Thr | Ser | Thr | Ser |
|---|---|---|---|---|---|---|---|---|---|---|---|---|---|---|---|
| 210 | | | | | 215 | | | | | 220 | | | | | |

| Gly | Arg | Ser | Ala | Asn | Pro | Arg | Gly | Gly | Glu | Val | Gln | Leu | Thr | Glu | Ser |
|---|---|---|---|---|---|---|---|---|---|---|---|---|---|---|---|
| 225 | | | | | 230 | | | | | 235 | | | | | 240 |

| Gly | Gly | Glu | Asp | Val | Gln | Ala | Gly | Gly | Ser | Leu | Arg | Leu | Ser | Cys | Ser |
|---|---|---|---|---|---|---|---|---|---|---|---|---|---|---|---|
| | | | 245 | | | | | 250 | | | | | 255 | | |

| Ala | Ser | Gly | Leu | Thr | Phe | Ser | Ser | Tyr | Asn | Met | Gly | Trp | Phe | Arg | Arg |
|---|---|---|---|---|---|---|---|---|---|---|---|---|---|---|---|
| | | 260 | | | | | 265 | | | | | 270 | | | |

| Ala | Pro | Gly | Lys | Glu | Arg | Glu | Phe | Val | Ala | Ser | Ile | Thr | Trp | Ser | Gly |
|---|---|---|---|---|---|---|---|---|---|---|---|---|---|---|---|
| | 275 | | | | | 280 | | | | | 285 | | | | |

| Arg | Asp | Thr | Phe | Tyr | Ala | Asp | Ser | Val | Lys | Gly | Arg | Phe | Thr | Ile | Ser |
|---|---|---|---|---|---|---|---|---|---|---|---|---|---|---|---|
| 290 | | | | | 295 | | | | | 300 | | | | | |

| Arg | Asp | Asn | Ala | Lys | Asn | Thr | Val | Tyr | Leu | Gln | Met | Ser | Ser | Leu | Lys |
|---|---|---|---|---|---|---|---|---|---|---|---|---|---|---|---|
| 305 | | | | | 310 | | | | | 315 | | | | | 320 |

| Pro | Glu | Asp | Thr | Ala | Thr | Tyr | Tyr | Cys | Ala | Ala | Asn | Pro | Trp | Pro | Val |
|---|---|---|---|---|---|---|---|---|---|---|---|---|---|---|---|
| | | | 325 | | | | | 330 | | | | | 335 | | |

| Ala | Ala | Pro | Arg | Ser | Gly | Thr | Tyr | Trp | Gly | Glu | Gly | Thr | Gln | Val | Thr |
|---|---|---|---|---|---|---|---|---|---|---|---|---|---|---|---|
| | | 340 | | | | | 345 | | | | | 350 | | | |

| Val | Ala | Ser | Gly | Ala | Gly | Ala | Ser | Glu | Val | Gln | Leu | Val | Glu | Ser | Gly |
|---|---|---|---|---|---|---|---|---|---|---|---|---|---|---|---|
| | 355 | | | | | 360 | | | | | 365 | | | | |

| Gly | Gly | Leu | Val | Gln | Pro | Gly | Gly | Ser | Leu | Arg | Leu | Ser | Cys | Ala | Ala |
|---|---|---|---|---|---|---|---|---|---|---|---|---|---|---|---|
| | 370 | | | | | 375 | | | | | 380 | | | | |

```
Ser Gly Phe Asn Ile Lys Asp Thr Tyr Ile His Trp Val Arg Gln Ser
385                 390                 395                 400

Pro Gly Lys Gly Leu Glu Trp Val Ala Arg Ile Tyr Pro Thr Asn Gly
            405                 410                 415

Tyr Thr Arg Tyr Ala Asp Ser Val Lys Gly Arg Phe Thr Ile Ser Ala
            420                 425                 430

Asp Thr Ser Lys Asn Thr Ala Tyr Leu Gln Met Asn Ser Leu Arg Ala
            435                 440                 445

Glu Asp Thr Ala Ile Tyr Tyr Cys Ser Arg Trp Gly Gly Asp Gly Phe
    450                 455                 460

Tyr Ala Met Asp Tyr Trp Gly Gln Gly Thr Leu Val Thr Val Ser Ser
465                 470                 475                 480

Ala Ser Thr Lys Gly Pro Ser Val Phe Pro Leu Ala Pro Ser Ser Lys
            485                 490                 495

Ser Thr Ser Gly Gly Thr Ala Ala Leu Gly Cys Leu Val Lys Asp Tyr
            500                 505                 510

Phe Pro Glu Pro Val Thr Val Ser Trp Asn Ser Gly Ala Leu Thr Ser
    515                 520                 525

Gly Val His Thr Phe Pro Ala Val Leu Gln Ser Ser Gly Leu Tyr Ser
    530                 535                 540

Leu Ser Ser Val Val Thr Val Pro Ser Ser Ser Leu Gly Thr Gln Thr
545                 550                 555                 560

Tyr Ile Cys Asn Val Asn His Lys Pro Ser Asn Thr Lys Val Asp Lys
            565                 570                 575

Lys Val Glu Pro Lys Ser Cys
            580

<210> SEQ ID NO 2
<211> LENGTH: 691
<212> TYPE: PRT
<213> ORGANISM: Artificial sequence
<220> FEATURE:
<223> OTHER INFORMATION: Synthetic polypeptide

<400> SEQUENCE: 2

Asp Ile Gln Met Thr Gln Ser Pro Ser Ile Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Arg Thr Asn Lys Ala Pro
        35                  40                  45

Arg Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Asp Asp Glu Ala Asp Tyr Tyr Cys Gln Gln Ser Lys
            85                  90                  95

Glu Val Pro Trp Thr Phe Gly Ala Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160
```

```
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Gly Gly Ser Ser Gly Glu
    210                 215                 220
Val Gln Leu Val Glu Ser Gly Gly Gly Leu Val Gln Ala Gly Gly Ser
225                 230                 235                 240
Leu Arg Leu Ser Cys Ala Ala Ser Gly Ser Ile Phe Ser Gly Asn Val
                245                 250                 255
Met Gly Trp Tyr Arg Gln Ala Pro Gly Lys Glu Arg Glu Trp Val
            260                 265                 270
Ala Ala Ile Ala Ser Gly Gly Ser Ile Tyr Tyr Arg Asp Ser Val Lys
        275                 280                 285
Gly Arg Phe Thr Ile Ser Arg Asp Asn Ala Lys Asn Thr Val Tyr Leu
    290                 295                 300
Gln Met Asn Ser Leu Lys Pro Glu Asp Thr Ala Val Tyr Tyr Cys Asn
305                 310                 315                 320
Ser His Pro Pro Thr Leu Pro Tyr Trp Gly Leu Gly Thr Gln Val Thr
                325                 330                 335
Val Ser Ser Gly Ser Glu Val Gln Leu Val Glu Ser Gly Gly Gly Leu
            340                 345                 350
Val Gln Pro Gly Gly Ser Leu Arg Leu Ser Cys Thr Phe Ser Gly Gly
        355                 360                 365
Thr Phe Ser Ser Tyr Thr Met Gly Trp Phe Arg Gln Ala Pro Gly Lys
    370                 375                 380
Glu Arg Glu Phe Val Ala Glu Val Arg Trp Gly Val Thr Thr Tyr
385                 390                 395                 400
Ser Asn Ser Leu Lys Asp Arg Phe Ser Ile Ser Glu Asp Ser Val Lys
                405                 410                 415
Asn Ala Val Tyr Leu Gln Met Asn Ser Leu Lys Pro Glu Asp Thr Ala
            420                 425                 430
Val Tyr Tyr Cys Ala Ala Val Arg Gln Met Tyr Met Thr Val Val Pro
        435                 440                 445
Asp Tyr Trp Gly Gln Gly Thr Leu Val Thr Val Ser Ser Gly Gly Gly
    450                 455                 460
Ser Ser Gly Glu Val Gln Leu Val Gln Ser Gly Ala Glu Val Lys Lys
465                 470                 475                 480
Pro Gly Ser Ser Val Lys Val Ser Cys Lys Ala Ser Gly Tyr Thr Phe
                485                 490                 495
Thr Asp Tyr Asn Met His Trp Val Arg Gln Ser Pro Gly Gln Gly Leu
            500                 505                 510
Glu Trp Ile Gly Tyr Ile Tyr Pro Tyr Asn Gly Gly Thr Gly Tyr Asn
        515                 520                 525
Gln Lys Phe Lys Ser Lys Ala Thr Ile Thr Ala Asp Glu Ser Thr Asn
    530                 535                 540
Thr Ala Tyr Met Glu Leu Ser Ser Leu Arg Ser Glu Asp Thr Ala Ile
545                 550                 555                 560
Tyr Tyr Cys Ala Arg Gly Arg Pro Ala Met Asp Tyr Trp Gly Gln Gly
                565                 570                 575
Thr Leu Val Thr Val Ser Ser Ala Ser Thr Lys Gly Pro Ser Val Phe
```

|      |      | 580  |      |      |      | 585  |      |      |      | 590  |      |      |
|------|------|------|------|------|------|------|------|------|------|------|------|------|
| Pro  | Leu  | Ala  | Pro  | Ser  | Ser  | Lys  | Ser  | Thr  | Ser  | Gly  | Gly  | Thr  | Ala | Ala | Leu |

Pro Leu Ala Pro Ser Ser Lys Ser Thr Ser Gly Gly Thr Ala Ala Leu
                                595                             600                         605

Gly Cys Leu Val Lys Asp Tyr Phe Pro Glu Pro Val Thr Val Ser Trp
    610                     615                     620

Asn Ser Gly Ala Leu Thr Ser Gly Val His Thr Phe Pro Cys Val Leu
625                 630                 635                 640

Gln Ser Ser Gly Leu Tyr Ser Leu Ser Ser Val Val Thr Val Pro Ser
            645                 650                 655

Ser Ser Leu Gly Thr Gln Thr Tyr Ile Cys Asn Val Asn His Lys Pro
            660                 665                 670

Ser Asn Thr Lys Val Asp Lys Lys Val Glu Pro Lys Ser Gly Asp Lys
        675                 680                 685

Thr His Thr
    690

<210> SEQ ID NO 3
<211> LENGTH: 2133
<212> TYPE: DNA
<213> ORGANISM: Artificial sequence
<220> FEATURE:
<223> OTHER INFORMATION: Synthetic polynucleotide

<400> SEQUENCE: 3

```
atggacatga gggtccccgc tcagctcctg gggctcctgc tgctctggct cccaggtgcc    60
aaatgtgata tccagatgac ccagtcgcct tcaatcctgt cggcatccgt cggagacaga   120
gtgaccatca cttgccgggc cagcgaatcc gtggataact acggaatttc cttcatgaat   180
tggttccagc agcggaccaa caaggccccg cgcctgctga tctacgcggc cagcaaccaa   240
gggtccggag tgccttcacg gttctccggc tccgggtccg gcaccgactt cacccttgacc   300
atttcctccc tgcaaccgga cgacgaagcc gattactact gccagcagtc caaggaagtg   360
ccgtggacct tcggagcggg aaccaagctc gagattaagc ggaccgtggc agcaccatca   420
gtgtttattt tccccccgtc cgacgagcag ctgaagtcgg gtactgcgag cgtggtctgc   480
ctgctgaaca atttctatcc gcgggaggcc aaggtccagt ggaaagtcga caacgccctc   540
cagagcggaa actctcagga gagcgtgacc gaacaggact ccaaggacag cacctactcg   600
ctgtcctcca cgctcactct gtccaaggcc gattacgaga agcacaaggt ctacgcatgc   660
gaagtgaccc accagggtct ttcctcccct gtgactaagt cgttcaatcg cggggaggga   720
gggggatcct cgggagaagt gcagcttgtg gagagcggcg gaggattggt gcaggccggg   780
ggatccctga ctgtcctg tgccgcgagc ggctcgatct tctccggaaa cgtgatgggc   840
tggtaccggc agaggcacc gggaaaggaa agggaatggg tggccgccat cgcctcggga   900
ggcagcatct actaccggga ttctgtgaag ggacggttca ccatctcccg ggataacgcc   960
aagaacactg tgtacctcca gatgaactca ctcaagccag aggataccgc ggtctattac  1020
tgcaattccc accctcccac cctgccctac tgggggcttg gtacccaagt caccgtgtcc  1080
tcgggctccg aggtgcaact ggtggaatct gggggcggcc tggtccagcc tggcggctcc  1140
ttgcggctgt catgcacatt cagcggtgga accttcagct cctacaccat gggctggttc  1200
cgccaagcgc aggaaagga cgggagttc gtggccgaag tgcgctgggg cggagtgact  1260
acctactcga actccctgaa agaccggttc agcatttccg aggacagcgt gaagaacgcc  1320
gtgtacttgc aaatgaactc ccttaagcct gaggacactg ctgtgtatta ctgtgccgcc  1380
```

-continued

```
gtgcgccaga tgtacatgac cgtggtgccg gactattggg gccagggcac cctggtcacc      1440
gtcagctcgg gcggcggaag ctccggagag gtccagctgg tgcagtcggg agccgaagtg      1500
aagaagcccg gctcgtccgt gaaagtgtcc tgcaaggcct cgggctacac ctttaccgac      1560
tacaatatgc attgggtcag acaatcaccg gccagggac tcgaatggat tggctacatc       1620 taccccctaca acggtggaac tggctacaac caaaagttta agtctaaggc tactattacc     1680
gccgacgaaa gcactaacac cgcctacatg aactgagct ccctgagatc cgaggacacc       1740
gcgatctact actgtgcccg cgggcgccct gcgatggact actggggcca aggcactctc     1800
gtgactgtgt catcggcgtc aactaaggga ccgagcgtct ttccgctggc acccagctcc      1860
aagtccactt ccggtggcac ggccgctctc ggttgcctcg tgaaggatta cttccctgaa     1920
cccgtgaccg tgtcctggaa ctccggagcg ctgacctccg gagtgcacac tttcccctgc     1980
gtgcttcaaa gctccgggct gtactccctg agctcggtcg tgaccgtgcc ctcatcctcg     2040
ttgggtactc agacgtacat ctgcaacgtg aaccacaagc cgtcgaatac caaggtcgac     2100
aagaaggtcg aacccaaatc gggagataag taa                                  2133
```

<210> SEQ ID NO 4
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 4

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

-continued

```
<210> SEQ ID NO 5
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 5

Gly Gly Ala Gly Gly Ser Thr Ser Thr Ser Gly Arg Ser Ala Asn Pro
1               5                   10                  15

Arg Gly Gly

<210> SEQ ID NO 6
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 6

Glu Val Gln Leu Thr Glu Ser Gly Gly Glu Asp Val Gln Ala Gly Gly
1               5                   10                  15

Ser Leu Arg Leu Ser Cys Ser Ala Ser Gly Leu Thr Phe Ser Ser Tyr
            20                  25                  30

Asn Met Gly Trp Phe Arg Arg Ala Pro Gly Lys Glu Arg Glu Phe Val
        35                  40                  45

Ala Ser Ile Thr Trp Ser Gly Arg Asp Thr Phe Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Glu Asp Thr Ala Thr Tyr Tyr Cys
                85                  90                  95

Ala Ala Asn Pro Trp Pro Val Ala Ala Pro Arg Ser Gly Thr Tyr Trp
            100                 105                 110

Gly Glu Gly Thr Gln Val Thr Val
        115                 120

<210> SEQ ID NO 7
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 7

Ala Ser Gly Ala Gly Ala Ser
1               5

<210> SEQ ID NO 8
<211> LENGTH: 223
<212> TYPE: PRT
<213> ORGANISM: Artificial sequence
<220> FEATURE:
<223> OTHER INFORMATION: Synthetic polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ser Pro Gly Lys Gly Leu Glu Trp Val
        35                  40                  45
```

```
Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Ile Tyr Tyr Cys
                 85                  90                  95

Ser Arg Trp Gly Gly Asp Gly Phe Tyr Ala Met Asp Tyr Trp Gly Gln
             100                 105                 110

Gly Thr Leu Val Thr Val Ser Ser Ala Ser Thr Lys Gly Pro Ser Val
             115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
                 180                 185                 190

Ser Ser Leu Gly Thr Gln Thr Tyr Ile Cys Asn Val Asn His Lys
             195                 200                 205

Pro Ser Asn Thr Lys Val Asp Lys Lys Val Glu Pro Lys Ser Cys
210                 215                 220
```

<210> SEQ ID NO 9
<211> LENGTH: 217
<212> TYPE: PRT
<213> ORGANISM: Artificial sequence
<220> FEATURE:
<223> OTHER INFORMATION: Synthetic polypeptide

<400> SEQUENCE: 9

```
Asp Ile Gln Met Thr Gln Ser Pro Ser Ile Leu Ser Ala Ser Val Gly
 1               5                  10                  15

Asp Arg Val Thr Ile Thr Cys Arg Ala Ser Glu Ser Val Asp Asn Tyr
                 20                  25                  30

Gly Ile Ser Phe Met Asn Trp Phe Gln Gln Arg Thr Asn Lys Ala Pro
             35                  40                  45

Arg Leu Leu Ile Tyr Ala Ala Ser Asn Gln Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Asp Asp Glu Ala Asp Tyr Tyr Cys Gln Gln Ser Lys
                 85                  90                  95

Glu Val Pro Trp Thr Phe Gly Ala Gly Thr Lys Leu Glu Ile Lys Arg
             100                 105                 110

Thr Val Ala Ala Pro Ser Val Phe Ile Phe Pro Pro Ser Asp Glu Gln
             115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                 165                 170                 175

Tyr Ser Leu Ser Ser Thr Leu Thr Leu Ser Lys Ala Asp Tyr Glu Lys
                 180                 185                 190
```

His Lys Val Tyr Ala Cys Glu Val Thr His Gln Gly Leu Ser Ser Pro
        195                 200                 205

Val Thr Lys Ser Phe Asn Arg Gly Glu
    210                 215

<210> SEQ ID NO 10
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 10

Gly Gly Gly Ser Ser Gly
1               5

<210> SEQ ID NO 11
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 11

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Gly Asn
            20                  25                  30

Val Met Gly Trp Tyr Arg Arg Gln Ala Pro Gly Lys Glu Arg Glu Trp
        35                  40                  45

Val Ala Ala Ile Ala Ser Gly Gly Ser Ile Tyr Tyr Arg Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ser His Pro Pro Thr Leu Pro Tyr Trp Gly Leu Gly Thr Gln Val
            100                 105                 110

Thr Val

<210> SEQ ID NO 12
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 12

Ser Ser Gly Ser
1

<210> SEQ ID NO 13
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Thr Phe Ser Gly Thr Phe Ser Ser Tyr
            20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
 50                  55                  60

Asp Arg Phe Ser Ile Ser Glu Asp Ser Val Lys Asn Ala Val Tyr Leu
 65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
                100                 105                 110

Gly Thr Leu Val Thr Val Ser Ser
            115                 120

<210> SEQ ID NO 14
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 14

Gly Gly Gly Ser Ser Gly
1               5

<210> SEQ ID NO 15
<211> LENGTH: 224
<212> TYPE: PRT
<213> ORGANISM: Artificial sequence
<220> FEATURE:
<223> OTHER INFORMATION: Synthetic polypeptide

<400> SEQUENCE: 15

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met His Trp Val Arg Gln Ser Pro Gly Gln Gly Leu Glu Trp Ile
            35                  40                  45

Gly Tyr Ile Tyr Pro Tyr Asn Gly Gly Thr Gly Tyr Asn Gln Lys Phe
 50                  55                  60

Lys Ser Lys Ala Thr Ile Thr Ala Asp Glu Ser Thr Asn Thr Ala Tyr
 65                  70                  75                  80

Met Glu Leu Ser Ser Leu Arg Ser Glu Asp Thr Ala Ile Tyr Tyr Cys
                85                  90                  95

Ala Arg Gly Arg Pro Ala Met Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Cys Val Leu Gln Ser Ser
                165                 170                 175

Gly Leu Tyr Ser Leu Ser Ser Val Val Thr Val Pro Ser Ser Ser Leu
            180                 185                 190

```
Gly Thr Gln Thr Tyr Ile Cys Asn Val Asn His Lys Pro Ser Asn Thr
            195                 200                 205

Lys Val Asp Lys Lys Val Glu Pro Lys Ser Gly Asp Lys Thr His Thr
    210                 215                 220
```

<210> SEQ ID NO 16
<211> LENGTH: 677
<212> TYPE: PRT
<213> ORGANISM: Artificial sequence
<220> FEATURE:
<223> OTHER INFORMATION: Synthetic polypeptide

<400> SEQUENCE: 16

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335
```

Pro Arg Glu Pro Gln Val Tyr Thr Leu Pro Pro Ser Arg Asp Glu Leu
                340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys Gly Gly Ser Gly Val Pro Leu
        435                 440                 445

Ser Leu Tyr Ser Gly Gly Glu Val Gln Leu Val Glu Ser Gly Gly Gly
    450                 455                 460

Leu Val Gln Pro Gly Gly Ser Leu Arg Leu Ser Cys Ala Ala Ser Gly
465                 470                 475                 480

Phe Asn Ile Lys Asp Thr Tyr Ile His Trp Val Arg Gln Ser Pro Gly
                485                 490                 495

Lys Gly Leu Glu Trp Val Ala Arg Ile Tyr Pro Thr Asn Gly Tyr Thr
            500                 505                 510

Arg Tyr Ala Asp Ser Val Lys Gly Arg Phe Thr Ile Ser Ala Asp Thr
        515                 520                 525

Ser Lys Asn Thr Ala Tyr Leu Gln Met Asn Ser Leu Arg Ala Glu Asp
    530                 535                 540

Thr Ala Ile Tyr Tyr Cys Ser Arg Trp Gly Gly Asp Gly Phe Tyr Ala
545                 550                 555                 560

Met Asp Tyr Trp Gly Gln Gly Thr Leu Val Thr Val Ser Ser Ala Ser
                565                 570                 575

Thr Lys Gly Pro Ser Val Phe Pro Leu Ala Pro Ser Ser Lys Ser Thr
            580                 585                 590

Ser Gly Gly Thr Ala Ala Leu Gly Cys Leu Val Lys Asp Tyr Phe Pro
        595                 600                 605

Glu Pro Val Thr Val Ser Trp Asn Ser Gly Ala Leu Thr Ser Gly Val
    610                 615                 620

His Thr Phe Pro Ala Val Leu Gln Ser Ser Gly Leu Tyr Ser Leu Ser
625                 630                 635                 640

Ser Val Val Thr Val Pro Ser Ser Ser Leu Gly Thr Gln Thr Tyr Ile
                645                 650                 655

Cys Asn Val Asn His Lys Pro Ser Asn Thr Lys Val Asp Lys Lys Val
            660                 665                 670

Glu Pro Lys Ser Cys
        675

<210> SEQ ID NO 17
<211> LENGTH: 227
<212> TYPE: PRT
<213> ORGANISM: Artificial sequence
<220> FEATURE:
<223> OTHER INFORMATION: Synthetic polypeptide

<400> SEQUENCE: 17

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 18
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 18

Gly Gly Ser Gly Val Pro Leu Ser Leu Tyr Ser Gly Gly
1               5                   10

<210> SEQ ID NO 19
<211> LENGTH: 583
<212> TYPE: PRT
<213> ORGANISM: Artificial sequence
<220> FEATURE:
<223> OTHER INFORMATION: Synthetic polypeptide

<400> SEQUENCE: 19

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro

-continued

```
                65                  70                  75                  80
Glu Asp Ile Ala Asp Tyr Tyr Cys Gln Gln His Tyr Thr Thr Pro Pro
                        85                  90                  95
Thr Phe Gly Ala Gly Thr Lys Val Glu Ile Lys Arg Thr Val Ala Ala
                        100                 105                 110
Pro Ser Val Phe Ile Phe Pro Pro Ser Asp Glu Gln Leu Lys Ser Gly
                        115                 120                 125
Thr Ala Ser Val Val Cys Leu Leu Asn Asn Phe Tyr Pro Arg Glu Ala
                        130                 135                 140
Lys Val Gln Trp Lys Val Asp Asn Ala Leu Gln Ser Gly Asn Ser Gln
145                     150                 155                 160
Glu Ser Val Thr Glu Gln Asp Ser Lys Asp Ser Thr Tyr Ser Leu Ser
                        165                 170                 175
Ser Thr Leu Thr Leu Ser Lys Ala Asp Tyr Glu Lys His Lys Val Tyr
                        180                 185                 190
Ala Cys Glu Val Thr His Gln Gly Leu Ser Ser Pro Val Thr Lys Ser
                        195                 200                 205
Phe Asn Arg Gly Glu Cys Gly Gly Ala Gly Gly Ser Thr Ser Thr Ser
            210                 215                 220
Gly Arg Ser Ala Asn Pro Arg Gly Glu Val Gln Leu Thr Glu Ser
225                     230                 235                 240
Gly Gly Glu Asp Val Gln Ala Gly Gly Ser Leu Arg Leu Ser Cys Ser
                        245                 250                 255
Ala Ser Gly Leu Thr Phe Ser Ser Tyr Asn Met Gly Trp Phe Arg Arg
                260                 265                 270
Ala Pro Gly Lys Glu Arg Glu Phe Val Ala Ser Ile Thr Trp Ser Gly
            275                 280                 285
Arg Asp Thr Phe Tyr Ala Asp Ser Val Lys Gly Arg Phe Thr Ile Ser
                290                 295                 300
Arg Asp Asn Ala Lys Asn Thr Val Tyr Leu Gln Met Ser Ser Leu Lys
305                     310                 315                 320
Pro Glu Asp Thr Ala Thr Tyr Tyr Cys Ala Ala Asn Pro Trp Pro Val
                        325                 330                 335
Ala Ala Pro Arg Ser Gly Thr Tyr Trp Gly Glu Gly Thr Gln Val Thr
                        340                 345                 350
Val Ala Ser Gly Ala Gly Ala Ser Glu Val Gln Leu Val Glu Ser Gly
                        355                 360                 365
Gly Gly Leu Val Gln Pro Gly Gly Ser Leu Arg Leu Ser Cys Ala Ala
            370                 375                 380
Ser Gly Phe Asn Ile Lys Asp Thr Tyr Ile His Trp Val Arg Gln Ser
385                     390                 395                 400
Pro Gly Lys Gly Leu Glu Trp Val Ala Arg Ile Tyr Pro Thr Asn Gly
                        405                 410                 415
Tyr Thr Arg Tyr Ala Asp Ser Val Lys Gly Arg Phe Thr Ile Ser Ala
                        420                 425                 430
Asp Thr Ser Lys Asn Thr Ala Tyr Leu Gln Met Asn Ser Leu Arg Ala
            435                 440                 445
Glu Asp Thr Ala Ile Tyr Tyr Cys Ser Arg Trp Gly Gly Asp Gly Phe
            450                 455                 460
Tyr Ala Met Asp Tyr Trp Gly Gln Gly Thr Leu Val Thr Val Ser Ser
465                     470                 475                 480
Ala Ser Thr Lys Gly Pro Ser Val Phe Pro Leu Ala Pro Ser Ser Lys
                        485                 490                 495
```

```
Ser Thr Ser Gly Gly Thr Ala Ala Leu Gly Cys Leu Val Lys Asp Tyr
            500                 505                 510

Phe Pro Glu Pro Val Thr Val Ser Trp Asn Ser Gly Ala Leu Thr Ser
            515                 520                 525

Gly Val His Thr Phe Pro Ala Val Leu Gln Ser Ser Gly Leu Tyr Ser
            530                 535                 540

Leu Ser Ser Val Val Thr Val Pro Ser Ser Leu Gly Thr Gln Thr
545                 550                 555                 560

Tyr Ile Cys Asn Val Asn His Lys Pro Ser Asn Thr Lys Val Asp Lys
                565                 570                 575

Lys Val Glu Pro Lys Ser Cys
            580

<210> SEQ ID NO 20
<211> LENGTH: 579
<212> TYPE: PRT
<213> ORGANISM: Artificial sequence
<220> FEATURE:
<223> OTHER INFORMATION: Synthetic polypeptide

<400> SEQUENCE: 20

Asp Ile Gln Met Thr Gln Ser Pro Ile Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Ala Gly Gly Ser Thr Ser Thr Ser
            210                 215                 220

Gly Arg Ser Ala Asn Pro Arg Gly Gly Glu Val Gln Leu Thr Glu Ser
225                 230                 235                 240

Gly Gly Glu Asp Val Gln Ala Gly Gly Ser Leu Arg Leu Ser Cys Ser
                245                 250                 255

Ala Ser Gly Leu Thr Phe Ser Ser Tyr Asn Met Gly Trp Phe Arg Arg
            260                 265                 270
```

-continued

```
Ala Pro Gly Lys Glu Arg Glu Phe Val Ala Ser Ile Thr Trp Ser Gly
            275                 280                 285

Arg Asp Thr Phe Tyr Ala Asp Ser Val Lys Gly Arg Phe Thr Ile Ser
        290                 295                 300

Arg Asp Asn Ala Lys Asn Thr Val Tyr Leu Gln Met Ser Ser Leu Lys
305                 310                 315                 320

Pro Glu Asp Thr Ala Thr Tyr Tyr Cys Ala Ala Asn Pro Trp Pro Val
                325                 330                 335

Ala Ala Pro Arg Ser Gly Thr Tyr Trp Gly Glu Gly Thr Gln Val Thr
            340                 345                 350

Val Ala Ala Ser Glu Val Gln Leu Val Glu Ser Gly Gly Gly Leu Val
        355                 360                 365

Gln Pro Gly Gly Ser Leu Arg Leu Ser Cys Ala Ala Ser Gly Phe Asn
    370                 375                 380

Ile Lys Asp Thr Tyr Ile His Trp Val Arg Gln Ser Pro Gly Lys Gly
385                 390                 395                 400

Leu Glu Trp Val Ala Arg Ile Tyr Pro Thr Asn Gly Tyr Thr Arg Tyr
                405                 410                 415

Ala Asp Ser Val Lys Gly Arg Phe Thr Ile Ser Ala Thr Ser Lys
            420                 425                 430

Asn Thr Ala Tyr Leu Gln Met Asn Ser Leu Arg Ala Glu Asp Thr Ala
        435                 440                 445

Ile Tyr Tyr Cys Ser Arg Trp Gly Gly Asp Gly Phe Tyr Ala Met Asp
    450                 455                 460

Tyr Trp Gly Gln Gly Thr Leu Val Thr Val Ser Ser Ala Ser Thr Lys
465                 470                 475                 480

Gly Pro Ser Val Phe Pro Leu Ala Pro Ser Ser Lys Ser Thr Ser Gly
                485                 490                 495

Gly Thr Ala Ala Leu Gly Cys Leu Val Lys Asp Tyr Phe Pro Glu Pro
            500                 505                 510

Val Thr Val Ser Trp Asn Ser Gly Ala Leu Thr Ser Gly Val His Thr
        515                 520                 525

Phe Pro Ala Val Leu Gln Ser Ser Gly Leu Tyr Ser Leu Ser Ser Val
    530                 535                 540

Val Thr Val Pro Ser Ser Ser Leu Gly Thr Gln Thr Tyr Ile Cys Asn
545                 550                 555                 560

Val Asn His Lys Pro Ser Asn Thr Lys Val Asp Lys Lys Val Glu Pro
                565                 570                 575

Lys Ser Cys

<210> SEQ ID NO 21
<211> LENGTH: 578
<212> TYPE: PRT
<213> ORGANISM: Artificial sequence
<220> FEATURE:
<223> OTHER INFORMATION: Synthetic polypeptide

<400> SEQUENCE: 21

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45
```

-continued

```
Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Gly Gly Ala Gly Gly Ser Thr Ser Thr Ser
    210                 215                 220

Gly Arg Ser Ala Asn Pro Arg Gly Gly Glu Val Gln Leu Thr Glu Ser
225                 230                 235                 240

Gly Gly Glu Asp Val Gln Ala Gly Gly Ser Leu Arg Leu Ser Cys Ser
                245                 250                 255

Ala Ser Gly Leu Thr Phe Ser Ser Tyr Asn Met Gly Trp Phe Arg Arg
                260                 265                 270

Ala Pro Gly Lys Glu Arg Glu Phe Val Ala Ser Ile Thr Trp Ser Gly
            275                 280                 285

Arg Asp Thr Phe Tyr Ala Asp Ser Val Lys Gly Arg Phe Thr Ile Ser
    290                 295                 300

Arg Asp Asn Ala Lys Asn Thr Val Tyr Leu Gln Met Ser Ser Leu Lys
305                 310                 315                 320

Pro Glu Asp Thr Ala Thr Tyr Tyr Cys Ala Ala Asn Pro Trp Pro Val
                325                 330                 335

Ala Ala Pro Arg Ser Gly Thr Tyr Trp Gly Glu Gly Thr Gln Val Thr
            340                 345                 350

Val Ala Ser Glu Val Gln Leu Val Glu Ser Gly Gly Gly Leu Val Gln
    355                 360                 365

Pro Gly Gly Ser Leu Arg Leu Ser Cys Ala Ala Ser Gly Phe Asn Ile
370                 375                 380

Lys Asp Thr Tyr Ile His Trp Val Arg Gln Ser Pro Gly Lys Gly Leu
385                 390                 395                 400

Glu Trp Val Ala Arg Ile Tyr Pro Thr Asn Gly Tyr Thr Arg Tyr Ala
                405                 410                 415

Asp Ser Val Lys Gly Arg Phe Thr Ile Ser Ala Asp Thr Ser Lys Asn
            420                 425                 430

Thr Ala Tyr Leu Gln Met Asn Ser Leu Arg Ala Glu Asp Thr Ala Ile
    435                 440                 445

Tyr Tyr Cys Ser Arg Trp Gly Gly Asp Gly Phe Tyr Ala Met Asp Tyr
450                 455                 460

Trp Gly Gln Gly Thr Leu Val Thr Val Ser Ser Ala Ser Thr Lys Gly
```

```
                465                 470                 475                 480
Pro Ser Val Phe Pro Leu Ala Pro Ser Ser Lys Ser Thr Ser Gly Gly
                    485                 490                 495

Thr Ala Ala Leu Gly Cys Leu Val Lys Asp Tyr Phe Pro Glu Pro Val
                500                 505                 510

Thr Val Ser Trp Asn Ser Gly Ala Leu Thr Ser Gly Val His Thr Phe
                515                 520                 525

Pro Ala Val Leu Gln Ser Ser Gly Leu Tyr Ser Leu Ser Ser Val Val
                530                 535                 540

Thr Val Pro Ser Ser Leu Gly Thr Gln Thr Tyr Ile Cys Asn Val
545                 550                 555                 560

Asn His Lys Pro Ser Asn Thr Lys Val Asp Lys Lys Val Glu Pro Lys
                565                 570                 575

Ser Cys
```

<210> SEQ ID NO 22
<211> LENGTH: 577
<212> TYPE: PRT
<213> ORGANISM: Artificial sequence
<220> FEATURE:
<223> OTHER INFORMATION: Synthetic polypeptide

<400> SEQUENCE: 22

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Arg Thr Asn Gly Ser Pro Arg Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ala Gly Ser Thr Thr Ser Thr Gly
    210                 215                 220

Arg Ser Ala Asn Pro Arg Gly Gly Glu Val Gln Leu Thr Glu Ser Gly
225                 230                 235                 240

Gly Glu Asp Val Gln Ala Gly Gly Ser Leu Arg Leu Ser Cys Ser Ala
                245                 250                 255
```

```
Ser Gly Leu Thr Phe Ser Ser Tyr Asn Met Gly Trp Phe Arg Arg Ala
            260                 265                 270
Pro Gly Lys Glu Arg Glu Phe Val Ala Ser Ile Thr Trp Ser Gly Arg
            275                 280                 285
Asp Thr Phe Tyr Ala Asp Ser Val Lys Gly Arg Phe Thr Ile Ser Arg
            290                 295                 300
Asp Asn Ala Lys Asn Thr Val Tyr Leu Gln Met Ser Ser Leu Lys Pro
305                 310                 315                 320
Glu Asp Thr Ala Thr Tyr Tyr Cys Ala Ala Asn Pro Trp Pro Val Ala
                325                 330                 335
Ala Pro Arg Ser Gly Thr Tyr Trp Gly Glu Gly Thr Gln Val Thr Val
            340                 345                 350
Ala Ser Glu Val Gln Leu Val Glu Ser Gly Gly Gly Leu Val Gln Pro
            355                 360                 365
Gly Gly Ser Leu Arg Leu Ser Cys Ala Ala Ser Gly Phe Asn Ile Lys
370                 375                 380
Asp Thr Tyr Ile His Trp Val Arg Gln Ser Pro Gly Lys Gly Leu Glu
385                 390                 395                 400
Trp Val Ala Arg Ile Tyr Pro Thr Asn Gly Tyr Thr Arg Tyr Ala Asp
                405                 410                 415
Ser Val Lys Gly Arg Phe Thr Ile Ser Ala Asp Thr Ser Lys Asn Thr
            420                 425                 430
Ala Tyr Leu Gln Met Asn Ser Leu Arg Ala Glu Asp Thr Ala Ile Tyr
            435                 440                 445
Tyr Cys Ser Arg Trp Gly Gly Asp Gly Phe Tyr Ala Met Asp Tyr Trp
450                 455                 460
Gly Gln Gly Thr Leu Val Thr Val Ser Ser Ala Ser Thr Lys Gly Pro
465                 470                 475                 480
Ser Val Phe Pro Leu Ala Pro Ser Ser Lys Ser Thr Ser Gly Gly Thr
                485                 490                 495
Ala Ala Leu Gly Cys Leu Val Lys Asp Tyr Phe Pro Glu Pro Val Thr
            500                 505                 510
Val Ser Trp Asn Ser Gly Ala Leu Thr Ser Gly Val His Thr Phe Pro
            515                 520                 525
Ala Val Leu Gln Ser Ser Gly Leu Tyr Ser Leu Ser Ser Val Val Thr
            530                 535                 540
Val Pro Ser Ser Ser Leu Gly Thr Gln Thr Tyr Ile Cys Asn Val Asn
545                 550                 555                 560
His Lys Pro Ser Asn Thr Lys Val Asp Lys Lys Val Glu Pro Lys Ser
                565                 570                 575
Cys

<210> SEQ ID NO 23
<211> LENGTH: 576
<212> TYPE: PRT
<213> ORGANISM: Artificial sequence
<220> FEATURE:
<223> OTHER INFORMATION: Synthetic polypeptide

<400> SEQUENCE: 23

Asp Ile Gln Met Thr Gln Ser Pro Ile Leu Leu Ser Ala Ser Val Gly
1               5                   10                  15
Asp Arg Val Thr Ile Thr Cys Arg Ala Ser Gln Asp Val Asn Thr Ala
            20                  25                  30
```

-continued

Val Ala Trp Tyr Gln Gln Arg Thr Asn Gly Ser Pro Arg Leu Leu Ile
            35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Ala Ser Thr Ser Thr Ser Gly Arg
    210                 215                 220

Ser Ala Asn Pro Arg Gly Gly Glu Val Gln Leu Thr Glu Ser Gly Gly
225                 230                 235                 240

Glu Asp Val Gln Ala Gly Gly Ser Leu Arg Leu Ser Cys Ser Ala Ser
                245                 250                 255

Gly Leu Thr Phe Ser Ser Tyr Asn Met Gly Trp Phe Arg Arg Ala Pro
            260                 265                 270

Gly Lys Glu Arg Glu Phe Val Ala Ser Ile Thr Trp Ser Gly Arg Asp
            275                 280                 285

Thr Phe Tyr Ala Asp Ser Val Lys Gly Arg Phe Thr Ile Ser Arg Asp
    290                 295                 300

Asn Ala Lys Asn Thr Val Tyr Leu Gln Met Ser Ser Leu Lys Pro Glu
305                 310                 315                 320

Asp Thr Ala Thr Tyr Tyr Cys Ala Ala Asn Pro Trp Pro Val Ala Ala
                325                 330                 335

Pro Arg Ser Gly Thr Tyr Trp Gly Glu Gly Thr Gln Val Thr Val Ala
            340                 345                 350

Ser Glu Val Gln Leu Val Glu Ser Gly Gly Gly Leu Val Gln Pro Gly
            355                 360                 365

Gly Ser Leu Arg Leu Ser Cys Ala Ala Ser Gly Phe Asn Ile Lys Asp
    370                 375                 380

Thr Tyr Ile His Trp Val Arg Gln Ser Pro Gly Lys Gly Leu Glu Trp
385                 390                 395                 400

Val Ala Arg Ile Tyr Pro Thr Asn Gly Tyr Thr Arg Tyr Ala Asp Ser
                405                 410                 415

Val Lys Gly Arg Phe Thr Ile Ser Ala Asp Thr Ser Lys Asn Thr Ala
            420                 425                 430

Tyr Leu Gln Met Asn Ser Leu Arg Ala Glu Asp Thr Ala Ile Tyr Tyr
            435                 440                 445

Cys Ser Arg Trp Gly Gly Asp Gly Phe Tyr Ala Met Asp Tyr Trp Gly

```
              450                 455                 460
Gln Gly Thr Leu Val Thr Val Ser Ser Ala Ser Thr Lys Gly Pro Ser
465                 470                 475                 480

Val Phe Pro Leu Ala Pro Ser Ser Lys Ser Thr Ser Gly Gly Thr Ala
                485                 490                 495

Ala Leu Gly Cys Leu Val Lys Asp Tyr Phe Pro Glu Pro Val Thr Val
                500                 505                 510

Ser Trp Asn Ser Gly Ala Leu Thr Ser Gly Val His Thr Phe Pro Ala
            515                 520                 525

Val Leu Gln Ser Ser Gly Leu Tyr Ser Leu Ser Ser Val Val Thr Val
            530                 535                 540

Pro Ser Ser Ser Leu Gly Thr Gln Thr Tyr Ile Cys Asn Val Asn His
545                 550                 555                 560

Lys Pro Ser Asn Thr Lys Val Asp Lys Lys Val Glu Pro Lys Ser Cys
                565                 570                 575
```

<210> SEQ ID NO 24
<211> LENGTH: 575
<212> TYPE: PRT
<213> ORGANISM: Artificial sequence
<220> FEATURE:
<223> OTHER INFORMATION: Synthetic polypeptide

<400> SEQUENCE: 24

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Arg Thr Asn Gly Ser Pro Arg Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Thr Ser Thr Gly Arg Ser
        210                 215                 220

Ala Asn Pro Arg Gly Gly Glu Val Gln Leu Thr Glu Ser Gly Gly Glu
225                 230                 235                 240

Asp Val Gln Ala Gly Gly Ser Leu Arg Leu Ser Cys Ser Ala Ser Gly
```

245                 250                 255
Leu Thr Phe Ser Ser Tyr Asn Met Gly Trp Phe Arg Arg Ala Pro Gly
            260                 265                 270

Lys Glu Arg Glu Phe Val Ala Ser Ile Thr Trp Ser Gly Arg Asp Thr
        275                 280                 285

Phe Tyr Ala Asp Ser Val Lys Gly Arg Phe Thr Ile Ser Arg Asp Asn
    290                 295                 300

Ala Lys Asn Thr Val Tyr Leu Gln Met Ser Ser Leu Lys Pro Glu Asp
305                 310                 315                 320

Thr Ala Thr Tyr Tyr Cys Ala Ala Asn Pro Trp Pro Val Ala Ala Pro
                325                 330                 335

Arg Ser Gly Thr Tyr Trp Gly Glu Gly Thr Gln Val Thr Val Ala Ser
            340                 345                 350

Glu Val Gln Leu Val Glu Ser Gly Gly Gly Leu Val Gln Pro Gly Gly
        355                 360                 365

Ser Leu Arg Leu Ser Cys Ala Ala Ser Gly Phe Asn Ile Lys Asp Thr
    370                 375                 380

Tyr Ile His Trp Val Arg Gln Ser Pro Gly Lys Gly Leu Glu Trp Val
385                 390                 395                 400

Ala Arg Ile Tyr Pro Thr Asn Gly Tyr Thr Arg Tyr Ala Asp Ser Val
                405                 410                 415

Lys Gly Arg Phe Thr Ile Ser Ala Asp Thr Ser Lys Asn Thr Ala Tyr
            420                 425                 430

Leu Gln Met Asn Ser Leu Arg Ala Glu Asp Thr Ala Ile Tyr Tyr Cys
        435                 440                 445

Ser Arg Trp Gly Gly Asp Gly Phe Tyr Ala Met Asp Tyr Trp Gly Gln
    450                 455                 460

Gly Thr Leu Val Thr Val Ser Ser Ala Ser Thr Lys Gly Pro Ser Val
465                 470                 475                 480

Phe Pro Leu Ala Pro Ser Ser Lys Ser Thr Ser Gly Gly Thr Ala Ala
                485                 490                 495

Leu Gly Cys Leu Val Lys Asp Tyr Phe Pro Glu Pro Val Thr Val Ser
            500                 505                 510

Trp Asn Ser Gly Ala Leu Thr Ser Gly Val His Thr Phe Pro Ala Val
        515                 520                 525

Leu Gln Ser Ser Gly Leu Tyr Ser Leu Ser Ser Val Val Thr Val Pro
    530                 535                 540

Ser Ser Ser Leu Gly Thr Gln Thr Tyr Ile Cys Asn Val Asn His Lys
545                 550                 555                 560

Pro Ser Asn Thr Lys Val Asp Lys Lys Val Glu Pro Lys Ser Cys
                565                 570                 575

<210> SEQ ID NO 25
<211> LENGTH: 574
<212> TYPE: PRT
<213> ORGANISM: Artificial sequence
<220> FEATURE:
<223> OTHER INFORMATION: Synthetic polypeptide

<400> SEQUENCE: 25

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile

```
                35                  40                  45
Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Ile Ala Asp Tyr Tyr Cys Gln Gln His Tyr Thr Thr Pro Pro
                 85                  90                  95

Thr Phe Gly Ala Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Ser Thr Ser Thr Ser Gly Arg Ser Ala
210                 215                 220

Asn Pro Arg Gly Gly Glu Val Gln Leu Thr Glu Ser Gly Gly Glu Asp
225                 230                 235                 240

Val Gln Ala Gly Gly Ser Leu Arg Leu Ser Cys Ser Ala Ser Gly Leu
                245                 250                 255

Thr Phe Ser Ser Tyr Asn Met Gly Trp Phe Arg Arg Ala Pro Gly Lys
            260                 265                 270

Glu Arg Glu Phe Val Ala Ser Ile Thr Trp Ser Gly Arg Asp Thr Phe
        275                 280                 285

Tyr Ala Asp Ser Val Lys Gly Arg Phe Thr Ile Ser Arg Asp Asn Ala
290                 295                 300

Lys Asn Thr Val Tyr Leu Gln Met Ser Ser Leu Lys Pro Glu Asp Thr
305                 310                 315                 320

Ala Thr Tyr Tyr Cys Ala Ala Asn Pro Trp Pro Val Ala Ala Pro Arg
                325                 330                 335

Ser Gly Thr Tyr Trp Gly Glu Gly Thr Gln Val Thr Val Ala Ser Glu
            340                 345                 350

Val Gln Leu Val Glu Ser Gly Gly Gly Leu Val Gln Pro Gly Gly Ser
        355                 360                 365

Leu Arg Leu Ser Cys Ala Ala Ser Gly Phe Asn Ile Lys Asp Thr Tyr
370                 375                 380

Ile His Trp Val Arg Gln Ser Pro Gly Lys Gly Leu Glu Trp Val Ala
385                 390                 395                 400

Arg Ile Tyr Pro Thr Asn Gly Tyr Thr Arg Tyr Ala Asp Ser Val Lys
                405                 410                 415

Gly Arg Phe Thr Ile Ser Ala Asp Thr Ser Lys Asn Thr Ala Tyr Leu
            420                 425                 430

Gln Met Asn Ser Leu Arg Ala Glu Asp Thr Ala Ile Tyr Tyr Cys Ser
        435                 440                 445

Arg Trp Gly Gly Asp Gly Phe Tyr Ala Met Asp Tyr Trp Gly Gln Gly
450                 455                 460
```

```
Thr Leu Val Thr Val Ser Ser Ala Ser Thr Lys Gly Pro Ser Val Phe
465                 470                 475                 480

Pro Leu Ala Pro Ser Ser Lys Ser Thr Ser Gly Gly Thr Ala Ala Leu
                485                 490                 495

Gly Cys Leu Val Lys Asp Tyr Phe Pro Glu Pro Val Thr Val Ser Trp
            500                 505                 510

Asn Ser Gly Ala Leu Thr Ser Gly Val His Thr Phe Pro Ala Val Leu
        515                 520                 525

Gln Ser Ser Gly Leu Tyr Ser Leu Ser Ser Val Val Thr Val Pro Ser
    530                 535                 540

Ser Ser Leu Gly Thr Gln Thr Tyr Ile Cys Asn Val Asn His Lys Pro
545                 550                 555                 560

Ser Asn Thr Lys Val Asp Lys Lys Val Glu Pro Lys Ser Cys
                565                 570
```

<210> SEQ ID NO 26
<211> LENGTH: 573
<212> TYPE: PRT
<213> ORGANISM: Artificial sequence
<220> FEATURE:
<223> OTHER INFORMATION: Synthetic polypeptide

<400> SEQUENCE: 26

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Arg Thr Asn Gly Ser Pro Arg Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Thr Ser Thr Ser Gly Arg Ser Ala Asn
    210                 215                 220

Pro Arg Gly Gly Glu Val Gln Leu Thr Glu Ser Gly Gly Glu Asp Val
225                 230                 235                 240

Gln Ala Gly Gly Ser Leu Arg Leu Ser Cys Ser Ala Ser Gly Leu Thr
                245                 250                 255
```

Phe Ser Ser Tyr Asn Met Gly Trp Phe Arg Arg Ala Pro Gly Lys Glu
                260                 265                 270

Arg Glu Phe Val Ala Ser Ile Thr Trp Ser Gly Arg Asp Thr Phe Tyr
            275                 280                 285

Ala Asp Ser Val Lys Gly Arg Phe Thr Ile Ser Arg Asp Asn Ala Lys
        290                 295                 300

Asn Thr Val Tyr Leu Gln Met Ser Ser Leu Lys Pro Glu Asp Thr Ala
305                 310                 315                 320

Thr Tyr Tyr Cys Ala Ala Asn Pro Trp Pro Val Ala Ala Pro Arg Ser
                325                 330                 335

Gly Thr Tyr Trp Gly Glu Gly Thr Gln Val Thr Val Ala Ser Glu Val
            340                 345                 350

Gln Leu Val Glu Ser Gly Gly Gly Leu Val Gln Pro Gly Gly Ser Leu
        355                 360                 365

Arg Leu Ser Cys Ala Ala Ser Gly Phe Asn Ile Lys Asp Thr Tyr Ile
370                 375                 380

His Trp Val Arg Gln Ser Pro Gly Lys Gly Leu Glu Trp Val Ala Arg
385                 390                 395                 400

Ile Tyr Pro Thr Asn Gly Tyr Thr Arg Tyr Ala Asp Ser Val Lys Gly
                405                 410                 415

Arg Phe Thr Ile Ser Ala Asp Thr Ser Lys Asn Thr Ala Tyr Leu Gln
            420                 425                 430

Met Asn Ser Leu Arg Ala Glu Asp Thr Ala Ile Tyr Tyr Cys Ser Arg
        435                 440                 445

Trp Gly Gly Asp Gly Phe Tyr Ala Met Asp Tyr Trp Gly Gln Gly Thr
                455                 460
        450

Leu Val Thr Val Ser Ser Ala Ser Thr Lys Gly Pro Ser Val Phe Pro
465                 470                 475                 480

Leu Ala Pro Ser Ser Lys Ser Thr Ser Gly Gly Thr Ala Ala Leu Gly
                485                 490                 495

Cys Leu Val Lys Asp Tyr Phe Pro Glu Pro Val Thr Val Ser Trp Asn
            500                 505                 510

Ser Gly Ala Leu Thr Ser Gly Val His Thr Phe Pro Ala Val Leu Gln
        515                 520                 525

Ser Ser Gly Leu Tyr Ser Leu Ser Ser Val Val Thr Val Pro Ser Ser
530                 535                 540

Ser Leu Gly Thr Gln Thr Tyr Ile Cys Asn Val Asn His Lys Pro Ser
545                 550                 555                 560

Asn Thr Lys Val Asp Lys Lys Val Glu Pro Lys Ser Cys
                565                 570

<210> SEQ ID NO 27
<211> LENGTH: 573
<212> TYPE: PRT
<213> ORGANISM: Artificial sequence
<220> FEATURE:
<223> OTHER INFORMATION: Synthetic polypeptide

<400> SEQUENCE: 27

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

```
Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Ile Ala Asp Tyr Tyr Cys Gln Gln His Tyr Thr Thr Pro Pro
                 85                  90                  95

Thr Phe Gly Ala Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Thr Ser Thr Gly Arg Ser Ala Asn Pro
210                 215                 220

Arg Gly Gly Glu Val Gln Leu Thr Glu Ser Gly Gly Glu Asp Val Gln
225                 230                 235                 240

Ala Gly Gly Ser Leu Arg Leu Ser Cys Ser Ala Ser Gly Leu Thr Phe
                245                 250                 255

Ser Ser Tyr Asn Met Gly Trp Phe Arg Arg Ala Pro Gly Lys Glu Arg
            260                 265                 270

Glu Phe Val Ala Ser Ile Thr Trp Ser Gly Arg Asp Thr Phe Tyr Ala
        275                 280                 285

Asp Ser Val Lys Gly Arg Phe Thr Ile Ser Arg Asp Asn Ala Lys Asn
290                 295                 300

Thr Val Tyr Leu Gln Met Ser Ser Leu Lys Pro Glu Asp Thr Ala Thr
305                 310                 315                 320

Tyr Tyr Cys Ala Ala Asn Pro Trp Pro Val Ala Ala Pro Arg Ser Gly
                325                 330                 335

Thr Tyr Trp Gly Glu Gly Thr Gln Val Thr Val Ala Ala Ser Glu Val
            340                 345                 350

Gln Leu Val Glu Ser Gly Gly Gly Leu Val Gln Pro Gly Gly Ser Leu
        355                 360                 365

Arg Leu Ser Cys Ala Ala Ser Gly Phe Asn Ile Lys Asp Thr Tyr Ile
370                 375                 380

His Trp Val Arg Gln Ser Pro Gly Lys Gly Leu Glu Trp Val Ala Arg
385                 390                 395                 400

Ile Tyr Pro Thr Asn Gly Tyr Thr Arg Tyr Ala Asp Ser Val Lys Gly
                405                 410                 415

Arg Phe Thr Ile Ser Ala Asp Thr Ser Lys Asn Thr Ala Tyr Leu Gln
            420                 425                 430

Met Asn Ser Leu Arg Ala Glu Asp Thr Ala Ile Tyr Tyr Cys Ser Arg
        435                 440                 445

Trp Gly Gly Asp Gly Phe Tyr Ala Met Asp Tyr Trp Gly Gln Gly Thr
450                 455                 460
```

Leu Val Thr Val Ser Ser Ala Ser Thr Lys Gly Pro Ser Val Phe Pro
465                 470                 475                 480

Leu Ala Pro Ser Ser Lys Ser Thr Ser Gly Gly Thr Ala Ala Leu Gly
                485                 490                 495

Cys Leu Val Lys Asp Tyr Phe Pro Glu Pro Val Thr Val Ser Trp Asn
                500                 505                 510

Ser Gly Ala Leu Thr Ser Gly Val His Thr Phe Pro Ala Val Leu Gln
                515                 520                 525

Ser Ser Gly Leu Tyr Ser Leu Ser Ser Val Val Thr Val Pro Ser Ser
                530                 535                 540

Ser Leu Gly Thr Gln Thr Tyr Ile Cys Asn Val Asn His Lys Pro Ser
545                 550                 555                 560

Asn Thr Lys Val Asp Lys Lys Val Glu Pro Lys Ser Cys
                565                 570

<210> SEQ ID NO 28
<211> LENGTH: 571
<212> TYPE: PRT
<213> ORGANISM: Artificial sequence
<220> FEATURE:
<223> OTHER INFORMATION: Synthetic polypeptide

<400> SEQUENCE: 28

Asp Ile Gln Met Thr Gln Ser Pro Ile Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Arg Thr Asn Gly Ser Pro Arg Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Ser Thr Ser Gly Arg Ser Ala Asn Pro Arg
        210                 215                 220

Gly Gly Glu Val Gln Leu Thr Glu Ser Gly Gly Glu Asp Val Gln Ala
225                 230                 235                 240

Gly Gly Ser Leu Arg Leu Ser Cys Ser Ala Ser Gly Leu Thr Phe Ser
                245                 250                 255

```
Ser Tyr Asn Met Gly Trp Phe Arg Arg Ala Pro Gly Lys Glu Arg Glu
            260                 265                 270

Phe Val Ala Ser Ile Thr Trp Ser Gly Arg Asp Thr Phe Tyr Ala Asp
        275                 280                 285

Ser Val Lys Gly Arg Phe Thr Ile Ser Arg Asp Asn Ala Lys Asn Thr
290                 295                 300

Val Tyr Leu Gln Met Ser Ser Leu Lys Pro Glu Asp Thr Ala Thr Tyr
305                 310                 315                 320

Tyr Cys Ala Ala Asn Pro Trp Pro Val Ala Ala Pro Arg Ser Gly Thr
                325                 330                 335

Tyr Trp Gly Glu Gly Thr Gln Val Thr Val Ala Ser Glu Val Gln Leu
            340                 345                 350

Val Glu Ser Gly Gly Gly Leu Val Gln Pro Gly Gly Ser Leu Arg Leu
        355                 360                 365

Ser Cys Ala Ala Ser Gly Phe Asn Ile Lys Asp Thr Tyr Ile His Trp
370                 375                 380

Val Arg Gln Ser Pro Gly Lys Gly Leu Glu Trp Val Ala Arg Ile Tyr
385                 390                 395                 400

Pro Thr Asn Gly Tyr Thr Arg Tyr Ala Asp Ser Val Lys Gly Arg Phe
                405                 410                 415

Thr Ile Ser Ala Asp Thr Ser Lys Asn Thr Ala Tyr Leu Gln Met Asn
            420                 425                 430

Ser Leu Arg Ala Glu Asp Thr Ala Ile Tyr Tyr Cys Ser Arg Trp Gly
        435                 440                 445

Gly Asp Gly Phe Tyr Ala Met Asp Tyr Trp Gly Gln Gly Thr Leu Val
450                 455                 460

Thr Val Ser Ser Ala Ser Thr Lys Gly Pro Ser Val Phe Pro Leu Ala
465                 470                 475                 480

Pro Ser Ser Lys Ser Thr Ser Gly Gly Thr Ala Ala Leu Gly Cys Leu
                485                 490                 495

Val Lys Asp Tyr Phe Pro Glu Pro Val Thr Val Ser Trp Asn Ser Gly
            500                 505                 510

Ala Leu Thr Ser Gly Val His Thr Phe Pro Ala Val Leu Gln Ser Ser
        515                 520                 525

Gly Leu Tyr Ser Leu Ser Ser Val Val Thr Val Pro Ser Ser Ser Leu
530                 535                 540

Gly Thr Gln Thr Tyr Ile Cys Asn Val Asn His Lys Pro Ser Asn Thr
545                 550                 555                 560

Lys Val Asp Lys Lys Val Glu Pro Lys Ser Cys
                565                 570

<210> SEQ ID NO 29
<211> LENGTH: 570
<212> TYPE: PRT
<213> ORGANISM: Artificial sequence
<220> FEATURE:
<223> OTHER INFORMATION: Synthetic polypeptide

<400> SEQUENCE: 29

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45
```

-continued

Tyr Ser Ala Ser Phe Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
65                   70                  75                  80

Glu Asp Ile Ala Asp Tyr Tyr Cys Gln Gln His Tyr Thr Thr Pro Pro
                 85                  90                  95

Thr Phe Gly Ala Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Ser Thr Gly Arg Ser Ala Asn Pro Arg Gly
210                 215                 220

Gly Glu Val Gln Leu Thr Glu Ser Gly Gly Glu Asp Val Gln Ala Gly
225                 230                 235                 240

Gly Ser Leu Arg Leu Ser Cys Ser Ala Ser Gly Leu Thr Phe Ser Ser
                245                 250                 255

Tyr Asn Met Gly Trp Phe Arg Arg Ala Pro Gly Lys Glu Arg Glu Phe
            260                 265                 270

Val Ala Ser Ile Thr Trp Ser Gly Arg Asp Thr Phe Tyr Ala Asp Ser
            275                 280                 285

Val Lys Gly Arg Phe Thr Ile Ser Arg Asp Asn Ala Lys Asn Thr Val
290                 295                 300

Tyr Leu Gln Met Ser Ser Leu Lys Pro Glu Asp Thr Ala Thr Tyr Tyr
305                 310                 315                 320

Cys Ala Ala Asn Pro Trp Pro Val Ala Ala Pro Arg Ser Gly Thr Tyr
                325                 330                 335

Trp Gly Glu Gly Thr Gln Val Thr Val Ala Ser Glu Val Gln Leu Val
            340                 345                 350

Glu Ser Gly Gly Gly Leu Val Gln Pro Gly Gly Ser Leu Arg Leu Ser
            355                 360                 365

Cys Ala Ala Ser Gly Phe Asn Ile Lys Asp Thr Tyr Ile His Trp Val
370                 375                 380

Arg Gln Ser Pro Gly Lys Gly Leu Glu Trp Val Ala Arg Ile Tyr Pro
385                 390                 395                 400

Thr Asn Gly Tyr Thr Arg Tyr Ala Asp Ser Val Lys Gly Arg Phe Thr
                405                 410                 415

Ile Ser Ala Asp Thr Ser Lys Asn Thr Ala Tyr Leu Gln Met Asn Ser
            420                 425                 430

Leu Arg Ala Glu Asp Thr Ala Ile Tyr Tyr Cys Ser Arg Trp Gly Gly
            435                 440                 445

Asp Gly Phe Tyr Ala Met Asp Tyr Trp Gly Gln Gly Thr Leu Val Thr
450                 455                 460

Val Ser Ser Ala Ser Thr Lys Gly Pro Ser Val Phe Pro Leu Ala Pro

```
                465                 470                 475                 480
Ser Ser Lys Ser Thr Ser Gly Gly Thr Ala Ala Leu Gly Cys Leu Val
            485                 490                 495

Lys Asp Tyr Phe Pro Glu Pro Val Thr Val Ser Trp Asn Ser Gly Ala
            500                 505                 510

Leu Thr Ser Gly Val His Thr Phe Pro Ala Val Leu Gln Ser Ser Gly
            515                 520                 525

Leu Tyr Ser Leu Ser Ser Val Val Thr Val Pro Ser Ser Ser Leu Gly
            530                 535                 540

Thr Gln Thr Tyr Ile Cys Asn Val Asn His Lys Pro Ser Asn Thr Lys
545                 550                 555                 560

Val Asp Lys Lys Val Glu Pro Lys Ser Cys
            565                 570

<210> SEQ ID NO 30
<211> LENGTH: 569
<212> TYPE: PRT
<213> ORGANISM: Artificial sequence
<220> FEATURE:
<223> OTHER INFORMATION: Synthetic polypeptide

<400> SEQUENCE: 30

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
            35                  40                  45

Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Ser Gly Arg Ser Ala Asn Pro Arg Gly Gly
            210                 215                 220

Glu Val Gln Leu Thr Glu Ser Gly Gly Glu Asp Val Gln Ala Gly Gly
225                 230                 235                 240

Ser Leu Arg Leu Ser Cys Ser Ala Ser Gly Leu Thr Phe Ser Ser Tyr
                245                 250                 255

Asn Met Gly Trp Phe Arg Arg Ala Pro Gly Lys Glu Arg Glu Phe Val
```

Ala Ser Ile Thr Trp Ser Gly Arg Asp Thr Phe Tyr Ala Asp Ser Val
            260                 265                 270

Lys Gly Arg Phe Thr Ile Ser Arg Asp Asn Ala Lys Asn Thr Val Tyr
        275                 280                 285

Leu Gln Met Ser Ser Leu Lys Pro Glu Asp Thr Ala Thr Tyr Tyr Cys
    290                 295                 300

Ala Ala Asn Pro Trp Pro Val Ala Ala Pro Arg Ser Gly Thr Tyr Trp
305                 310                 315                 320

Gly Glu Gly Thr Gln Val Thr Val Ala Ser Glu Val Gln Leu Val Glu
            325                 330                 335

Ser Gly Gly Gly Leu Val Gln Pro Gly Gly Ser Leu Arg Leu Ser Cys
        340                 345                 350

Ala Ala Ser Gly Phe Asn Ile Lys Asp Thr Tyr Ile His Trp Val Arg
    355                 360                 365

Gln Ser Pro Gly Lys Gly Leu Glu Trp Val Ala Arg Ile Tyr Pro Thr
370                 375                 380

Asn Gly Tyr Thr Arg Tyr Ala Asp Ser Val Lys Gly Arg Phe Thr Ile
385                 390                 395                 400

Ser Ala Asp Thr Ser Lys Asn Thr Ala Tyr Leu Gln Met Asn Ser Leu
            405                 410                 415

Arg Ala Glu Asp Thr Ala Ile Tyr Tyr Cys Ser Arg Trp Gly Gly Asp
        420                 425                 430

Gly Phe Tyr Ala Met Asp Tyr Trp Gly Gln Gly Thr Leu Val Thr Val
    435                 440                 445

Ser Ser Ala Ser Thr Lys Gly Pro Ser Val Phe Pro Leu Ala Pro Ser
450                 455                 460

Ser Lys Ser Thr Ser Gly Gly Thr Ala Ala Leu Gly Cys Leu Val Lys
465                 470                 475                 480

Asp Tyr Phe Pro Glu Pro Val Thr Val Ser Trp Asn Ser Gly Ala Leu
            485                 490                 495

Thr Ser Gly Val His Thr Phe Pro Ala Val Leu Gln Ser Ser Gly Leu
        500                 505                 510

Tyr Ser Leu Ser Ser Val Val Thr Val Pro Ser Ser Ser Leu Gly Thr
    515                 520                 525

Gln Thr Tyr Ile Cys Asn Val Asn His Lys Pro Ser Asn Thr Lys Val
530                 535                 540

Asp Lys Lys Val Glu Pro Lys Ser Cys
545                 550                 555

Asp Lys Lys Val Glu Pro Lys Ser Cys
            565

<210> SEQ ID NO 31
<211> LENGTH: 568
<212> TYPE: PRT
<213> ORGANISM: Artificial sequence
<220> FEATURE:
<223> OTHER INFORMATION: Synthetic polypeptide

<400> SEQUENCE: 31

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly

```
                50              55              60
Ser Arg Ser Gly Thr Asp Phe Thr Leu Thr Ile Ser Ser Leu Gln Pro
 65                  70                  75                  80

Glu Asp Ile Ala Asp Tyr Tyr Cys Gln Gln His Tyr Thr Thr Pro Pro
                     85                  90                  95

Thr Phe Gly Ala Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys Gly Arg Ser Ala Asn Pro Arg Gly Gly Glu
210                 215                 220

Val Gln Leu Thr Glu Ser Gly Gly Glu Asp Val Gln Ala Gly Gly Ser
225                 230                 235                 240

Leu Arg Leu Ser Cys Ser Ala Ser Gly Leu Thr Phe Ser Ser Tyr Asn
                245                 250                 255

Met Gly Trp Phe Arg Arg Ala Pro Gly Lys Glu Arg Glu Phe Val Ala
                260                 265                 270

Ser Ile Thr Trp Ser Gly Arg Asp Thr Phe Tyr Ala Asp Ser Val Lys
                275                 280                 285

Gly Arg Phe Thr Ile Ser Arg Asp Asn Ala Lys Asn Thr Val Tyr Leu
                290                 295                 300

Gln Met Ser Ser Leu Lys Pro Glu Asp Thr Ala Thr Tyr Tyr Cys Ala
305                 310                 315                 320

Ala Asn Pro Trp Pro Val Ala Ala Pro Arg Ser Gly Thr Tyr Trp Gly
                325                 330                 335

Glu Gly Thr Gln Val Thr Val Ala Ser Glu Val Gln Leu Val Glu Ser
                340                 345                 350

Gly Gly Gly Leu Val Gln Pro Gly Gly Ser Leu Arg Leu Ser Cys Ala
                355                 360                 365

Ala Ser Gly Phe Asn Ile Lys Asp Thr Tyr Ile His Trp Val Arg Gln
370                 375                 380

Ser Pro Gly Lys Gly Leu Glu Trp Val Ala Arg Ile Tyr Pro Thr Asn
385                 390                 395                 400

Gly Tyr Thr Arg Tyr Ala Asp Ser Val Lys Gly Arg Phe Thr Ile Ser
                405                 410                 415

Ala Asp Thr Ser Lys Asn Thr Ala Tyr Leu Gln Met Asn Ser Leu Arg
                420                 425                 430

Ala Glu Asp Thr Ala Ile Tyr Tyr Cys Ser Arg Trp Gly Gly Asp Gly
                435                 440                 445

Phe Tyr Ala Met Asp Tyr Trp Gly Gln Gly Thr Leu Val Thr Val Ser
                450                 455                 460

Ser Ala Ser Thr Lys Gly Pro Ser Val Phe Pro Leu Ala Pro Ser Ser
465                 470                 475                 480
```

```
Lys Ser Thr Ser Gly Gly Thr Ala Ala Leu Gly Cys Leu Val Lys Asp
                485                 490                 495

Tyr Phe Pro Glu Pro Val Thr Val Ser Trp Asn Ser Gly Ala Leu Thr
            500                 505                 510

Ser Gly Val His Thr Phe Pro Ala Val Leu Gln Ser Ser Gly Leu Tyr
        515                 520                 525

Ser Leu Ser Ser Val Val Thr Val Pro Ser Ser Ser Leu Gly Thr Gln
    530                 535                 540

Thr Tyr Ile Cys Asn Val Asn His Lys Pro Ser Asn Thr Lys Val Asp
545                 550                 555                 560

Lys Lys Val Glu Pro Lys Ser Cys
                565
```

<210> SEQ ID NO 32
<211> LENGTH: 567
<212> TYPE: PRT
<213> ORGANISM: Artificial sequence
<220> FEATURE:
<223> OTHER INFORMATION: Synthetic polypeptide

<400> SEQUENCE: 32

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Ser Ala Asn Pro Arg Gly Gly Glu Val
    210                 215                 220

Gln Leu Thr Glu Ser Gly Gly Glu Asp Val Gln Ala Gly Gly Ser Leu
225                 230                 235                 240

Arg Leu Ser Cys Ser Ala Ser Gly Leu Thr Phe Ser Ser Tyr Asn Met
                245                 250                 255

Gly Trp Phe Arg Arg Ala Pro Gly Lys Glu Arg Glu Phe Val Ala Ser
            260                 265                 270
```

Ile Thr Trp Ser Gly Arg Asp Thr Phe Tyr Ala Asp Ser Val Lys Gly
            275                 280                 285

Arg Phe Thr Ile Ser Arg Asp Asn Ala Lys Asn Thr Val Tyr Leu Gln
        290                 295                 300

Met Ser Ser Leu Lys Pro Glu Asp Thr Ala Thr Tyr Tyr Cys Ala Ala
305                 310                 315                 320

Asn Pro Trp Pro Val Ala Ala Pro Arg Ser Gly Thr Tyr Trp Gly Glu
                325                 330                 335

Gly Thr Gln Val Thr Val Ala Ser Glu Val Gln Leu Val Glu Ser Gly
            340                 345                 350

Gly Gly Leu Val Gln Pro Gly Gly Ser Leu Arg Leu Ser Cys Ala Ala
        355                 360                 365

Ser Gly Phe Asn Ile Lys Asp Thr Tyr Ile His Trp Val Arg Gln Ser
    370                 375                 380

Pro Gly Lys Gly Leu Glu Trp Val Ala Arg Ile Tyr Pro Thr Asn Gly
385                 390                 395                 400

Tyr Thr Arg Tyr Ala Asp Ser Val Lys Gly Arg Phe Thr Ile Ser Ala
                405                 410                 415

Asp Thr Ser Lys Asn Thr Ala Tyr Leu Gln Met Asn Ser Leu Arg Ala
            420                 425                 430

Glu Asp Thr Ala Ile Tyr Tyr Cys Ser Arg Trp Gly Gly Asp Gly Phe
        435                 440                 445

Tyr Ala Met Asp Tyr Trp Gly Gln Gly Thr Leu Val Thr Val Ser Ser
    450                 455                 460

Ala Ser Thr Lys Gly Pro Ser Val Phe Pro Leu Ala Pro Ser Ser Lys
465                 470                 475                 480

Ser Thr Ser Gly Gly Thr Ala Ala Leu Gly Cys Leu Val Lys Asp Tyr
                485                 490                 495

Phe Pro Glu Pro Val Thr Val Ser Trp Asn Ser Gly Ala Leu Thr Ser
            500                 505                 510

Gly Val His Thr Phe Pro Ala Val Leu Gln Ser Ser Gly Leu Tyr Ser
        515                 520                 525

Leu Ser Ser Val Val Thr Val Pro Ser Ser Ser Leu Gly Thr Gln Thr
    530                 535                 540

Tyr Ile Cys Asn Val Asn His Lys Pro Ser Asn Thr Lys Val Asp Lys
545                 550                 555                 560

Lys Val Glu Pro Lys Ser Cys
                565

<210> SEQ ID NO 33
<211> LENGTH: 517
<212> TYPE: PRT
<213> ORGANISM: Artificial sequence
<220> FEATURE:
<223> OTHER INFORMATION: Synthetic polypeptide

<400> SEQUENCE: 33

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

-continued

```
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Ser Cys Gly Gly Ser Ala Ala
210                 215                 220

Ser Ser Pro Ser Gly Gly Pro Ala Ser Val Asp Asn Lys Phe Asn
225                 230                 235                 240

Lys Glu Met Arg Asn Ala Tyr Trp Glu Ile Ala Leu Leu Pro Asn Leu
                245                 250                 255

Asn Asn Gln Gln Lys Arg Ala Phe Ile Arg Ser Leu Tyr Asp Asp Pro
            260                 265                 270

Ser Gln Ser Ala Asn Leu Leu Ala Glu Ala Lys Lys Leu Asn Asp Ala
        275                 280                 285

Gln Ala Pro Lys Gly Gly Pro Ala Ser Gly Ala Pro Ser Ser Ala Ser
    290                 295                 300

Tyr Glu Leu Thr Gln Pro Pro Ser Val Ser Val Ser Pro Gly Gln Thr
305                 310                 315                 320

Ala Ser Ile Thr Cys Ser Gly Asp Asn Ile Gly Asp Gln Tyr Ala His
                325                 330                 335

Trp Tyr Gln Gln Lys Pro Gly Gln Ser Pro Val Leu Val Ile Tyr Gln
            340                 345                 350

Asp Lys Asn Arg Pro Ser Gly Ile Pro Glu Arg Phe Ser Gly Ser Asn
        355                 360                 365

Ser Gly Asn Thr Ala Thr Leu Thr Ile Ser Gly Thr Gln Ala Met Asp
    370                 375                 380

Glu Ala Asp Tyr Tyr Cys Ala Thr Tyr Thr Gly Phe Gly Ser Leu Ala
385                 390                 395                 400

Val Phe Gly Gly Gly Thr Lys Leu Thr Val Leu Gly Gln Pro Lys Ala
                405                 410                 415

Ala Pro Ser Val Thr Leu Phe Pro Pro Ser Ser Glu Glu Leu Gln Ala
            420                 425                 430

Asn Lys Ala Thr Leu Val Cys Leu Ile Ser Asp Phe Tyr Pro Gly Ala
        435                 440                 445

Val Thr Val Ala Trp Lys Ala Asp Ser Ser Pro Val Lys Ala Gly Val
    450                 455                 460

Glu Thr Thr Thr Pro Ser Lys Gln Ser Asn Asn Lys Tyr Ala Ala Ser
465                 470                 475                 480
```

```
Ser Tyr Leu Ser Leu Thr Pro Glu Gln Trp Lys Ser His Arg Ser Tyr
            485                 490                 495

Ser Cys Gln Val Thr His Glu Gly Ser Thr Val Glu Lys Thr Val Ala
            500                 505                 510

Pro Thr Glu Cys Ser
        515

<210> SEQ ID NO 34
<211> LENGTH: 689
<212> TYPE: PRT
<213> ORGANISM: Artificial sequence
<220> FEATURE:
<223> OTHER INFORMATION: Synthetic polypeptide

<400> SEQUENCE: 34

Asp Ile Gln Met Thr Gln Ser Pro Ser Ile Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Arg Thr Asn Lys Ala Pro
        35                  40                  45

Arg Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Asp Asp Glu Ala Asp Tyr Tyr Cys Gln Gln Ser Lys
                85                  90                  95

Glu Val Pro Trp Thr Phe Gly Ala Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Ser Ser Gly
    210                 215                 220

Glu Val Gln Leu Val Glu Ser Gly Gly Gly Leu Val Gln Ala Gly Gly
225                 230                 235                 240

Ser Leu Arg Leu Ser Cys Ala Ala Ser Gly Ser Ile Phe Ser Gly Asn
                245                 250                 255

Val Met Gly Trp Tyr Arg Arg Gln Ala Pro Gly Lys Glu Arg Glu Trp
            260                 265                 270

Val Ala Ala Ile Ala Ser Gly Gly Ser Ile Tyr Tyr Arg Asp Ser Val
        275                 280                 285

Lys Gly Arg Phe Thr Ile Ser Arg Asp Asn Ala Lys Asn Thr Val Tyr
    290                 295                 300

Leu Gln Met Asn Ser Leu Lys Pro Glu Asp Thr Ala Val Tyr Tyr Cys
305                 310                 315                 320
```

Asn Ser His Pro Pro Thr Leu Pro Tyr Trp Gly Leu Gly Thr Gln Val
            325                 330                 335

Thr Val Ser Ser Gly Ser Glu Val Gln Leu Val Glu Ser Gly Gly Gly
        340                 345                 350

Leu Val Gln Pro Gly Gly Ser Leu Arg Leu Ser Cys Thr Phe Ser Gly
        355                 360                 365

Gly Thr Phe Ser Ser Tyr Thr Met Gly Trp Phe Arg Gln Ala Pro Gly
        370                 375                 380

Lys Glu Arg Glu Phe Val Ala Glu Val Arg Trp Gly Val Thr Thr
385                 390                 395                 400

Tyr Ser Asn Ser Leu Lys Asp Arg Phe Ser Ile Ser Glu Asp Ser Val
                405                 410                 415

Lys Asn Ala Val Tyr Leu Gln Met Asn Ser Leu Lys Pro Glu Asp Thr
                420                 425                 430

Ala Val Tyr Tyr Cys Ala Ala Val Arg Gln Met Tyr Met Thr Val Val
            435                 440                 445

Pro Asp Tyr Trp Gly Gln Gly Thr Leu Val Thr Val Ser Ser Gly Gly
        450                 455                 460

Gly Ser Ser Gly Glu Val Gln Leu Val Gln Ser Gly Ala Glu Val Lys
465                 470                 475                 480

Lys Pro Gly Ser Ser Val Lys Val Ser Cys Lys Ala Ser Gly Tyr Thr
                485                 490                 495

Phe Thr Asp Tyr Asn Met His Trp Val Arg Gln Ser Pro Gly Gln Gly
                500                 505                 510

Leu Glu Trp Ile Gly Tyr Ile Tyr Pro Tyr Asn Gly Gly Thr Gly Tyr
            515                 520                 525

Asn Gln Lys Phe Lys Ser Lys Ala Thr Ile Thr Ala Asp Glu Ser Thr
530                 535                 540

Asn Thr Ala Tyr Met Glu Leu Ser Ser Leu Arg Ser Glu Asp Thr Ala
545                 550                 555                 560

Ile Tyr Tyr Cys Ala Arg Gly Arg Pro Ala Met Asp Tyr Trp Gly Gln
                565                 570                 575

Gly Thr Leu Val Thr Val Ser Ser Ala Ser Thr Lys Gly Pro Ser Val
            580                 585                 590

Phe Pro Leu Ala Pro Ser Ser Lys Ser Thr Ser Gly Gly Thr Ala Ala
            595                 600                 605

Leu Gly Cys Leu Val Lys Asp Tyr Phe Pro Glu Pro Val Thr Val Ser
        610                 615                 620

Trp Asn Ser Gly Ala Leu Thr Ser Gly Val His Thr Phe Pro Cys Val
625                 630                 635                 640

Leu Gln Ser Ser Gly Leu Tyr Ser Leu Ser Ser Val Val Thr Val Pro
                645                 650                 655

Ser Ser Ser Leu Gly Thr Gln Thr Tyr Ile Cys Asn Val Asn His Lys
            660                 665                 670

Pro Ser Asn Thr Lys Val Asp Lys Lys Val Glu Pro Lys Ser Gly Asp
        675                 680                 685

Lys

<210> SEQ ID NO 35
<211> LENGTH: 656
<212> TYPE: PRT
<213> ORGANISM: Artificial sequence
<220> FEATURE:
<223> OTHER INFORMATION: Synthetic polypeptide

<400> SEQUENCE: 35

```
Cys Arg His Asp Gln Pro Met Leu Cys Gly Gly Ser Gly Val Pro Leu
1               5                   10                  15
Ser Leu Tyr Ser Gly Gly Asp Ile Gln Met Thr Gln Ser Pro Ile Leu
            20                  25                  30
Leu Ser Ala Ser Val Gly Asp Arg Val Thr Ile Thr Cys Ser Ala Ser
        35                  40                  45
Ser Ser Val Ser Tyr Met Asn Trp Tyr Gln Gln Arg Thr Asn Gly Ser
    50                  55                  60
Pro Arg Leu Leu Ile Tyr Asp Thr Ser Lys Leu Ala Ser Gly Val Pro
65                  70                  75                  80
Ser Arg Phe Ser Gly Ser Arg Ser Gly Thr Asp Phe Thr Leu Thr Ile
                85                  90                  95
Ser Ser Leu Gln Pro Glu Asp Glu Ala Asp Tyr Tyr Cys Gln Gln Trp
            100                 105                 110
Ser Ser Asn Pro Phe Thr Phe Gly Ala Gly Thr Lys Val Glu Ile Lys
        115                 120                 125
Arg Thr Val Ala Ala Pro Ser Val Phe Ile Phe Pro Pro Ser Asp Glu
    130                 135                 140
Gln Leu Lys Ser Gly Thr Ala Ser Val Val Cys Leu Leu Asn Asn Phe
145                 150                 155                 160
Tyr Pro Arg Glu Ala Lys Val Gln Trp Lys Val Asp Asn Ala Leu Gln
                165                 170                 175
Ser Gly Asn Ser Gln Glu Ser Val Thr Glu Gln Asp Ser Lys Asp Ser
            180                 185                 190
Thr Tyr Ser Leu Ser Ser Thr Leu Thr Leu Ser Lys Ala Asp Tyr Glu
        195                 200                 205
Lys His Lys Val Tyr Ala Cys Glu Val Thr His Gln Gly Leu Ser Ser
    210                 215                 220
Pro Val Thr Lys Ser Phe Asn Arg Gly Glu Cys Ala Gly Pro Ser Ser
225                 230                 235                 240
Gly Ala Ser Gly Ser Gln Asp Ser Thr Ser Asp Leu Ile Pro Ala Pro
                245                 250                 255
Pro Leu Ser Lys Val Pro Leu Gln Gln Asn Phe Gln Asp Asn Gln Phe
            260                 265                 270
His Gly Lys Trp Tyr Val Val Gly Leu Ala Gly Asn Val Ile Leu Arg
        275                 280                 285
Glu Asp Lys Asp Pro Tyr Lys Met Ser Ala Thr Ile Tyr Glu Leu Lys
    290                 295                 300
Glu Asp Lys Ser Tyr Asn Val Thr Asn Val Arg Phe Tyr Leu Asn Lys
305                 310                 315                 320
Cys Tyr Tyr Thr Ile Ala Thr Phe Val Pro Gly Ser Arg Pro Gly Glu
                325                 330                 335
Phe Thr Leu Gly Thr Ile Lys Ser Gly Pro Gly Lys Thr Ser Gly Leu
            340                 345                 350
Val Arg Val Val Ser Thr Asn Tyr Ser Gln His Ala Met Val Phe Phe
        355                 360                 365
Lys Glu Val Gln Gln Asn Arg Glu Trp Phe Ile Ile Thr Leu Tyr Gly
    370                 375                 380
Arg Thr Lys Glu Leu Thr Ser Lys Leu Lys Glu Asn Phe Ile Arg Phe
385                 390                 395                 400
Ser Lys Ser Leu Gly Leu Pro Glu Asn His Ile Val Phe Pro Val Pro
                405                 410                 415
```

```
Ile Asp Gln Cys Ile Asp Gly Ser Ser Ala Gly Pro Gly Glu Val Gln
                420                 425                 430

Leu Val Glu Ser Gly Gly Gly Leu Val Gln Pro Gly Gly Ser Leu Arg
            435                 440                 445

Leu Ser Cys Ala Ala Ser Gly Tyr Thr Phe Thr Arg Tyr Thr Met His
        450                 455                 460

Trp Val Arg Gln Ser Pro Gly Lys Gly Leu Glu Trp Val Ala Tyr Ile
465                 470                 475                 480

Asn Pro Ser Arg Gly Tyr Thr Asn Tyr Ala Asp Ser Val Lys Gly Arg
                485                 490                 495

Phe Thr Ile Ser Ala Asp Lys Ser Lys Asn Thr Ala Tyr Leu Gln Met
            500                 505                 510

Asn Ser Leu Arg Ala Glu Asp Thr Ala Ile Tyr Tyr Cys Ser Arg Tyr
        515                 520                 525

Tyr Asp Asp His Tyr Cys Leu Asp Tyr Trp Gly Gln Gly Thr Leu Val
530                 535                 540

Thr Val Ser Ser Ala Ser Thr Lys Gly Pro Ser Val Phe Pro Leu Ala
545                 550                 555                 560

Pro Ser Ser Lys Ser Thr Ser Gly Gly Thr Ala Ala Leu Gly Cys Leu
                565                 570                 575

Val Lys Asp Tyr Phe Pro Glu Pro Val Thr Val Ser Trp Asn Ser Gly
            580                 585                 590

Ala Leu Thr Ser Gly Val His Thr Phe Pro Ala Val Leu Gln Ser Ser
        595                 600                 605

Gly Leu Tyr Ser Leu Ser Ser Val Val Thr Val Pro Ser Ser Ser Leu
            610                 615                 620

Gly Thr Gln Thr Tyr Ile Cys Asn Val Asn His Lys Pro Ser Asn Thr
625                 630                 635                 640

Lys Val Asp Lys Lys Val Glu Pro Lys Ser Cys Asp Lys Thr His Thr
                645                 650                 655

<210> SEQ ID NO 36
<211> LENGTH: 546
<212> TYPE: PRT
<213> ORGANISM: Artificial sequence
<220> FEATURE:
<223> OTHER INFORMATION: Synthetic polypeptide

<400> SEQUENCE: 36

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
            Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
            145                 150                 155                 160

Glu Ser Val Thr Glu Gln Asp Ser Lys Asp Ser Thr Tyr Ser Leu Ser
                            165                 170                 175

Ser Thr Leu Thr Leu Ser Lys Ala Asp Tyr Glu Lys His Lys Val Tyr
                        180                 185                 190

Ala Cys Glu Val Thr His Gln Gly Leu Ser Ser Pro Val Thr Lys Ser
                    195                 200                 205

Phe Asn Arg Gly Glu Cys Gly Gly Ala Gly Gly Ser Thr Ser Thr Ser
                210                 215                 220

Ser Ser Ser Gly Ser Ser Val Val Asp Asn Lys Phe Asn Lys Glu Arg
            225                 230                 235                 240

Tyr Leu Ala Tyr Tyr Glu Ile Trp Gln Leu Pro Asn Leu Asn Arg Thr
                            245                 250                 255

Gln Lys Ala Ala Phe Ile Gly Ser Leu Gln Asp Asp Pro Ser Gln Ser
                        260                 265                 270

Ala Asn Leu Leu Ala Glu Ala Lys Lys Leu Asn Asp Ala Gln Ala Pro
                    275                 280                 285

Lys Gly Gly Ser Gly Arg Leu Ile Glu Asp Ile Cys Leu Pro Arg Trp
                290                 295                 300

Gly Cys Leu Trp Glu Asp Asp Ser Ser Gly Ser Ser Gly Ser Ser Gly
            305                 310                 315                 320

Ser Ser Gly Glu Val Gln Leu Val Glu Ser Gly Gly Gly Leu Val Gln
                            325                 330                 335

Pro Gly Gly Ser Leu Arg Leu Ser Cys Ala Ala Ser Gly Phe Asn Ile
                        340                 345                 350

Lys Asp Thr Tyr Ile His Trp Val Arg Gln Ser Pro Gly Lys Gly Leu
                    355                 360                 365

Glu Trp Val Ala Arg Ile Tyr Pro Thr Asn Gly Tyr Thr Arg Tyr Ala
                370                 375                 380

Asp Ser Val Lys Gly Arg Phe Thr Ile Ser Ala Asp Thr Ser Lys Asn
            385                 390                 395                 400

Thr Ala Tyr Leu Gln Met Asn Ser Leu Arg Ala Glu Asp Thr Ala Ile
                            405                 410                 415

Tyr Tyr Cys Ser Arg Trp Gly Asp Gly Phe Tyr Ala Met Asp Tyr
                        420                 425                 430

Trp Gly Gln Gly Thr Leu Val Thr Val Ser Ser Ala Ser Thr Lys Gly
                    435                 440                 445

Pro Ser Val Phe Pro Leu Ala Pro Ser Ser Lys Ser Thr Ser Gly Gly
                450                 455                 460

Thr Ala Ala Leu Gly Cys Leu Val Lys Asp Tyr Phe Pro Glu Pro Val
            465                 470                 475                 480

Thr Val Ser Trp Asn Ser Gly Ala Leu Thr Ser Gly Val His Thr Phe
                            485                 490                 495

Pro Ala Val Leu Gln Ser Ser Gly Leu Tyr Ser Leu Ser Ser Val Val
                        500                 505                 510

Thr Val Pro Ser Ser Ser Leu Gly Thr Gln Thr Tyr Ile Cys Asn Val
                    515                 520                 525

Asn His Lys Pro Ser Asn Thr Lys Val Asp Lys Lys Val Glu Pro Lys
                530                 535                 540
```

-continued

Ser Cys
545

<210> SEQ ID NO 37
<211> LENGTH: 810
<212> TYPE: PRT
<213> ORGANISM: Artificial sequence
<220> FEATURE:
<223> OTHER INFORMATION: Synthetic polypeptide

<400> SEQUENCE: 37

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Arg Thr Asn Gly Ser Pro Arg Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Glu Ala Asp Tyr Tyr Cys Gln Gln Ser Tyr Ser Thr Pro Pro
                85                  90                  95

Ile Thr Phe Gly Ala Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Ser Ser Ala Ser Gly Ser Thr Ser Thr
210                 215                 220

Ser Gly Ser Ser Ala Ser Ser Gly Gly Gln Val Gln Leu Gln Glu
225                 230                 235                 240

Ser Gly Gly Gly Ser Val Gln Ala Gly Ser Leu Lys Leu Thr Cys
                245                 250                 255

Ala Ala Ser Gly Tyr Ile Phe Asn Ser Cys Gly Met Gly Trp Tyr Arg
            260                 265                 270

Gln Ser Pro Gly Arg Glu Arg Glu Leu Val Ser Arg Ile Ser Gly Asp
        275                 280                 285

Gly Asp Thr Trp His Lys Glu Ser Val Lys Gly Arg Phe Thr Ile Ser
290                 295                 300

Gln Asp Asn Val Lys Lys Thr Leu Tyr Leu Gln Met Asn Ser Leu Lys
305                 310                 315                 320

Pro Glu Asp Thr Ala Val Tyr Phe Cys Ala Val Cys Tyr Asn Leu Glu
                325                 330                 335

Thr Tyr Trp Gly Gln Gly Thr Gln Val Thr Val Ser Ser Ala Ser Gly
            340                 345                 350
```

```
Ala Gly Ala Ser Glu Val Gln Leu Val Glu Ser Gly Gly Leu Val
            355                 360                 365
Gln Pro Gly Arg Ser Leu Arg Leu Ser Cys Ala Ala Ser Gly Phe Thr
370                 375                 380
Phe Ala Asp Tyr Thr Met His Trp Val Arg Gln Ala Pro Gly Lys Gly
385                 390                 395                 400
Leu Glu Trp Val Ser Asp Ile Ser Trp Asn Ser Gly Ser Ile Ala Tyr
                405                 410                 415
Ala Asp Ser Val Lys Gly Arg Phe Thr Ile Ser Arg Asp Asn Ala Lys
            420                 425                 430
Asn Ser Leu Tyr Leu Gln Met Asn Ser Leu Arg Thr Glu Asp Thr Ala
            435                 440                 445
Ile Tyr Tyr Cys Ala Lys Asp Ser Arg Gly Tyr Gly His Tyr Lys Tyr
        450                 455                 460
Leu Gly Leu Asp Val Trp Gly Gln Gly Thr Thr Val Thr Val Ser Ser
465                 470                 475                 480
Ala Ser Thr Lys Gly Pro Ser Val Phe Pro Leu Ala Pro Ser Ser Lys
                485                 490                 495
Ser Thr Ser Gly Gly Thr Ala Ala Leu Gly Cys Leu Val Lys Asp Tyr
            500                 505                 510
Phe Pro Glu Pro Val Thr Val Ser Trp Asn Ser Gly Ala Leu Thr Ser
        515                 520                 525
Gly Val His Thr Phe Pro Ala Val Leu Gln Ser Ser Gly Leu Tyr Ser
        530                 535                 540
Leu Ser Ser Val Val Thr Val Pro Ser Ser Leu Gly Thr Gln Thr
545                 550                 555                 560
Tyr Ile Cys Asn Val Asn His Lys Pro Ser Asn Thr Lys Val Asp Lys
                565                 570                 575
Lys Val Glu Pro Lys Ser Cys Asp Lys Thr His Thr Cys Pro Pro Cys
            580                 585                 590
Pro Ala Pro Glu Leu Leu Gly Gly Pro Ser Val Phe Leu Phe Pro Pro
        595                 600                 605
Lys Pro Lys Asp Thr Leu Met Ile Ser Arg Thr Pro Glu Val Thr Cys
610                 615                 620
Val Val Val Asp Val Ser His Glu Asp Pro Glu Val Lys Phe Asn Trp
625                 630                 635                 640
Tyr Val Asp Gly Val Glu Val His Asn Ala Lys Thr Lys Pro Arg Glu
                645                 650                 655
Glu Gln Tyr Asn Ser Thr Tyr Arg Val Val Ser Val Leu Thr Val Leu
            660                 665                 670
His Gln Asp Trp Leu Asn Gly Lys Glu Tyr Lys Cys Lys Val Ser Asn
        675                 680                 685
Lys Ala Leu Pro Ala Pro Ile Glu Lys Thr Ile Ser Lys Ala Lys Gly
        690                 695                 700
Gln Pro Arg Glu Pro Gln Val Tyr Thr Leu Pro Pro Ser Arg Asp Glu
705                 710                 715                 720
Leu Thr Lys Asn Gln Val Ser Leu Thr Cys Leu Val Lys Gly Phe Tyr
                725                 730                 735
Pro Ser Asp Ile Ala Val Glu Trp Glu Ser Asn Gly Gln Pro Glu Asn
            740                 745                 750
Asn Tyr Lys Thr Thr Pro Pro Val Leu Asp Ser Asp Gly Ser Phe Phe
        755                 760                 765
Leu Tyr Ser Lys Leu Thr Val Asp Lys Ser Arg Trp Gln Gln Gly Asn
```

```
              770                 775                 780
Val Phe Ser Cys Ser Val Met His Glu Ala Leu His Asn His Tyr Thr
785                 790                 795                 800

Gln Lys Ser Leu Ser Leu Ser Pro Gly Lys
                805                 810

<210> SEQ ID NO 38
<211> LENGTH: 587
<212> TYPE: PRT
<213> ORGANISM: Artificial sequence
<220> FEATURE:
<223> OTHER INFORMATION: Synthetic polypeptide

<400> SEQUENCE: 38

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Arg Thr Asn Gly Ser Pro Arg Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Glu Ala Asp Tyr Tyr Cys Gln Gln Ser Tyr Ser Thr Pro Pro
                85                  90                  95

Ile Thr Phe Gly Ala Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Ser Ser Ala Ser Gly Ser Thr Ser Thr
210                 215                 220

Ser Gly Ser Ser Ala Ser Ser Gly Gly Gln Val Gln Leu Gln Glu
225                 230                 235                 240

Ser Gly Gly Gly Ser Val Gln Ala Gly Ser Leu Lys Leu Thr Cys
                245                 250                 255

Ala Ala Ser Gly Tyr Ile Phe Asn Ser Cys Gly Met Gly Trp Tyr Arg
            260                 265                 270

Gln Ser Pro Gly Arg Glu Arg Glu Leu Val Ser Arg Ile Ser Gly Asp
        275                 280                 285

Gly Asp Thr Trp His Lys Glu Ser Val Lys Gly Arg Phe Thr Ile Ser
            290                 295                 300

Gln Asp Asn Val Lys Lys Thr Leu Tyr Leu Gln Met Asn Ser Leu Lys
305                 310                 315                 320

Pro Glu Asp Thr Ala Val Tyr Phe Cys Ala Val Cys Tyr Asn Leu Glu
```

```
              325                 330                 335
Thr Tyr Trp Gly Gln Gly Thr Gln Val Thr Val Ser Ser Ala Ser Gly
            340                 345                 350

Ala Gly Ala Ser Glu Val Gln Leu Val Glu Ser Gly Gly Gly Leu Val
            355                 360                 365

Gln Pro Gly Arg Ser Leu Arg Leu Ser Cys Ala Ala Ser Gly Phe Thr
        370                 375                 380

Phe Ala Asp Tyr Thr Met His Trp Val Arg Gln Ala Pro Gly Lys Gly
385                 390                 395                 400

Leu Glu Trp Val Ser Asp Ile Ser Trp Asn Ser Gly Ser Ile Ala Tyr
                405                 410                 415

Ala Asp Ser Val Lys Gly Arg Phe Thr Ile Ser Arg Asp Asn Ala Lys
            420                 425                 430

Asn Ser Leu Tyr Leu Gln Met Asn Ser Leu Arg Thr Glu Asp Thr Ala
        435                 440                 445

Ile Tyr Tyr Cys Ala Lys Asp Ser Arg Gly Tyr Gly His Tyr Lys Tyr
450                 455                 460

Leu Gly Leu Asp Val Trp Gly Gln Gly Thr Thr Val Thr Val Ser Ser
465                 470                 475                 480

Ala Ser Thr Lys Gly Pro Ser Val Phe Pro Leu Ala Pro Ser Ser Lys
                485                 490                 495

Ser Thr Ser Gly Gly Thr Ala Ala Leu Gly Cys Leu Val Lys Asp Tyr
            500                 505                 510

Phe Pro Glu Pro Val Thr Val Ser Trp Asn Ser Gly Ala Leu Thr Ser
        515                 520                 525

Gly Val His Thr Phe Pro Ala Val Leu Gln Ser Ser Gly Leu Tyr Ser
    530                 535                 540

Leu Ser Ser Val Val Thr Val Pro Ser Ser Ser Leu Gly Thr Gln Thr
545                 550                 555                 560

Tyr Ile Cys Asn Val Asn His Lys Pro Ser Asn Thr Lys Val Asp Lys
                565                 570                 575

Lys Val Glu Pro Lys Ser Cys Asp Lys Thr His
            580                 585

<210> SEQ ID NO 39
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 39

Gly Gly Ser Gly Val Pro Leu Ser Leu Tyr Ser Gly Gly
1               5                   10

<210> SEQ ID NO 40
<211> LENGTH: 677
<212> TYPE: PRT
<213> ORGANISM: Artificial sequence
<220> FEATURE:
<223> OTHER INFORMATION: Synthetic polypeptide

<400> SEQUENCE: 40

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30
```

```
Val Ala Trp Tyr Gln Gln Arg Thr Asn Gly Ser Pro Arg Leu Leu Ile
         35                  40                  45

Tyr Ser Ala Ser Phe Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65              70                  75                      80

Glu Asp Ile Ala Asp Tyr Tyr Cys Gln Gln His Tyr Thr Thr Pro Pro
                 85                  90                  95

Thr Phe Gly Ala Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
             165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys Asp Lys Thr His Thr Cys Pro Pro Cys Pro
     210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
             245                 250                 255

Val Val Asp Val Ser His Glu Asp Pro Glu Val Lys Phe Asn Trp Tyr
         260                 265                 270

Val Asp Gly Val Glu Val His Asn Ala Lys Thr Lys Pro Arg Glu Glu
     275                 280                 285

Gln Tyr Asn Ser Thr Tyr Arg Val Val Ser Val Leu Thr Val Leu His
     290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
             325                 330                 335

Pro Arg Glu Pro Gln Val Tyr Thr Leu Pro Pro Ser Arg Asp Glu Leu
         340                 345                 350

Thr Lys Asn Gln Val Ser Leu Thr Cys Leu Val Lys Gly Phe Tyr Pro
     355                 360                 365

Ser Asp Ile Ala Val Glu Trp Glu Ser Asn Gly Gln Pro Glu Asn Asn
     370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
             405                 410                 415

Phe Ser Cys Ser Val Met His Glu Ala Leu His Asn His Tyr Thr Gln
         420                 425                 430

Lys Ser Leu Ser Leu Ser Pro Gly Lys Gly Gly Ser Gly Val Pro Leu
     435                 440                 445

Ser Leu Tyr Ser Gly Gly Glu Val Gln Leu Val Glu Ser Gly Gly Gly
```

Leu Val Gln Pro Gly Gly Ser Leu Arg Leu Ser Cys Ala Ala Ser Gly
465                 470                 475                 480

Phe Asn Ile Lys Asp Thr Tyr Ile His Trp Val Arg Gln Ser Pro Gly
                485                 490                 495

Lys Gly Leu Glu Trp Val Ala Arg Ile Tyr Pro Thr Asn Gly Tyr Thr
                500                 505                 510

Arg Tyr Ala Asp Ser Val Lys Gly Arg Phe Thr Ile Ser Ala Asp Thr
        515                 520                 525

Ser Lys Asn Thr Ala Tyr Leu Gln Met Asn Ser Leu Arg Ala Glu Asp
        530                 535                 540

Thr Ala Ile Tyr Tyr Cys Ser Arg Trp Gly Gly Asp Gly Phe Tyr Ala
545                 550                 555                 560

Met Asp Tyr Trp Gly Gln Gly Thr Leu Val Thr Val Ser Ser Ala Ser
                565                 570                 575

Thr Lys Gly Pro Ser Val Phe Pro Leu Ala Pro Ser Ser Lys Ser Thr
                580                 585                 590

Ser Gly Gly Thr Ala Ala Leu Gly Cys Leu Val Lys Asp Tyr Phe Pro
        595                 600                 605

Glu Pro Val Thr Val Ser Trp Asn Ser Gly Ala Leu Thr Ser Gly Val
        610                 615                 620

His Thr Phe Pro Ala Val Leu Gln Ser Ser Gly Leu Tyr Ser Leu Ser
625                 630                 635                 640

Ser Val Val Thr Val Pro Ser Ser Ser Leu Gly Thr Gln Thr Tyr Ile
                645                 650                 655

Cys Asn Val Asn His Lys Pro Ser Asn Thr Lys Val Asp Lys Lys Val
                660                 665                 670

Glu Pro Lys Ser Cys
            675

<210> SEQ ID NO 41
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 41

Gly Ser Gly Ser Ala Asn Gln Leu Lys Gly Ser Ser Gly
1               5                   10

<210> SEQ ID NO 42
<211> LENGTH: 677
<212> TYPE: PRT
<213> ORGANISM: Artificial sequence
<220> FEATURE:
<223> OTHER INFORMATION: Synthetic polypeptide

<400> SEQUENCE: 42

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

```
Ser Arg Ser Gly Thr Asp Phe Thr Leu Thr Ile Ser Ser Leu Gln Pro
 65                  70                  75                  80

Glu Asp Ile Ala Asp Tyr Tyr Cys Gln Gln His Tyr Thr Thr Pro Pro
             85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys Gly Ser Gly Ser Ala Asn Gln
        435                 440                 445

Leu Lys Gly Ser Ser Gly Glu Val Gln Leu Val Glu Ser Gly Gly Gly
        450                 455                 460

Leu Val Gln Pro Gly Gly Ser Leu Arg Leu Ser Cys Ala Ala Ser Gly
465                 470                 475                 480

Phe Asn Ile Lys Asp Thr Tyr Ile His Trp Val Arg Gln Ser Pro Gly
```

```
                        485                 490                 495
Lys Gly Leu Glu Trp Val Ala Arg Ile Tyr Pro Thr Asn Gly Tyr Thr
            500                 505                 510

Arg Tyr Ala Asp Ser Val Lys Gly Arg Phe Thr Ile Ser Ala Asp Thr
        515                 520                 525

Ser Lys Asn Thr Ala Tyr Leu Gln Met Asn Ser Leu Arg Ala Glu Asp
    530                 535                 540

Thr Ala Ile Tyr Tyr Cys Ser Arg Trp Gly Gly Asp Gly Phe Tyr Ala
545                 550                 555                 560

Met Asp Tyr Trp Gly Gln Gly Thr Leu Val Thr Val Ser Ser Ala Ser
                565                 570                 575

Thr Lys Gly Pro Ser Val Phe Pro Leu Ala Pro Ser Ser Lys Ser Thr
            580                 585                 590

Ser Gly Gly Thr Ala Ala Leu Gly Cys Leu Val Lys Asp Tyr Phe Pro
        595                 600                 605

Glu Pro Val Thr Val Ser Trp Asn Ser Gly Ala Leu Thr Ser Gly Val
    610                 615                 620

His Thr Phe Pro Ala Val Leu Gln Ser Ser Gly Leu Tyr Ser Leu Ser
625                 630                 635                 640

Ser Val Val Thr Val Pro Ser Ser Ser Leu Gly Thr Gln Thr Tyr Ile
                645                 650                 655

Cys Asn Val Asn His Lys Pro Ser Asn Thr Lys Val Asp Lys Lys Val
            660                 665                 670

Glu Pro Lys Ser Cys
        675

<210> SEQ ID NO 43
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 43

Gly Ser Ser Asp Ser Gly Gly Phe Met Leu Thr Ser Gly
1               5                   10

<210> SEQ ID NO 44
<211> LENGTH: 677
<212> TYPE: PRT
<213> ORGANISM: Artificial sequence
<220> FEATURE:
<223> OTHER INFORMATION: Synthetic polypeptide

<400> SEQUENCE: 44

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95
```

```
Thr Phe Gly Ala Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys Gly Ser Ser Asp Ser Gly Gly
        435                 440                 445

Phe Met Leu Thr Ser Gly Glu Val Gln Leu Val Glu Ser Gly Gly Gly
450                 455                 460

Leu Val Gln Pro Gly Gly Ser Leu Arg Leu Ser Cys Ala Ala Ser Gly
465                 470                 475                 480

Phe Asn Ile Lys Asp Thr Tyr Ile His Trp Val Arg Gln Ser Pro Gly
                485                 490                 495

Lys Gly Leu Glu Trp Val Ala Arg Ile Tyr Pro Thr Asn Gly Tyr Thr
            500                 505                 510

Arg Tyr Ala Asp Ser Val Lys Gly Arg Phe Thr Ile Ser Ala Asp Thr
```

```
                515                 520                 525
Ser Lys Asn Thr Ala Tyr Leu Gln Met Asn Ser Leu Arg Ala Glu Asp
    530                 535                 540

Thr Ala Ile Tyr Tyr Cys Ser Arg Trp Gly Gly Asp Gly Phe Tyr Ala
545                 550                 555                 560

Met Asp Tyr Trp Gly Gln Gly Thr Leu Val Thr Val Ser Ser Ala Ser
                565                 570                 575

Thr Lys Gly Pro Ser Val Phe Pro Leu Ala Pro Ser Ser Lys Ser Thr
            580                 585                 590

Ser Gly Gly Thr Ala Ala Leu Gly Cys Leu Val Lys Asp Tyr Phe Pro
            595                 600                 605

Glu Pro Val Thr Val Ser Trp Asn Ser Gly Ala Leu Thr Ser Gly Val
        610                 615                 620

His Thr Phe Pro Ala Val Leu Gln Ser Ser Gly Leu Tyr Ser Leu Ser
625                 630                 635                 640

Ser Val Val Thr Val Pro Ser Ser Ser Leu Gly Thr Gln Thr Tyr Ile
                645                 650                 655

Cys Asn Val Asn His Lys Pro Ser Asn Thr Lys Val Asp Lys Lys Val
            660                 665                 670

Glu Pro Lys Ser Cys
        675

<210> SEQ ID NO 45
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 45

Gly Ser Gly Ser His Glu Gln Leu Thr Val Ser Ser Gly
1               5                   10

<210> SEQ ID NO 46
<211> LENGTH: 677
<212> TYPE: PRT
<213> ORGANISM: Artificial sequence
<220> FEATURE:
<223> OTHER INFORMATION: Synthetic polypeptide

<400> SEQUENCE: 46

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

-continued

```
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Asp Lys Thr His Thr Cys Pro Pro Cys Pro
210                 215                 220
Ala Pro Glu Leu Leu Gly Gly Pro Ser Val Phe Leu Phe Pro Pro Lys
225                 230                 235                 240
Pro Lys Asp Thr Leu Met Ile Ser Arg Thr Pro Glu Val Thr Cys Val
                245                 250                 255
Val Val Asp Val Ser His Glu Asp Pro Glu Val Lys Phe Asn Trp Tyr
            260                 265                 270
Val Asp Gly Val Glu Val His Asn Ala Lys Thr Lys Pro Arg Glu Glu
        275                 280                 285
Gln Tyr Asn Ser Thr Tyr Arg Val Val Ser Val Leu Thr Val Leu His
    290                 295                 300
Gln Asp Trp Leu Asn Gly Lys Glu Tyr Lys Cys Lys Val Ser Asn Lys
305                 310                 315                 320
Ala Leu Pro Ala Pro Ile Glu Lys Thr Ile Ser Lys Ala Lys Gly Gln
                325                 330                 335
Pro Arg Glu Pro Gln Val Tyr Thr Leu Pro Pro Ser Arg Asp Glu Leu
            340                 345                 350
Thr Lys Asn Gln Val Ser Leu Thr Cys Leu Val Lys Gly Phe Tyr Pro
        355                 360                 365
Ser Asp Ile Ala Val Glu Trp Glu Ser Asn Gly Gln Pro Glu Asn Asn
    370                 375                 380
Tyr Lys Thr Thr Pro Pro Val Leu Asp Ser Asp Gly Ser Phe Phe Leu
385                 390                 395                 400
Tyr Ser Lys Leu Thr Val Asp Lys Ser Arg Trp Gln Gln Gly Asn Val
                405                 410                 415
Phe Ser Cys Ser Val Met His Glu Ala Leu His Asn His Tyr Thr Gln
            420                 425                 430
Lys Ser Leu Ser Leu Ser Pro Gly Lys Gly Ser Gly Ser His Glu Gln
        435                 440                 445
Leu Thr Val Ser Ser Gly Glu Val Gln Leu Val Glu Ser Gly Gly Gly
    450                 455                 460
Leu Val Gln Pro Gly Gly Ser Leu Arg Leu Ser Cys Ala Ala Ser Gly
465                 470                 475                 480
Phe Asn Ile Lys Asp Thr Tyr Ile His Trp Val Arg Gln Ser Pro Gly
                485                 490                 495
Lys Gly Leu Glu Trp Val Ala Arg Ile Tyr Pro Thr Asn Gly Tyr Thr
            500                 505                 510
Arg Tyr Ala Asp Ser Val Lys Gly Arg Phe Thr Ile Ser Ala Asp Thr
        515                 520                 525
Ser Lys Asn Thr Ala Tyr Leu Gln Met Asn Ser Leu Arg Ala Glu Asp
    530                 535                 540
Thr Ala Ile Tyr Tyr Cys Ser Arg Trp Gly Gly Asp Gly Phe Tyr Ala
```

```
                    545                 550                 555                 560
Met Asp Tyr Trp Gly Gln Gly Thr Leu Val Thr Val Ser Ser Ala Ser
                565                 570                 575

Thr Lys Gly Pro Ser Val Phe Pro Leu Ala Pro Ser Ser Lys Ser Thr
                580                 585                 590

Ser Gly Gly Thr Ala Ala Leu Gly Cys Leu Val Lys Asp Tyr Phe Pro
                595                 600                 605

Glu Pro Val Thr Val Ser Trp Asn Ser Gly Ala Leu Thr Ser Gly Val
            610                 615                 620

His Thr Phe Pro Ala Val Leu Gln Ser Ser Gly Leu Tyr Ser Leu Ser
625                 630                 635                 640

Ser Val Val Thr Val Pro Ser Ser Ser Leu Gly Thr Gln Thr Tyr Ile
                645                 650                 655

Cys Asn Val Asn His Lys Pro Ser Asn Thr Lys Val Asp Lys Lys Val
                660                 665                 670

Glu Pro Lys Ser Cys
                675

<210> SEQ ID NO 47
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 47

Gly Ser Pro Ala Pro Gly Val Tyr Pro Gly Pro Ser Gly
1               5                   10

<210> SEQ ID NO 48
<211> LENGTH: 677
<212> TYPE: PRT
<213> ORGANISM: Artificial sequence
<220> FEATURE:
<223> OTHER INFORMATION: Synthetic polypeptide

<400> SEQUENCE: 48

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Arg Thr Asn Gly Ser Pro Arg Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Asp Lys Thr His Thr Cys Pro Pro Cys Pro
    210                 215                 220
Ala Pro Glu Leu Leu Gly Gly Pro Ser Val Phe Leu Phe Pro Pro Lys
225                 230                 235                 240
Pro Lys Asp Thr Leu Met Ile Ser Arg Thr Pro Glu Val Thr Cys Val
                245                 250                 255
Val Val Asp Val Ser His Glu Asp Pro Glu Val Lys Phe Asn Trp Tyr
            260                 265                 270
Val Asp Gly Val Glu Val His Asn Ala Lys Thr Lys Pro Arg Glu Glu
        275                 280                 285
Gln Tyr Asn Ser Thr Tyr Arg Val Val Ser Val Leu Thr Val Leu His
    290                 295                 300
Gln Asp Trp Leu Asn Gly Lys Glu Tyr Lys Cys Lys Val Ser Asn Lys
305                 310                 315                 320
Ala Leu Pro Ala Pro Ile Glu Lys Thr Ile Ser Lys Ala Lys Gly Gln
                325                 330                 335
Pro Arg Glu Pro Gln Val Tyr Thr Leu Pro Pro Ser Arg Asp Glu Leu
            340                 345                 350
Thr Lys Asn Gln Val Ser Leu Thr Cys Leu Val Lys Gly Phe Tyr Pro
        355                 360                 365
Ser Asp Ile Ala Val Glu Trp Glu Ser Asn Gly Gln Pro Glu Asn Asn
    370                 375                 380
Tyr Lys Thr Thr Pro Pro Val Leu Asp Ser Asp Gly Ser Phe Phe Leu
385                 390                 395                 400
Tyr Ser Lys Leu Thr Val Asp Lys Ser Arg Trp Gln Gln Gly Asn Val
                405                 410                 415
Phe Ser Cys Ser Val Met His Glu Ala Leu His Asn His Tyr Thr Gln
            420                 425                 430
Lys Ser Leu Ser Leu Ser Pro Gly Lys Gly Ser Pro Ala Pro Gly Val
        435                 440                 445
Tyr Pro Gly Pro Ser Gly Glu Val Gln Leu Val Glu Ser Gly Gly Gly
    450                 455                 460
Leu Val Gln Pro Gly Gly Ser Leu Arg Leu Ser Cys Ala Ala Ser Gly
465                 470                 475                 480
Phe Asn Ile Lys Asp Thr Tyr Ile His Trp Val Arg Gln Ser Pro Gly
                485                 490                 495
Lys Gly Leu Glu Trp Val Ala Arg Ile Tyr Pro Thr Asn Gly Tyr Thr
            500                 505                 510
Arg Tyr Ala Asp Ser Val Lys Gly Arg Phe Thr Ile Ser Ala Asp Thr
        515                 520                 525
Ser Lys Asn Thr Ala Tyr Leu Gln Met Asn Ser Leu Arg Ala Glu Asp
    530                 535                 540
Thr Ala Ile Tyr Tyr Cys Ser Arg Trp Gly Gly Asp Gly Phe Tyr Ala
545                 550                 555                 560
Met Asp Tyr Trp Gly Gln Gly Thr Leu Val Thr Val Ser Ser Ala Ser
                565                 570                 575
Thr Lys Gly Pro Ser Val Phe Pro Leu Ala Pro Ser Ser Lys Ser Thr
```

```
                580                 585                 590
Ser Gly Gly Thr Ala Ala Leu Gly Cys Leu Val Lys Asp Tyr Phe Pro
        595                 600                 605

Glu Pro Val Thr Val Ser Trp Asn Ser Gly Ala Leu Thr Ser Gly Val
        610                 615                 620

His Thr Phe Pro Ala Val Leu Gln Ser Ser Gly Leu Tyr Ser Leu Ser
625                 630                 635                 640

Ser Val Val Thr Val Pro Ser Ser Ser Leu Gly Thr Gln Thr Tyr Ile
                645                 650                 655

Cys Asn Val Asn His Lys Pro Ser Asn Thr Lys Val Asp Lys Lys Val
                660                 665                 670

Glu Pro Lys Ser Cys
        675

<210> SEQ ID NO 49
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 49

Gly Ser Gly Ser Gln Ser Gln Leu Lys Glu Ser Ser Gly
1               5                   10

<210> SEQ ID NO 50
<211> LENGTH: 677
<212> TYPE: PRT
<213> ORGANISM: Artificial sequence
<220> FEATURE:
<223> OTHER INFORMATION: Synthetic polypeptide

<400> SEQUENCE: 50

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

```
Ala Cys Glu Val Thr His Gln Gly Leu Ser Ser Pro Val Thr Lys Ser
            195                 200                 205

Phe Asn Arg Gly Glu Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys Gly Ser Gly Ser Gln Ser Gln
        435                 440                 445

Leu Lys Glu Ser Ser Gly Glu Val Gln Leu Val Glu Ser Gly Gly Gly
    450                 455                 460

Leu Val Gln Pro Gly Gly Ser Leu Arg Leu Ser Cys Ala Ala Ser Gly
465                 470                 475                 480

Phe Asn Ile Lys Asp Thr Tyr Ile His Trp Val Arg Gln Ser Pro Gly
                485                 490                 495

Lys Gly Leu Glu Trp Val Ala Arg Ile Tyr Pro Thr Asn Gly Tyr Thr
            500                 505                 510

Arg Tyr Ala Asp Ser Val Lys Gly Arg Phe Thr Ile Ser Ala Asp Thr
        515                 520                 525

Ser Lys Asn Thr Ala Tyr Leu Gln Met Asn Ser Leu Arg Ala Glu Asp
    530                 535                 540

Thr Ala Ile Tyr Tyr Cys Ser Arg Trp Gly Gly Asp Gly Phe Tyr Ala
545                 550                 555                 560

Met Asp Tyr Trp Gly Gln Gly Thr Leu Val Thr Val Ser Ser Ala Ser
                565                 570                 575

Thr Lys Gly Pro Ser Val Phe Pro Leu Ala Pro Ser Ser Lys Ser Thr
            580                 585                 590

Ser Gly Gly Thr Ala Ala Leu Gly Cys Leu Val Lys Asp Tyr Phe Pro
        595                 600                 605

Glu Pro Val Thr Val Ser Trp Asn Ser Gly Ala Leu Thr Ser Gly Val
```

-continued

His Thr Phe Pro Ala Val Leu Gln Ser Ser Gly Leu Tyr Ser Leu Ser
625                 630                 635                 640

Ser Val Val Thr Val Pro Ser Ser Leu Gly Thr Gln Thr Tyr Ile
            645                 650                 655

Cys Asn Val Asn His Lys Pro Ser Asn Thr Lys Val Asp Lys Val
            660                 665                 670

Glu Pro Lys Ser Cys
        675

<210> SEQ ID NO 51
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 51

Gly Ser Ser Arg Ala Ala Ala Val Lys Ser Pro Ser Gly
1               5                   10

<210> SEQ ID NO 52
<211> LENGTH: 677
<212> TYPE: PRT
<213> ORGANISM: Artificial sequence
<220> FEATURE:
<223> OTHER INFORMATION: Synthetic polypeptide

<400> SEQUENCE: 52

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

-continued

```
Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Lys Phe Asn Trp Tyr
        260                 265                 270

Val Asp Gly Val Glu Val His Asn Ala Lys Thr Lys Pro Arg Glu Glu
    275                 280                 285

Gln Tyr Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
            325                 330                 335

Pro Arg Glu Pro Gln Val Tyr Thr Leu Pro Pro Ser Arg Asp Glu Leu
        340                 345                 350

Thr Lys Asn Gln Val Ser Leu Thr Cys Leu Val Lys Gly Phe Tyr Pro
    355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
        420                 425                 430

Lys Ser Leu Ser Leu Ser Pro Gly Lys Gly Ser Ser Arg Ala Ala Ala
    435                 440                 445

Val Lys Ser Pro Ser Gly Glu Val Gln Leu Val Glu Ser Gly Gly Gly
    450                 455                 460

Leu Val Gln Pro Gly Gly Ser Leu Arg Leu Ser Cys Ala Ala Ser Gly
465                 470                 475                 480

Phe Asn Ile Lys Asp Thr Tyr Ile His Trp Val Arg Gln Ser Pro Gly
            485                 490                 495

Lys Gly Leu Glu Trp Val Ala Arg Ile Tyr Pro Thr Asn Gly Tyr Thr
        500                 505                 510

Arg Tyr Ala Asp Ser Val Lys Gly Arg Phe Thr Ile Ser Ala Asp Thr
    515                 520                 525

Ser Lys Asn Thr Ala Tyr Leu Gln Met Asn Ser Leu Arg Ala Glu Asp
530                 535                 540

Thr Ala Ile Tyr Tyr Cys Ser Arg Trp Gly Gly Asp Gly Phe Tyr Ala
545                 550                 555                 560

Met Asp Tyr Trp Gly Gln Gly Thr Leu Val Thr Val Ser Ser Ala Ser
            565                 570                 575

Thr Lys Gly Pro Ser Val Phe Pro Leu Ala Pro Ser Ser Lys Ser Thr
        580                 585                 590

Ser Gly Gly Thr Ala Ala Leu Gly Cys Leu Val Lys Asp Tyr Phe Pro
    595                 600                 605

Glu Pro Val Thr Val Ser Trp Asn Ser Gly Ala Leu Thr Ser Gly Val
    610                 615                 620

His Thr Phe Pro Ala Val Leu Gln Ser Ser Gly Leu Tyr Ser Leu Ser
625                 630                 635                 640

Ser Val Val Thr Val Pro Ser Ser Ser Leu Gly Thr Gln Thr Tyr Ile
```

```
            645                 650                 655
Cys Asn Val Asn His Lys Pro Ser Asn Thr Lys Val Asp Lys Lys Val
                660                 665                 670

Glu Pro Lys Ser Cys
        675
```

<210> SEQ ID NO 53
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 53

```
Gly Ser Ser Thr Ser Val Leu Met Ala Ala Pro Ser Gly
1               5                   10
```

<210> SEQ ID NO 54
<211> LENGTH: 677
<212> TYPE: PRT
<213> ORGANISM: Artificial sequence
<220> FEATURE:
<223> OTHER INFORMATION: Synthetic polypeptide

<400> SEQUENCE: 54

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Arg Thr Asn Gly Ser Pro Arg Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255
```

-continued

```
Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys Gly Ser Ser Thr Ser Val Leu
        435                 440                 445

Met Ala Ala Pro Ser Gly Glu Val Gln Leu Val Glu Ser Gly Gly Gly
    450                 455                 460

Leu Val Gln Pro Gly Gly Ser Leu Arg Leu Ser Cys Ala Ala Ser Gly
465                 470                 475                 480

Phe Asn Ile Lys Asp Thr Tyr Ile His Trp Val Arg Gln Ser Pro Gly
                485                 490                 495

Lys Gly Leu Glu Trp Val Ala Arg Ile Tyr Pro Thr Asn Gly Tyr Thr
            500                 505                 510

Arg Tyr Ala Asp Ser Val Lys Gly Arg Phe Thr Ile Ser Ala Asp Thr
        515                 520                 525

Ser Lys Asn Thr Ala Tyr Leu Gln Met Asn Ser Leu Arg Ala Glu Asp
    530                 535                 540

Thr Ala Ile Tyr Tyr Cys Ser Arg Trp Gly Gly Asp Gly Phe Tyr Ala
545                 550                 555                 560

Met Asp Tyr Trp Gly Gln Gly Thr Leu Val Thr Val Ser Ser Ala Ser
                565                 570                 575

Thr Lys Gly Pro Ser Val Phe Pro Leu Ala Pro Ser Ser Lys Ser Thr
            580                 585                 590

Ser Gly Gly Thr Ala Ala Leu Gly Cys Leu Val Lys Asp Tyr Phe Pro
        595                 600                 605

Glu Pro Val Thr Val Ser Trp Asn Ser Gly Ala Leu Thr Ser Gly Val
    610                 615                 620

His Thr Phe Pro Ala Val Leu Gln Ser Ser Gly Leu Tyr Ser Leu Ser
625                 630                 635                 640

Ser Val Val Thr Val Pro Ser Ser Ser Leu Gly Thr Gln Thr Tyr Ile
                645                 650                 655

Cys Asn Val Asn His Lys Pro Ser Asn Thr Lys Val Asp Lys Lys Val
            660                 665                 670

Glu Pro Lys Ser Cys
```

<210> SEQ ID NO 55
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 55

Gly Ser Ser Val Ala Asn Leu Leu Tyr Glu Ser Ser Gly
1               5                   10

<210> SEQ ID NO 56
<211> LENGTH: 677
<212> TYPE: PRT
<213> ORGANISM: Artificial sequence
<220> FEATURE:
<223> OTHER INFORMATION: Synthetic polypeptide

<400> SEQUENCE: 56

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

```
Gln Tyr Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
            325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
            420                 425                 430

Lys Ser Leu Ser Leu Ser Pro Gly Lys Gly Ser Ser Val Ala Asn Leu
435                 440                 445

Leu Tyr Glu Ser Ser Gly Glu Val Gln Leu Val Glu Ser Gly Gly Gly
450                 455                 460

Leu Val Gln Pro Gly Gly Ser Leu Arg Leu Ser Cys Ala Ala Ser Gly
465                 470                 475                 480

Phe Asn Ile Lys Asp Thr Tyr Ile His Trp Val Arg Gln Ser Pro Gly
            485                 490                 495

Lys Gly Leu Glu Trp Val Ala Arg Ile Tyr Pro Thr Asn Gly Tyr Thr
            500                 505                 510

Arg Tyr Ala Asp Ser Val Lys Gly Arg Phe Thr Ile Ser Ala Asp Thr
            515                 520                 525

Ser Lys Asn Thr Ala Tyr Leu Gln Met Asn Ser Leu Arg Ala Glu Asp
530                 535                 540

Thr Ala Ile Tyr Tyr Cys Ser Arg Trp Gly Gly Asp Gly Phe Tyr Ala
545                 550                 555                 560

Met Asp Tyr Trp Gly Gln Gly Thr Leu Val Thr Val Ser Ser Ala Ser
            565                 570                 575

Thr Lys Gly Pro Ser Val Phe Pro Leu Ala Pro Ser Ser Lys Ser Thr
            580                 585                 590

Ser Gly Gly Thr Ala Ala Leu Gly Cys Leu Val Lys Asp Tyr Phe Pro
            595                 600                 605

Glu Pro Val Thr Val Ser Trp Asn Ser Gly Ala Leu Thr Ser Gly Val
610                 615                 620

His Thr Phe Pro Ala Val Leu Gln Ser Ser Gly Leu Tyr Ser Leu Ser
625                 630                 635                 640

Ser Val Val Thr Val Pro Ser Ser Ser Leu Gly Thr Gln Thr Tyr Ile
            645                 650                 655

Cys Asn Val Asn His Lys Pro Ser Asn Thr Lys Val Asp Lys Lys Val
            660                 665                 670

Glu Pro Lys Ser Cys
            675

<210> SEQ ID NO 57
<211> LENGTH: 13
<212> TYPE: PRT
```

```
<213> ORGANISM: Artificial sequence
<220> FEATURE:
<223> OTHER INFORMATION: Synthetic polypeptide

<400> SEQUENCE: 57

Gly Ser Gly Ser Val Gly Asn Leu Asn Phe Ser Ser Gly
1               5                   10

<210> SEQ ID NO 58
<211> LENGTH: 677
<212> TYPE: PRT
<213> ORGANISM: Artificial sequence
<220> FEATURE:
<223> OTHER INFORMATION: Synthetic polypeptide

<400> SEQUENCE: 58

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320
```

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys Gly Ser Gly Ser Val Gly Asn
        435                 440                 445

Leu Asn Phe Ser Ser Gly Glu Val Gln Leu Val Glu Ser Gly Gly Gly
450                 455                 460

Leu Val Gln Pro Gly Gly Ser Leu Arg Leu Ser Cys Ala Ala Ser Gly
465                 470                 475                 480

Phe Asn Ile Lys Asp Thr Tyr Ile His Trp Val Arg Gln Ser Pro Gly
                485                 490                 495

Lys Gly Leu Glu Trp Val Ala Arg Ile Tyr Pro Thr Asn Gly Tyr Thr
            500                 505                 510

Arg Tyr Ala Asp Ser Val Lys Gly Arg Phe Thr Ile Ser Ala Asp Thr
        515                 520                 525

Ser Lys Asn Thr Ala Tyr Leu Gln Met Asn Ser Leu Arg Ala Glu Asp
530                 535                 540

Thr Ala Ile Tyr Tyr Cys Ser Arg Trp Gly Gly Asp Gly Phe Tyr Ala
545                 550                 555                 560

Met Asp Tyr Trp Gly Gln Gly Thr Leu Val Thr Val Ser Ser Ala Ser
                565                 570                 575

Thr Lys Gly Pro Ser Val Phe Pro Leu Ala Pro Ser Ser Lys Ser Thr
            580                 585                 590

Ser Gly Gly Thr Ala Ala Leu Gly Cys Leu Val Lys Asp Tyr Phe Pro
        595                 600                 605

Glu Pro Val Thr Val Ser Trp Asn Ser Gly Ala Leu Thr Ser Gly Val
610                 615                 620

His Thr Phe Pro Ala Val Leu Gln Ser Ser Gly Leu Tyr Ser Leu Ser
625                 630                 635                 640

Ser Val Val Thr Val Pro Ser Ser Ser Leu Gly Thr Gln Thr Tyr Ile
                645                 650                 655

Cys Asn Val Asn His Lys Pro Ser Asn Thr Lys Val Asp Lys Lys Val
            660                 665                 670

Glu Pro Lys Ser Cys
            675

<210> SEQ ID NO 59
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 59

Gly Gly Ser Gly Gly Ser Gly Ser Ser Gly Gly
1               5                   10

<210> SEQ ID NO 60
<211> LENGTH: 677
<212> TYPE: PRT
<213> ORGANISM: Artificial sequence
<220> FEATURE:
<223> OTHER INFORMATION: Synthetic polypeptide

<400> SEQUENCE: 60

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys Gly Gly Ser Gly Gly Ser Ser
            435                 440                 445

Gly Ser Ser Ser Gly Gly Glu Val Gln Leu Val Glu Ser Gly Gly Gly
    450                 455                 460

Leu Val Gln Pro Gly Gly Ser Leu Arg Leu Ser Cys Ala Ala Ser Gly
465                 470                 475                 480

Phe Asn Ile Lys Asp Thr Tyr Ile His Trp Val Arg Gln Ser Pro Gly
                485                 490                 495

Lys Gly Leu Glu Trp Val Ala Arg Ile Tyr Pro Thr Asn Gly Tyr Thr
            500                 505                 510

Arg Tyr Ala Asp Ser Val Lys Gly Arg Phe Thr Ile Ser Ala Asp Thr
            515                 520                 525

Ser Lys Asn Thr Ala Tyr Leu Gln Met Asn Ser Leu Arg Ala Glu Asp
    530                 535                 540

Thr Ala Ile Tyr Tyr Cys Ser Arg Trp Gly Gly Asp Gly Phe Tyr Ala
545                 550                 555                 560

Met Asp Tyr Trp Gly Gln Gly Thr Leu Val Thr Val Ser Ser Ala Ser
            565                 570                 575

Thr Lys Gly Pro Ser Val Phe Pro Leu Ala Pro Ser Ser Lys Ser Thr
            580                 585                 590

Ser Gly Gly Thr Ala Ala Leu Gly Cys Leu Val Lys Asp Tyr Phe Pro
            595                 600                 605

Glu Pro Val Thr Val Ser Trp Asn Ser Gly Ala Leu Thr Ser Gly Val
    610                 615                 620

His Thr Phe Pro Ala Val Leu Gln Ser Ser Gly Leu Tyr Ser Leu Ser
625                 630                 635                 640

Ser Val Val Thr Val Pro Ser Ser Ser Leu Gly Thr Gln Thr Tyr Ile
                645                 650                 655

Cys Asn Val Asn His Lys Pro Ser Asn Thr Lys Val Asp Lys Lys Val
            660                 665                 670

Glu Pro Lys Ser Cys
            675

<210> SEQ ID NO 61
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 61

Gly Gly Ser Gly Val Pro Leu Ser Leu Tyr Ser Gly Gly Ser Ser Gly
1               5                   10                  15

<210> SEQ ID NO 62
<211> LENGTH: 680

```
<212> TYPE: PRT
<213> ORGANISM: Artificial sequence
<220> FEATURE:
<223> OTHER INFORMATION: Synthetic polypeptide

<400> SEQUENCE: 62

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380
```

Tyr Lys Thr Thr Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
        420                 425                 430

Lys Ser Leu Ser Leu Ser Pro Gly Lys Gly Gly Ser Gly Val Pro Leu
    435                 440                 445

Ser Leu Tyr Ser Gly Gly Ser Ser Gly Glu Val Gln Leu Val Glu Ser
    450                 455                 460

Gly Gly Gly Leu Val Gln Pro Gly Gly Ser Leu Arg Leu Ser Cys Ala
465                 470                 475                 480

Ala Ser Gly Phe Asn Ile Lys Asp Thr Tyr Ile His Trp Val Arg Gln
            485                 490                 495

Ser Pro Gly Lys Gly Leu Glu Trp Val Ala Arg Ile Tyr Pro Thr Asn
        500                 505                 510

Gly Tyr Thr Arg Tyr Ala Asp Ser Val Lys Gly Arg Phe Thr Ile Ser
    515                 520                 525

Ala Asp Thr Ser Lys Asn Thr Ala Tyr Leu Gln Met Asn Ser Leu Arg
530                 535                 540

Ala Glu Asp Thr Ala Ile Tyr Tyr Cys Ser Arg Trp Gly Gly Asp Gly
545                 550                 555                 560

Phe Tyr Ala Met Asp Tyr Trp Gly Gln Gly Thr Leu Val Thr Val Ser
            565                 570                 575

Ser Ala Ser Thr Lys Gly Pro Ser Val Phe Pro Leu Ala Pro Ser Ser
        580                 585                 590

Lys Ser Thr Ser Gly Gly Thr Ala Ala Leu Gly Cys Leu Val Lys Asp
    595                 600                 605

Tyr Phe Pro Glu Pro Val Thr Val Ser Trp Asn Ser Gly Ala Leu Thr
610                 615                 620

Ser Gly Val His Thr Phe Pro Ala Val Leu Gln Ser Ser Gly Leu Tyr
625                 630                 635                 640

Ser Leu Ser Ser Val Val Thr Val Pro Ser Ser Ser Leu Gly Thr Gln
            645                 650                 655

Thr Tyr Ile Cys Asn Val Asn His Lys Pro Ser Asn Thr Lys Val Asp
        660                 665                 670

Lys Lys Val Glu Pro Lys Ser Cys
    675                 680

<210> SEQ ID NO 63
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 63

Gly Gly Ser Gly Val Pro Leu Ser Leu Tyr Ser Gly Gly Ser Ser Gly
1               5                   10                  15

Ser Ser Gly

<210> SEQ ID NO 64
<211> LENGTH: 683
<212> TYPE: PRT
<213> ORGANISM: Artificial sequence
<220> FEATURE:
<223> OTHER INFORMATION: Synthetic polypeptide

```
<400> SEQUENCE: 64

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
```

```
            405                 410                 415
Phe Ser Cys Ser Val Met His Glu Ala Leu His Asn His Tyr Thr Gln
            420                 425                 430

Lys Ser Leu Ser Leu Ser Pro Gly Lys Gly Gly Ser Gly Val Pro Leu
            435                 440                 445

Ser Leu Tyr Ser Gly Gly Ser Ser Gly Ser Ser Gly Glu Val Gln Leu
            450                 455                 460

Val Glu Ser Gly Gly Gly Leu Val Gln Pro Gly Gly Ser Leu Arg Leu
465                 470                 475                 480

Ser Cys Ala Ala Ser Gly Phe Asn Ile Lys Asp Thr Tyr Ile His Trp
                485                 490                 495

Val Arg Gln Ser Pro Gly Lys Gly Leu Glu Trp Val Ala Arg Ile Tyr
                500                 505                 510

Pro Thr Asn Gly Tyr Thr Arg Tyr Ala Asp Ser Val Lys Gly Arg Phe
            515                 520                 525

Thr Ile Ser Ala Asp Thr Ser Lys Asn Thr Ala Tyr Leu Gln Met Asn
            530                 535                 540

Ser Leu Arg Ala Glu Asp Thr Ala Ile Tyr Tyr Cys Ser Arg Trp Gly
545                 550                 555                 560

Gly Asp Gly Phe Tyr Ala Met Asp Tyr Trp Gly Gln Gly Thr Leu Val
                565                 570                 575

Thr Val Ser Ser Ala Ser Thr Lys Gly Pro Ser Val Phe Pro Leu Ala
                580                 585                 590

Pro Ser Ser Lys Ser Thr Ser Gly Gly Thr Ala Ala Leu Gly Cys Leu
            595                 600                 605

Val Lys Asp Tyr Phe Pro Glu Pro Val Thr Val Ser Trp Asn Ser Gly
610                 615                 620

Ala Leu Thr Ser Gly Val His Thr Phe Pro Ala Val Leu Gln Ser Ser
625                 630                 635                 640

Gly Leu Tyr Ser Leu Ser Ser Val Val Thr Val Pro Ser Ser Ser Leu
                645                 650                 655

Gly Thr Gln Thr Tyr Ile Cys Asn Val Asn His Lys Pro Ser Asn Thr
            660                 665                 670

Lys Val Asp Lys Lys Val Glu Pro Lys Ser Cys
            675                 680

<210> SEQ ID NO 65
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ser Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
```

85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
450

<210> SEQ ID NO 66
<211> LENGTH: 214
<212> TYPE: PRT
<213> ORGANISM: Artificial sequence
<220> FEATURE:
<223> OTHER INFORMATION: Synthetic polypeptide

```
<400> SEQUENCE: 66

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 67
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 67

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Glu Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 68
<211> LENGTH: 449
<212> TYPE: PRT
<213> ORGANISM: Artificial sequence
<220> FEATURE:
<223> OTHER INFORMATION: Synthetic polypeptide

<400> SEQUENCE: 68

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Arg Thr Asn Gly Ser Pro Arg Leu Leu Ile
            35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
```

```
              275                 280                 285
Gln Tyr Asn Ser Thr Tyr Arg Val Val Ser Val Leu Thr Val Leu His
    290                 295                 300
Gln Asp Trp Leu Asn Gly Lys Glu Tyr Lys Cys Lys Val Ser Asn Lys
305                 310                 315                 320
Ala Leu Pro Ala Pro Ile Glu Lys Thr Ile Ser Lys Ala Lys Gly Gln
                325                 330                 335
Pro Arg Glu Pro Gln Val Tyr Thr Leu Pro Pro Ser Arg Asp Glu Leu
            340                 345                 350
Thr Lys Asn Gln Val Ser Leu Thr Cys Leu Val Lys Gly Phe Tyr Pro
        355                 360                 365
Ser Asp Ile Ala Val Glu Trp Glu Ser Asn Gly Gln Pro Glu Asn Asn
    370                 375                 380
Tyr Lys Thr Thr Pro Pro Val Leu Asp Ser Asp Gly Ser Phe Phe Leu
385                 390                 395                 400
Tyr Ser Lys Leu Thr Val Asp Lys Ser Arg Trp Gln Gln Gly Asn Val
                405                 410                 415
Phe Ser Cys Ser Val Met His Glu Ala Leu His Asn His Tyr Thr Gln
            420                 425                 430
Lys Ser Leu Ser Leu Ser Pro Gly Lys Gly Gly Ser Gly Val Pro Leu
        435                 440                 445
Ser

<210> SEQ ID NO 69
<211> LENGTH: 228
<212> TYPE: PRT
<213> ORGANISM: Artificial sequence
<220> FEATURE:
<223> OTHER INFORMATION: Synthetic polypeptide

<400> SEQUENCE: 69

Leu Tyr Ser Gly Gly Glu Val Gln Leu Val Glu Ser Gly Gly Gly Leu
1               5                   10                  15
Val Gln Pro Gly Gly Ser Leu Arg Leu Ser Cys Ala Ala Ser Gly Phe
            20                  25                  30
Asn Ile Lys Asp Thr Tyr Ile His Trp Val Arg Gln Ser Pro Gly Lys
        35                  40                  45
Gly Leu Glu Trp Val Ala Arg Ile Tyr Pro Thr Asn Gly Tyr Thr Arg
    50                  55                  60
Tyr Ala Asp Ser Val Lys Gly Arg Phe Thr Ile Ser Ala Asp Thr Ser
65                  70                  75                  80
Lys Asn Thr Ala Tyr Leu Gln Met Asn Ser Leu Arg Ala Glu Asp Thr
                85                  90                  95
Ala Ile Tyr Tyr Cys Ser Arg Trp Gly Gly Asp Gly Phe Tyr Ala Met
            100                 105                 110
Asp Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
    130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
```

```
Val Val Thr Val Pro Ser Ser Leu Gly Thr Gln Thr Tyr Ile Cys
        195                 200                 205

Asn Val Asn His Lys Pro Ser Asn Thr Lys Val Asp Lys Val Glu
    210                 215                 220

Pro Lys Ser Cys
225

<210> SEQ ID NO 70
<211> LENGTH: 219
<212> TYPE: PRT
<213> ORGANISM: Artificial sequence
<220> FEATURE:
<223> OTHER INFORMATION: Synthetic polypeptide

<400> SEQUENCE: 70

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 71
<211> LENGTH: 449
<212> TYPE: PRT
<213> ORGANISM: Artificial sequence
<220> FEATURE:
<223> OTHER INFORMATION: Synthetic polypeptide

<400> SEQUENCE: 71

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
```

```
            35                  40                  45
Ile Gly Glu Ile Tyr His Ser Gly Ser Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Trp Thr Gly Arg Thr Asp Ala Phe Asp Ile Trp Gly Gln Gly
                100                 105                 110

Thr Met Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Cys Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

<210> SEQ ID NO 72
<211> LENGTH: 681
<212> TYPE: PRT
<213> ORGANISM: Artificial sequence
<220> FEATURE:
<223> OTHER INFORMATION: Synthetic polypeptide

<400> SEQUENCE: 72

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Asp Lys Thr His Thr
    210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Glu Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly Lys Gly Gly
            435                 440                 445
Ser Gly Gly Ser Gly Ser Ser Gly Gly Gln Val Gln Leu Gln
450                 455                 460
Glu Ser Gly Pro Gly Leu Val Lys Pro Ser Gly Thr Leu Ser Leu Thr
465                 470                 475                 480
Cys Ala Val Ser Gly Gly Ser Ile Ser Ser Asn Trp Trp Ser Trp
                485                 490                 495
Val Arg Gln Pro Pro Gly Lys Gly Leu Glu Trp Ile Gly Glu Ile Tyr
                500                 505                 510
His Ser Gly Ser Thr Asn Tyr Asn Pro Ser Leu Lys Ser Arg Val Thr
            515                 520                 525
Ile Ser Val Asp Lys Ser Lys Asn Gln Phe Ser Leu Lys Leu Ser Ser
530                 535                 540
Val Thr Ala Ala Asp Thr Ala Val Tyr Tyr Cys Ala Arg Trp Thr Gly
545                 550                 555                 560
Arg Thr Asp Ala Phe Asp Ile Trp Gly Gln Gly Thr Met Val Thr Val
                565                 570                 575
Ser Ser Ala Ser Thr Lys Gly Pro Ser Val Phe Pro Leu Ala Pro Ser
                580                 585                 590
Ser Lys Ser Thr Ser Gly Gly Thr Ala Ala Leu Gly Cys Leu Val Lys
            595                 600                 605
Asp Tyr Phe Pro Glu Pro Val Thr Val Ser Trp Asn Ser Gly Ala Leu
            610                 615                 620
Thr Ser Gly Val His Thr Phe Pro Ala Val Leu Gln Ser Ser Gly Leu
625                 630                 635                 640
Tyr Ser Leu Ser Ser Val Val Thr Val Pro Ser Ser Ser Leu Gly Thr
                645                 650                 655
Gln Thr Tyr Ile Cys Asn Val Asn His Lys Pro Ser Asn Thr Lys Val
                660                 665                 670
Asp Lys Lys Val Glu Pro Lys Ser Cys
            675                 680

<210> SEQ ID NO 73
<211> LENGTH: 681
<212> TYPE: PRT
<213> ORGANISM: Artificial sequence
<220> FEATURE:
<223> OTHER INFORMATION: Synthetic polypeptide

<400> SEQUENCE: 73

Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
```

-continued

```
Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Asp Lys Thr His Thr
    210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Glu Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Gly Gly
        435                 440                 445

Ser Gly Val Pro Leu Ser Leu Tyr Ser Gly Gln Val Gln Leu Gln
    450                 455                 460

Glu Ser Gly Pro Gly Leu Val Lys Pro Ser Gly Thr Leu Ser Leu Thr
```

```
                465                 470                 475                 480
Cys Ala Val Ser Gly Ser Ile Ser Ser Asn Trp Trp Ser Trp
                    485                 490                 495
Val Arg Gln Pro Pro Gly Lys Gly Leu Glu Trp Ile Gly Glu Ile Tyr
                500                 505                 510
His Ser Gly Ser Thr Asn Tyr Asn Pro Ser Leu Lys Ser Arg Val Thr
                515                 520                 525
Ile Ser Val Asp Lys Ser Lys Asn Gln Phe Ser Leu Lys Leu Ser Ser
                530                 535                 540
Val Thr Ala Ala Asp Thr Ala Val Tyr Tyr Cys Ala Arg Trp Thr Gly
545                 550                 555                 560
Arg Thr Asp Ala Phe Asp Ile Trp Gly Gln Gly Thr Met Val Thr Val
                    565                 570                 575
Ser Ser Ala Ser Thr Lys Gly Pro Ser Val Phe Pro Leu Ala Pro Ser
                580                 585                 590
Ser Lys Ser Thr Ser Gly Gly Thr Ala Ala Leu Gly Cys Leu Val Lys
                595                 600                 605
Asp Tyr Phe Pro Glu Pro Val Thr Val Ser Trp Asn Ser Gly Ala Leu
                610                 615                 620
Thr Ser Gly Val His Thr Phe Pro Ala Val Leu Gln Ser Ser Gly Leu
625                 630                 635                 640
Tyr Ser Leu Ser Ser Val Val Thr Val Pro Ser Ser Ser Leu Gly Thr
                    645                 650                 655
Gln Thr Tyr Ile Cys Asn Val Asn His Lys Pro Ser Asn Thr Lys Val
                660                 665                 670
Asp Lys Lys Val Glu Pro Lys Ser Cys
                675                 680

<210> SEQ ID NO 74
<211> LENGTH: 677
<212> TYPE: PRT
<213> ORGANISM: Artificial sequence
<220> FEATURE:
<223> OTHER INFORMATION: Synthetic polypeptide

<400> SEQUENCE: 74

Asp Ile Gln Met Thr Gln Ser Pro Ile Leu Leu Ser Ala Ser Val Gly
1               5                   10                  15
Asp Arg Val Thr Ile Thr Cys Arg Ala Ser Gln Asp Val Asn Thr Ala
                20                  25                  30
Val Ala Trp Tyr Gln Gln Arg Thr Asn Gly Ser Pro Arg Leu Leu Ile
            35                  40                  45
Tyr Ser Ala Ser Phe Leu Tyr Ser Gly Val Pro Ser Arg Phe Ser Gly
        50                  55                  60
Ser Arg Ser Gly Thr Asp Phe Thr Leu Thr Ile Ser Ser Leu Gln Pro
65                  70                  75                  80
Glu Asp Ile Ala Asp Tyr Tyr Cys Gln Gln His Tyr Thr Thr Pro Pro
                85                  90                  95
Thr Phe Gly Ala Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
                130                 135                 140
Lys Val Gln Trp Lys Val Asp Asn Ala Leu Gln Ser Gly Asn Ser Gln
```

```
             145                 150                 155                 160
        Glu Ser Val Thr Glu Gln Asp Ser Lys Asp Ser Thr Tyr Ser Leu Ser
                         165                 170                 175
        Ser Thr Leu Thr Leu Ser Lys Ala Asp Tyr Glu Lys His Lys Val Tyr
                         180                 185                 190
        Ala Cys Glu Val Thr His Gln Gly Leu Ser Ser Pro Val Thr Lys Ser
                         195                 200                 205
        Phe Asn Arg Gly Glu Cys Asp Lys Thr His Thr Cys Pro Pro Cys Pro
        210                 215                 220
        Ala Pro Glu Leu Leu Gly Gly Pro Ser Val Phe Leu Phe Pro Pro Lys
        225                 230                 235                 240
        Pro Lys Asp Thr Leu Met Ile Ser Arg Thr Pro Glu Val Thr Cys Val
                         245                 250                 255
        Val Val Asp Val Ser His Glu Asp Pro Glu Val Lys Phe Asn Trp Tyr
                         260                 265                 270
        Val Asp Gly Val Glu Val His Asn Ala Lys Thr Lys Pro Arg Glu Glu
                         275                 280                 285
        Gln Tyr Asn Ser Thr Tyr Arg Val Val Ser Val Leu Thr Val Leu His
                         290                 295                 300
        Gln Asp Trp Leu Asn Gly Lys Glu Tyr Lys Cys Lys Val Ser Asn Lys
        305                 310                 315                 320
        Ala Leu Pro Ala Pro Ile Glu Lys Thr Ile Ser Lys Ala Lys Gly Gln
                         325                 330                 335
        Pro Arg Glu Pro Gln Val Tyr Thr Leu Pro Pro Ser Arg Asp Glu Leu
                         340                 345                 350
        Thr Lys Asn Gln Val Ser Leu Thr Cys Leu Val Lys Gly Phe Tyr Pro
                         355                 360                 365
        Ser Asp Ile Ala Val Glu Trp Glu Ser Asn Gly Gln Pro Glu Asn Asn
        370                 375                 380
        Tyr Lys Thr Thr Pro Pro Val Leu Asp Ser Asp Gly Ser Phe Phe Leu
        385                 390                 395                 400
        Tyr Ser Lys Leu Thr Val Asp Lys Ser Arg Trp Gln Gln Gly Asn Val
                         405                 410                 415
        Phe Ser Cys Ser Val Met His Glu Ala Leu His Asn His Tyr Thr Gln
                         420                 425                 430
        Lys Ser Leu Ser Leu Ser Pro Gly Lys Gly Gly Ser Gly Val Pro Leu
                         435                 440                 445
        Ser Leu Tyr Ser Gly Gly Glu Val Gln Leu Val Glu Ser Gly Gly Gly
                         450                 455                 460
        Leu Val Gln Pro Gly Gly Ser Leu Arg Leu Ser Cys Ala Ala Ser Gly
        465                 470                 475                 480
        Phe Asn Ile Lys Asp Thr Tyr Ile His Trp Val Arg Gln Ser Pro Gly
                         485                 490                 495
        Lys Gly Leu Glu Trp Val Ala Arg Ile Tyr Pro Thr Asn Gly Tyr Thr
                         500                 505                 510
        Arg Tyr Ala Asp Ser Val Lys Gly Arg Phe Thr Ile Ser Ala Asp Thr
                         515                 520                 525
        Ser Lys Asn Thr Ala Tyr Leu Gln Met Asn Ser Leu Arg Ala Glu Asp
                         530                 535                 540
        Thr Ala Ile Tyr Tyr Cys Ser Arg Trp Gly Gly Asp Gly Phe Tyr Ala
        545                 550                 555                 560
        Met Asp Tyr Trp Gly Gln Gly Thr Leu Val Thr Val Ser Ser Ala Ser
                         565                 570                 575
```

-continued

```
Thr Lys Gly Pro Ser Val Phe Pro Leu Ala Pro Ser Ser Lys Ser Thr
            580             585             590

Ser Gly Gly Thr Ala Ala Leu Gly Cys Leu Val Lys Asp Tyr Phe Pro
        595             600             605

Glu Pro Val Thr Val Ser Trp Asn Ser Gly Ala Leu Thr Ser Gly Val
    610             615             620

His Thr Phe Pro Ala Val Leu Gln Ser Ser Gly Leu Tyr Ser Leu Ser
625             630             635             640

Ser Val Val Thr Val Pro Ser Ser Ser Leu Gly Thr Gln Thr Tyr Ile
            645             650             655

Cys Asn Val Asn His Lys Pro Ser Asn Thr Lys Val Asp Lys Lys Val
        660             665             670

Glu Pro Lys Ser Cys
        675
```

MULTI-SPECIFIC LIGAND BINDERS

CROSS-REFERENCES TO RELATED APPLICATIONS

This application claims the benefit of U.S. Provisional Application No. 62/614,267, filed Jan. 5, 2018, and U.S. Provisional Application No. 62/731,781, filed Sep. 14, 2018, which are incorporated herein by reference in entirety and for all purposes

REFERENCE TO A "SEQUENCE LISTING," A TABLE, OR A COMPUTER PROGRAM LISTING APPENDIX SUBMITTED AS AN ASCII FILE

The Sequence Listing written in file 048440-662001WO_Sequence_Listing_ST25, created Jan. 7, 2019, 254,720 bytes, machine format IBM-PC, MS Windows operating system, is hereby incorporated by reference.

BACKGROUND

Immunotherapeutics have emerged as a promising treatment strategy for numerous diseases. However, immunotherapy suffers from significant safety and manufacturing issues. Adverse side effects remain one of the most significant issues with all therapeutics, especially with checkpoint inhibitors, BiTEs, and CAR T cells. Further, difficulties in the manufacturing of bispecific molecules at clinical scale (i.e., high yield) have severely limited the introduction of these potent therapeutics into the clinic. Provided herein are, inter alia, solutions to these and other needs in the art.

BRIEF SUMMARY OF THE INVENTION

In an aspect is provided a peptide including: (i) a first protein dimerizing domain bound to a first ligand binding domain through a first chemical linker; and (ii) a second protein dimerizing domain bound to the first ligand binding domain through a second chemical linker; wherein the first protein dimerizing domain is capable of non-covalently binding to the second protein dimerizing domain to form a second ligand binding domain.

In an aspect is provided a peptide including: (i) a first protein dimerizing domain bound to a first multivalent ligand binding domain through a first chemical linker; and (ii) a second protein dimerizing domain bound to the first multivalent ligand binding domain through a second chemical linker; wherein the first protein dimerizing domain is capable of non-covalently binding to the second protein dimerizing domain to form a second ligand binding domain.

In an aspect is provided an isolated nucleic acid encoding a peptide as described herein, including embodiments thereof.

In an aspect, an expression vector including the nucleic acid provided herein, including embodiments thereof, is provided.

In an aspect is provided a pharmaceutical composition including a peptide as described herein, including embodiments thereof, and pharmaceutically acceptable excipient In an aspect is provided a method including administering to a subject in need thereof a therapeutically effective amount of a peptide as described herein, including embodiments thereof.

BRIEF DESCRIPTION OF THE DRAWINGS

FIG. 9A. Cartoon showing embodiment of a peptide provided herein. FIG. 9B. SDS-PAGE of material after initial affinity chromatography step. So much material was produced that the purification column was saturated immediately, preventing the retention of additional material in the media.

FIG. 10A. Bispecific (switchblade) binding to Her2. FIG. 10B. Control: 183E Fab binding to Her2. FIG. 10C. Bispecific (switchblade) binding to CD16a. FIG. 10D. Anti-CD16 binding to CD16a.

FIG. 12A. Cartoon showing embodiment of a peptide provided herein where the ligand binding domain is an anti-CD16 single domain antibody and the second ligand binding domain is a trastuzumab Fab. Linker position parameters were tested. FIG. 12B. Expression data of exemplified constructs including different linker lengths. Over 1 mg/ml in media at 6 days—the samples are direct from supernatant. In the sample marked with the asterisk, the ExpiCHO cells were not healthy (i.e. significant cell death) and still produced considerable amount of protein. This highlights the robustness of this platform for protein production.

FIG. 15A. The bispecific antibody (embodiment of the peptide provided herein) consisting of trastuzumab Fab linked by an anti-CD16 nanobody activates CD16 expressing Jurkat cells more effectively than Herceptin (clinical Trastuzumab IgG). The activation indicates that the bispecific antibody is able to bind tumor cells (SKBR3) and CD16 expressing Jurkat cells simultaneously. FIG. 15B. The trispecific antibody from FIG. 13 is able to bind to Raji cells (CD20 positive) and MV411 cells (CD33 and CD123 positive). Shown is the histogram from analytical cytometry. Here two cell lines were used: Raji cells expressing CD20 and MV411 expressing both CD33 and CD123. A secondary antibody that binds to the kappa chain was used to detect binding of the trispecific bionic. A shift to the right indicates binding. These data indicate the trispecific bionic can recognize different antigens. FIG. 15C. A bispecific antibody (embodiment of the peptide provided herein) consisting of an anti-HER2 nanobody as the linker from the light chain to the heavy chain of anti-CD3 Fab (HER2 Fab) or anti-CD3 IgG (HER2 IgG). Both the IgG and Fab format are able to activate Jurkat cells in the presence of SKOV3 cells. The parental anti-CD3 IgG (anti-CD3) lacking the HER2 nanobody is unable to activate Jurkat cells.

DETAILED DESCRIPTION

Figure 1:
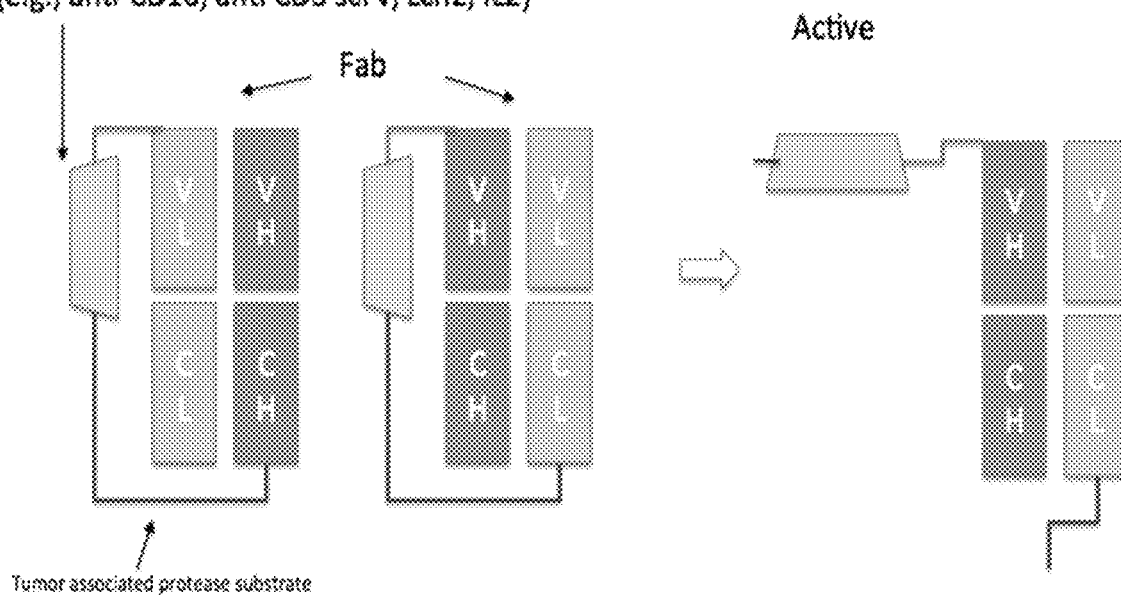
FIG. 1. Cartoon of a Fab-based switchblade (embodiment of a peptide provided herein) sterically inactive (left two cartoons) and active (right cartoon) following cleavage of the tumor associated protease substrate. Shown is a peptide provided herein including from the N-terminus to the C-terminus: an antibody heavy chain (first protein dimerzing domain), a first chemical linker, a first ligand binding domain, a second chemical linker and and an antibody light chain (second protein dimerizing domain). The left panel is a representation of the uncleaved peptide, while the right panel shows the peptide after proteolytic cleavage of the first chemical linker.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Definitions

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

A "chemical linker," as provided herein, is a covalent linker, anon-covalent linker, a peptide or peptidyl linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof.

The chemical linker as provided herein may be a bond, —O—, —S—, —C(O)—, —C(O)O—, —C(O)NH—, —S(O)$_2$NH—, —NH—, —NHC(O)NH—, substituted (e.g., substituted with a substituent group, a size-limited substituent or a lower substituent group) or unsubstituted alkylene, substituted (e.g., substituted with a substituent group, a size-limited substituent or a lower substituent group) or unsubstituted heteroalkylene, substituted (e.g., substituted with a substituent group, a size-limited substituent or a lower substituent group) or unsubstituted cycloalkylene, substituted (e.g., substituted with a substituent group, a size-limited substituent or a lower substituent group) or unsubstituted heterocycloalkylene, substituted (e.g., substituted with a substituent group, a size-limited substituent or a lower substituent group) or unsubstituted arylene or substituted (e.g., substituted with a substituent group, a size-limited substituent or a lower substituent group) or unsubstituted heteroarylene.

The chemical linker as provided herein may be a bond, —O—, —S—, —C(O)—, —C(O)O—, —C(O)NH—, —S(O)$_2$NH—, —NH—, —NHC(O)NH—, substituted or unsubstituted (e.g., $C_1$-$C_{20}$, $C_1$-$C_{10}$, $C_1$-$C_5$) alkylene, substituted or unsubstituted (e.g., 2 to 20 membered, 2 to 10 membered, 2 to 5 membered) heteroalkylene, substituted or unsubstituted (e.g., $C_3$-$C_8$, $C_3$-$C_6$, $C_3$-$C_5$) cycloalkylene, substituted or unsubstituted (e.g., 3 to 8 membered, 3 to 6 membered, 3 to 5 membered) heterocycloalkylene, substituted or unsubstituted (e.g., $C_6$-$C_{10}$, $C_6$-$C_8$, $C_6$-$C_5$) arylene or substituted or unsubstituted (e.g., 5 to 10 membered, 5 to 8 membered, 5 to 6 membered) heteroarylene.

In embodiments, the chemical linker is a covalent linker. In embodiments, the chemical linker is a hydrocarbon linker. In embodiments, the chemical linker is a cleavable peptide linker.

Thus, a chemical linker as provided herein may include a plurality of chemical moieties, wherein each of the plurality of chemical moieties is chemically different. Alternatively, the chemical linker may be a non-covalent linker. Examples of non-covalent linkers include without limitation, ionic bonds, hydrogen bonds, halogen bonds, van der Waals interactions (e.g. dipole-dipole, dipole-induced dipole, London dispersion), ring stacking (pi effects), and hydrophobic interactions. In embodiments, a chemical linker is formed using conjugate chemistry including, but not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition).

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. For example, a selected residue in a selected antibody (or Fab domain) corresponds to light chain threonine at Kabat position 40, when the selected residue occupies the same essential spatial or other structural relationship as a light chain threonine at Kabat position 40. In some embodiments, where a selected protein is aligned for maximum homology with the light chain of an antibody (or Fab domain), the position in the aligned selected protein aligning with threonine 40 is said to correspond to threonine 40. Instead of a primary sequence alignment, a three dimensional structural alignment can also be used, e.g., where the structure of the selected protein is aligned for maximum correspondence with the light chain threonine at Kabat position 40, and the overall structures compared. In this case, an amino acid that occupies the same essential position as threonine 40 in the structural model is said to correspond to the threonine 40 residue.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J Mol. Biol.* 48:443, by the search for similarity method of Pearson and Lipman (1988) *Proc. Nat'l. Acad. Sci.* USA 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=-4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci.* USA 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul (1993) *Proc. Nat. Acad. Sci.* USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"CD3" as referred to herein includes any of the recombinant or naturally-occurring forms of the Cluster of Differentiation 3 (CD3) proteins or variants or homologs thereof that comprise the CD3 complex that mediates signal transduction and maintains CD3 complex activity (e.g. within at least 50%, 80%, 90%, 95%, 96%, 97%, 98%, 99% or 100% activity compared to the CD3 complex). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3 proteins in the CD3 complex. In embodiments, the CD3 protein is substantially identical to the protein identified by the UniProt reference number P04234 or a variant or homolog having substantial identity thereto. In embodiments, the CD3 protein is substantially identical to the protein identified by the UniProt reference number P09693 or a variant or homolog having substantial identity thereto. In embodiments, the CD3 protein is substantially identical to the protein identified by the UniProt reference number P07766 or a variant or homolog having substantial identity thereto.

"CD16" as referred to herein includes any of the recombinant or naturally-occurring forms of the Cluster of Differentiation 16 (CD16) protein, also known as low affinity immunoglobulin gamma Fc region receptor III-A, or variants or homologs thereof that maintain CD16 activity (e.g. within at least 50%, 80%, 90%, 95%, 96%, 97%, 98%, 99% or 100% activity compared to CD16). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD16 protein. In embodiments, the CD16 protein is substantially identical to the protein identified by the UniProt reference number P08637 or a variant or homolog having substantial identity thereto.

"Her2" as referred to herein includes any of the recombinant or naturally-occurring forms of the human epidermal growth factor receptor 2 protein, also known as receptor tyrosine-protein kinase erbB-2, or variants or homologs thereof that maintain Her2 activity (e.g. within at least 50%, 80%, 90%, 95%, 96%, 97%, 98%, 99% or 100% activity compared to Her2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Her2 protein. In embodiments, the Her2 protein is substantially identical to the protein identified by the UniProt reference number P04626 or a variant or homolog having substantial identity thereto.

"CD123" as referred to herein includes any of the recombinant or naturally-occurring forms of CD123, also known as interleukin 3 receptor, alpha, or variants or homologs thereof that maintain CD123 activity (e.g. within at least 50%, 80%, 90%, 95%, 96%, 97%, 98%, 99% or 100% activity compared to CD123). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD123 protein. In embodiments, the CD123 protein is substantially identical to the protein identified by the UniProt reference number P26951 or a variant or homolog having substantial identity thereto.

"CD20" as referred to herein includes any of the recombinant or naturally-occurring forms of CD20, also known as B-lymphocyte antigen CD20, or variants or homologs thereof that maintain CD20 activity (e.g. within at least 50%, 80%, 90%, 95%, 96%, 97%, 98%, 99% or 100% activity compared to CD20). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD20 protein. In embodiments, the CD20 protein is substantially identical to the protein identified by the UniProt reference number P11836 or a variant or homolog having substantial identity thereto.

"Tumor-associated glycoprotein 72" (TAG72) as referred to herein includes any of the recombinant or naturally-occurring forms of TAG72, or variants or homologs thereof that maintain TAG72 activity (e.g. within at least 50%, 80%, 90%, 95%, 96%, 97%, 98%, 99% or 100% activity compared to TAG72). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring TAG72 protein.

"Carcinoembryonic antigen" (CEA) as referred to herein describes a set of highly related glycoproteins involved in cell adhesion and includes any of the recombinant or naturally-occurring forms of CEA variants or homologs thereof that maintain CEA activity (e.g. within at least 50%, 80%, 90%, 95%, 96%, 97%, 98%, 99% or 100% activity compared to CEA). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to naturally occurring CEA proteins. In embodiments, the CEA protein is substantially identical to the protein identified by the UniProt reference number Q13984 or a variant or homolog having substantial identity thereto.

"CD252" as referred to herein includes any of the recombinant or naturally-occurring forms of CD252, also known as OX40 ligand (OX40L) and tumor necrosis factor ligand superfamily member 4, or variants or homologs thereof that maintain CD252 activity (e.g. within at least 50%, 80%, 90%, 95%, 96%, 97%, 98%, 99% or 100% activity compared to CD252). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD252 protein. In embodiments, the CD252 protein is substantially identical to the protein identified by the UniProt reference number P23510 or a variant or homolog having substantial identity thereto.

"Glucocorticoid-induced tumor necrosis factor receptor" (GITR) as referred to herein includes any of the recombinant or naturally-occurring forms of GITR, also known as tumor necrosis factor receptor superfamily member 18, or variants or homologs thereof that maintain GITR activity (e.g. within at least 50%, 80%, 90%, 95%, 96%, 97%, 98%, 99% or 100% activity compared to GITR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring GITR protein. In embodiments, the GITR protein is substantially identical to the protein identified by the UniProt reference number Q9Y5U5 or a variant or homolog having substantial identity thereto.

"41BB" or "4-1BB" as referred to herein includes any of the recombinant or naturally-occurring forms of 41BB, also known as tumor necrosis factor ligand superfamily member 9, or variants or homologs thereof that maintain 41BB activity (e.g. within at least 50%, 80%, 90%, 95%, 96%, 97%, 98%, 99% or 100% activity compared to 41BB). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring 41BB protein. In embodiments, the 41BB protein is substantially identical to the protein identified by the UniProt reference number P41273 or a variant or homolog having substantial identity thereto.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region, involved in binding the target antigen, and a constant ("C") region that interacts with other components of the immune system. The light and heavy chain variable regions (also referred to herein as light chain variable (VL) domain and heavy chain variable (VH) domain, respectively) come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_{H1}$ by a disulfide bond. The F(ab)'2 may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL), variable light chain (VL) domain or light chain variable region and variable heavy chain (VH), variable heavy chain (VH) domain or heavy chain variable region refer to these light and heavy chain regions, respectively. The terms variable light chain (VL), variable light chain (VL) domain and light chain variable region as referred to herein may be used interchangeably. The terms variable heavy chain (VH), variable heavy chain (VH) domain and heavy chain variable region as referred to herein may be used interchangeably. The Fc (i.e. fragment crystallizable region) is the "base" or "tail" of an immunoglobulin and is typically composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins. In embodiments, the Fc region includes a constant heavy chain domain 3 (CH3 domain) and a constant heavy chain domain 2 (CH2 domain).

The epitope of an antibody is the region of its antigen to which the antibody binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

The term "antigen" as provided herein refers to molecules capable of binding to the antibody binding domain provided herein. An "antigen binding domain" as provided herein is a region of an antibody that binds to an antigen (epitope). As described above, the antigen binding domain is generally composed of one constant and one variable domain of each of the heavy and the light chain (VL, VH, CL and CH1, respectively). The paratope or antigen-binding site is formed on the N-terminus of the antigen binding domain. The two variable domains of an antigen binding domain typically bind the epitope on an antigen.

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348: 552-554 (1990); Marks et al., *Biotechnology* 10:779-783 (1992)).

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633, 425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676, 980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

An "antibody variant" as provided herein refers to a polypeptide capable of binding to an antigen and including one or more structural domains of an antibody or fragment thereof. Non-limiting examples of antibody variants include single-domain antibodies or nanobodies, affibodies (polypeptides smaller than monoclonal antibodies (e.g., about 6 kDA) and capable of binding antigens with high affinity and imitating monoclonal antibodies, monospecific $Fab_2$, bispecific $Fab_2$, trispecific $Fab_3$, monovalent IgGs, scFv, bispecific diabodies, trispecific triabodies, scFv-Fc, minibodies, IgNAR, V-NAR, hcIgG, VhH, or peptibodies. A "nanobody" or "single domain antibody" as described herein is commonly well known in the art and refers to an antibody fragment consisting of a single monomeric variable antibody domain. Like a whole antibody, it is able to bind selectively to a specific antigen. A "peptibody" as provided herein refers to a peptide moiety attached (through a covalent or non-covalent linker) to the Fc domain of an antibody. Further non-limiting examples of antibody variants known in the art include antibodies produced by cartilaginous fish or camelids. A general description of antibodies from camelids and the variable regions thereof and methods for their production, isolation, and use may be found in references WO97/49805 and WO 97/49805 which are incorporated by reference herein in their entirety and for all purposes. Likewise, antibodies from cartilaginous fish and the variable regions thereof and methods for their production, isolation, and use may be found in WO2005/118629, which is incorporated by reference herein in its entirety and for all purposes.

An "affibody" as described herein is commonly well known in the art and refers to small, robust proteins engineered to bind to a large number of target proteins or peptides with high affinity, by imitating monoclonal antibodies. Affibodies are therefore a member of the family of antibody mimetics. In embodiments, an affibody is a molecule including of three alpha helices with about 58 amino acids and a molar mass of about 6 kDa.

A "single domain antibody" as provided herein refers to an antibody fragment including a single monomeric variable antibody domain. Like a whole antibody, a single domain antibody is able to bind selectively to a specific antigen. The molecular weight of a single domain antibody is 12-15 kDa, single domain antibody. In embodiments, a single domain antibody is a variable heavy chain domain. In embodiments, a single domain antibody is a variable light chain domain. Non-limiting examples of single domain antibodies include camelid-derived VHH fragments and VNAR (variable immunoglobulin new antigen receptor) fragments. In embodiments, the single-domain antibody is a peptide domain of about 110 amino acids. In embodiments, the single-domain antibody includes a variable heavy chain domain. In embodiments, the single-domain antibody includes a variable light chain domain.

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "ligand" refers to an agent, e.g., a polypeptide or other molecule, capable of binding to a ligand binding domain (e.g., receptor or antibody, antibody variant, antibody region or fragment thereof).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated, that the resulting reaction product can be produced directly from a reaction between the added reagents or from an intermediate from one or more of the added reagents which can be produced in the reaction mixture.

The term "contacting" may include allowing two species to react, interact, or physically touch (e.g., bind), wherein the two species may be, for example, an antibody construct as described herein and a cancer protein. In embodiments, contacting includes, for example, allowing an antibody construct to bind to a cancer protein expressed on a cancer cell.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The term "plasmid," "expression vector," or "viral vector" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids. Suitable viral vectors contemplated herein include, for example, lentiviral vectors and onco-retroviral vectors.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish. In some embodiments, the sample is obtained from a human.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma (Mantel cell lymphoma), head and neck cancer, colorectal cancer, prostate cancer, pancreatic cancer, melanoma, breast cancer, neuroblastoma).

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma (e.g., Mantel cell lymphoma, follicular lymphoma, diffuse large B-cell lymphoma, marginal zona lymphoma, Burkitt's lymphoma), sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia (e.g., lymphoblastic leukemia, chronic lymphocytic leukemia, hairy cell leukemia), acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The P388 leukemia model is widely accepted as being predictive of in vivo anti-leukemic activity. It is believed that a compound that tests positive in the P388 assay will generally exhibit some level of anti-leukemic activity in vivo regardless of the type of leukemia being treated. Accordingly, the present application includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., cancer) means that the disease is caused by (in whole or in part), or a symptom of the disease is caused by (in whole or in part) the substance or substance activity or function.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). For example, certain methods herein treat cancer by decreasing or reducing or preventing the occurrence, growth, metastasis, or progression of cancer; or treat cancer by decreasing a symptom of cancer. Symptoms of cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) would be known or may be determined by a person of ordinary skill in the art.

As used herein the terms "treatment," "treat," or "treating" refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

An "effective amount" is an amount sufficient to accomplish a stated purpose (e.g. achieve the effect for which it is administered, treat a disease, reduce enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

Formulations suitable for oral administration can consist of (a) liquid solutions, such as an effective amount of the antibodies provided herein suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

The combined administration contemplates co-administration, using separate formulations or a single pharmaceutical formulation, and consecutive administration in either order, wherein preferably there is a time period while both (or all) active agents simultaneously exert their biological activities.

Effective doses of the compositions provided herein vary depending upon many different factors, including means of administration, target site, physiological state of the patient, whether the patient is human or an animal, other medications administered, and whether treatment is prophylactic or therapeutic. However, a person of ordinary skill in the art would immediately recognize appropriate and/or equivalent doses looking at dosages of approved compositions for treating and preventing cancer for guidance.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances, and the like, that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Peptide Compositions

Provided herein are, inter alia, peptide compositions having multi-specific binding capabilities useful for therapeutic and diagnostic purposes. The peptide compositions provided herein are polypeptides including at least two ligand binding domains able to target (bind) two or more ligands (e.g., antigens) at the same time. The peptide compositions provided herein can be produced at very high yields and are therefore easy to manufacture. The peptide compositions provided herein are, inter alia, therapeutically useful for the simultaneous targeting of two antigens and for sequestering multiple ligands. For example, the first ligand binding domain may target an immune cell-specific ligand (e.g., CD3 or CD16 for T cells or NK cells, respectively) and the second ligand binding domain may target a tumor cell-specific ligand (e.g., CD 19). The peptide compositions may further be useful for the effective transport of one ligand binding domain across the blood brain barrier through binding of the other ligand binding domain to a transferrin receptor. The ligand binding domains included in the peptide compositions provided herein may bind to any cellular protein (cancerous or non-cancerous) or fragment thereof and include, without limitation, domains of an antibody, antibody variant or fragments thereof (e.g., single chain antibodies, nanobodies, affybodies, Fabs), domains that bind to cytokines (e.g., interleukins) or transport proteins (e.g., lipocalins), domains that bind to immune cells (e.g., Nk cells, T cells), domains that bind to cancer-specific antigens (e.g., Her2, CD20, CEA, TAG72).

The chemical linkers (e.g., first and/or second chemical linker) included in the peptide compositions provided herein may be cleavable and thereby conveying disease site specificity to the compositions provided herein. For example, the first and/or second chemical linker may be a cleavable linker including a cleavage site recognized by a tumor-specific protease. In the absence of a tumor-specific protease the first and/or second chemical linker is not cleaved and the peptide composition is in a sterically occluded conformation, wherein the first ligand binding domain and/or the second ligand binding domain do not bind their corresponding ligand. In the presence of a tumor-specific protease the first and/or second chemical linker is cleaved and the peptide composition forms a sterically open conformation, wherein the first ligand binding domain and/or the second ligand binding domain are capable of binding their corresponding ligand. Thus, additional functionality (e.g., tumor-specific activation) can be included in the peptide compositions through steric hindrance or masking of one or more ligand binding domains.

The peptide compositions provided herein are surprisingly stable and exhibit increased affinity to a variety of different ligands. Therefore, the compositions and methods provided herein address the need in the art for high yield production of multi-specific therapeutics (e.g., bispecific antigen binders) that are highly effective and specific exhibiting minimal adverse effects. The peptides provided herein including embodiments thereof may include a first and a second ligand binding domain connected through a linker and both ligand binding domains are able to bind to their respective ligand without cleavage of the linker. The peptides provided herein that do not require cleavage of the linker (e.g., first or second chemical linker) for their first and second ligand binding domain to bind their respective ligands, are also referred to herein as "bionics" or "bionic molecules."

The peptides may include a cleavable linker (first or second chemical linker) and only upon cleavage of the first or second chemical linker are the first and/or second ligand binding domain able to bind to their corresponding ligand/ binding partner. Peptides including a cleavable linker and a first ligand binding domain which is occluded unless the linker is cleaved are also referred to herein as "switchblade" or "switchblade molecule."

The terms "Ig switchblade", "Fc switchblade", IgG switchblade" or "antibody switchblade" as used herein refer to a complex which includes two peptides as provided herein including embodiments thereof which are bound to each other through their respective ligand binding domains and where their respective ligand binding domains are Fc dimerizing domains.

In an aspect is provided a peptide including: (i) a first protein dimerizing domain bound to a first ligand binding domain through a first chemical linker; and (ii) a second protein dimerizing domain bound to the first ligand binding domain through a second chemical linker; wherein the first protein dimerizing domain is capable of non-covalently binding to the second protein dimerizing domain to form a second ligand binding domain.

A "ligand binding domain" as provided herein refers to a peptide domain capable of selectively binding to a target ligand. A ligand binding domain may covalently or non-covalently bind to a target ligand. Non-limiting examples of ligand binding domains include single chain antibodies, antibody variants or fragments thereof, antibodies or fragments thereof, an antibody Fc region or fragments thereof. In embodiments, the ligand binding domain is a Fab. In embodiments, the ligand binding domain is a single domain antibody (sdAb). In embodiments, the ligand binding domain is a fragment crystallizable (Fc) dimerizing domain. An "Fc dimerzing domain" as referred to herein is a polypeptide including an antibody CH2 domain or fragment thereof bound (covalently and/or non-covalently) to an antibody CH3 domain or fragment thereof. Upon binding of two dimerizing domains an antibody Fc region is formed. Thus, an Fc region may include a first dimerizing domain non-covalently or covalently bound to a second dimerizing domain. In embodiments, the CH3 domain of the first Fc dimerzing domain is non-covalently bound to the CH3 domain of the second Fc dimerzing domain. In embodiments, the CH2 domain of the first Fc dimerzing domain is covalently bound to the CH2 domain of the second Fc dimerzing domain. In embodiments, the CH2 domain of the first Fc dimerzing domain is bound to the CH2 domain of the second Fc dimerzing domain through a disulfide linkage. In embodiments, the Fc dimerzing domain includes a CH2 domain and a CH3 domain. In embodiments, the Fc dimerzing domain includes from the N-terminus to the C-terminus a CH2 domain and a CH3 domain.

The ligand binding domains provided herein (e.g., first, second, third or fourth ligand binding domain) may bind a plurality (at least two) of the same type of ligand, two or more different regions of the same ligand or a plurality of (two or more) different ligands. Wherein the ligand binding domains provided herein bind a plurality of the same type of ligand, the same type of ligand may form part of one cell or of two or more different cells and the ligand binding domains bind separate ligand molecules. Alternatively, the ligand binding domains provided herein may bind two or more different regions of the same ligand (e.g., different epitopes of the same protein). Further, the ligand binding domains provided herein may bind a plurality of different ligands and the plurality of different ligands may form part of one cell or a plurality of cells.

In embodiments, the first ligand binding domain is different from the second ligand binding domain. The first ligand binding domain may be a single-domain antibody domain. The second ligand binding domain may be a protein domain including two protein dimerizing domains (e.g., a first and a second protein dimerizing domain). The first protein dimerzing domain and the second protein dimerzing domain may be covalently and/or non-covalently bound to each other. Thus, in embodiments, the first protein dimerzing domain is bound to the second protein dimerzing domain. In embodiments, the peptide further includes a covalent bond connecting the first protein dimerzing domain and the second protein dimerzing domain. In embodiments, the covalent bond is a disulfide bond. In embodiments, the second protein dimerzing domain is a Fab domain.

In embodiments, the first protein dimerzing domain includes a variable light chain domain. In embodiments, the first protein dimerzing domain includes a constant light chain domain. In embodiments, the variable light chain domain is bound to the first ligand binding domain through the constant light chain domain. In embodiments, the variable light chain domain is bound to the first ligand binding domain through the first chemical linker. In embodiments, the first protein dimerzing domain includes an antibody light chain. In embodiments, the first protein dimerzing domain is an antibody light chain.

A "variable light chain (VL) domain" as provided herein refers to the variable region of the light chain of an antibody, an antibody variant or fragment thereof. Likewise, the "variable heavy chain (VH) domain" as provided herein refers to the variable region of the heavy chain of an antibody, an antibody variant or fragment thereof. As described above, the variable light chain domain and the variable heavy chain domain together form the paratope, which binds an antigen (epitope). The paratope or antigen-binding site is formed at the N-terminus of an antibody, an antibody variant or fragment thereof. In embodiments, the variable light chain (VL) domain includes CDR L1, CDR L2, CDR L3 and FR L1, FR L2, FR L3 and FR L4 (framework regions) of an antibody light chain. In embodiments, the variable heavy chain (VH) domain includes CDR H1, CDR H2, CDR H3 and FR H1, FR H2, FR H3 and FR H4 (framework regions) of an antibody heavy chain.

The terms "CDR L1", "CDR L2" and "CDR L3" as provided herein refer to the complementarity determining regions (CDR) 1, 2, and 3 of the variable light (L) chain of an antibody or fragment thereof. In embodiments, the variable light chain provided herein includes in N-terminal to C-terminal direction a CDR L1, a CDR L2 and a CDR L3. Likewise, the terms "CDR H1", "CDR H2" and "CDR H3" as provided herein refer to the complementarity determining regions (CDR) 1, 2, and 3 of the variable heavy (H) chain of an antibody or fragment thereof. In embodiments, the variable light chain provided herein includes in N-terminal to C-terminal direction a CDR L1, a CDR L2 and a CDR L3.

"Framework regions" (FRs) are those variable region residues other than the CDR residues. The FRs of VH are also referred to herein as FR H1, FR H2, FR H3 and FR H4, respectively, wherein FR H1 corresponds to FR 1 of VH, FR H2 corresponds to FR 2 of VH, FR H3 corresponds to FR 3 of VH and FR H4 corresponds to FR 4 of VH. Likewise, the FRs of the variable region of the heavy chain are further referred to herein as HFR1, HFR2, HFR3 and HFR4, respectively, wherein HFR1 corresponds to FR 1 of VH, HFR 2 corresponds to FR 2 of VH, HFR 3 corresponds to FR 3 of VH and HFR 4 corresponds to FR 4 of VH. Likewise, the FRs of VL are referred to herein as FR L1, FR L2, FR L3 and FR L4, respectively, wherein FR L1 corresponds to FR 1 of VL, FR L2 corresponds to FR 2 of VL, FR L3 corresponds to FR 3 of VL and FR L4 corresponds to FR 4 of VL. Likewise, the FRs of the variable region of the light chain are further referred to herein as LFR1, LFR2, LFR3 and LFR4, respectively, wherein LFR1 corresponds to FR 1 of VL, LFR 2 corresponds to FR 2 of VL, LFR 3 corresponds to FR 3 of VL and LFR 4 corresponds to FR 4 of VL.

In embodiments, the variable light chain (VL) domain and a constant light chain (CL) domain form part of an antibody light chain. In embodiments, the variable heavy chain (VH) domain and a constant heavy chain (CH1) domain form part of an antibody heavy chain. In embodiments, the variable heavy chain (VH) domain and one or more constant heavy chain (CH1, CH2, or CH3) domains form part of an antibody heavy chain. In embodiments, the variable light chain (VL) domain forms part of an antibody fragment. In embodiments, the variable heavy chain (VH) domain forms part of an antibody fragment. In embodiments, the variable light chain (VL) domain forms part of an antibody variant. In embodiments, the variable heavy chain (VH) domain forms part of an antibody variant. In embodiments, the variable light chain (VL) domain forms part of a Fab. In embodiments, the variable heavy chain (VH) domain forms part of a Fab. In embodiments, the variable light chain (VL) domain forms part of a scFv. In embodiments, the variable heavy chain (VH) domain forms part of a scFv.

In embodiments, the second protein dimerizing domain includes a variable heavy chain domain. In embodiments, the second protein dimerizing domain includes a constant heavy chain domain. In embodiments, the constant heavy chain domain is bound to the first ligand binding domain through the variable heavy chain domain. In embodiments, the constant heavy chain domain is bound to the first ligand binding domain through the second chemical linker. In embodiments, the second protein dimerizing domain includes an antibody heavy chain. In embodiments, the second protein dimerizing domain is an antibody heavy chain.

In embodiments, the first protein dimerizing domain includes a variable heavy chain domain. In embodiments, the first protein dimerizing domain includes a constant heavy chain domain. In embodiments, the variable heavy chain domain is bound to the first ligand binding domain through the constant heavy chain domain. In embodiments, the variable heavy chain domain is bound to the first ligand binding domain through the first chemical linker. In embodiments, the first protein dimerizing domain includes an antibody heavy chain. In embodiments, the first protein dimerizing domain is an antibody heavy chain.

In embodiments the second protein dimerizing domain includes a variable light chain domain. In embodiments, the second protein dimerizing domain includes a constant light chain domain. In embodiments, the constant light chain domain is bound to the first ligand binding domain through the variable light chain domain. In embodiments, the constant light chain domain is bound to the first ligand binding domain through the second chemical linker. In embodiments, the second protein dimerizing domain includes an antibody light chain. In embodiments, the second protein dimerizing domain is an antibody light chain.

In embodiments, the second ligand binding domain is a Fab domain. In embodiments, the second protein dimerizing domain is bound to an Fc domain through a third chemical linker.

In embodiments, the first chemical linker is bound to the N-terminus of the first ligand binding domain and the second chemical linker is bound to the C-terminus of the first ligand binding domain. In embodiments, the first chemical linker is bound to the C-terminus of the first ligand binding domain and the second chemical linker is bound to the N-terminus of the first ligand binding domain.

Figure 21:
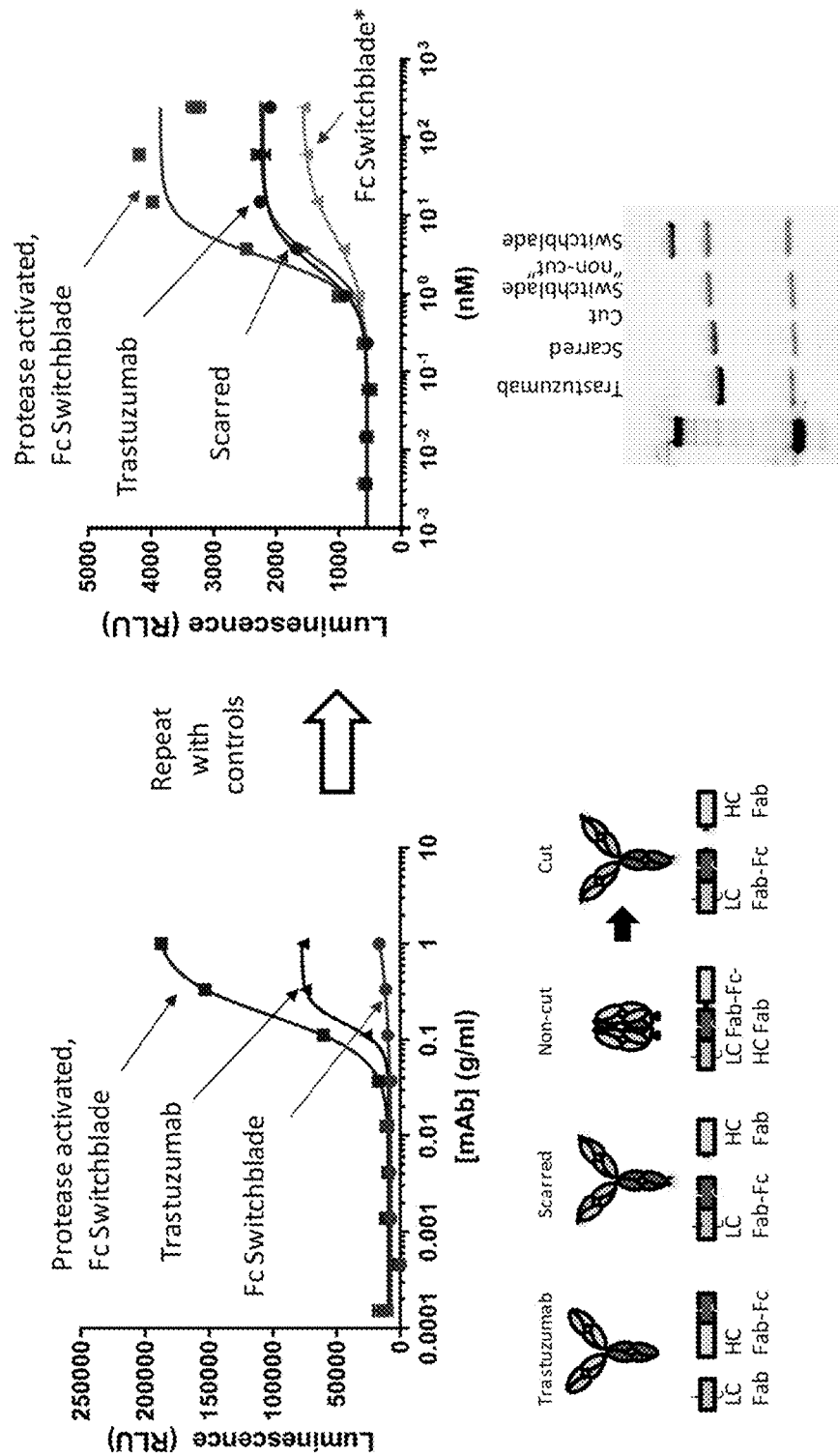
FIG. 21. To test the activation of the Fc switchblade, we compared protease activated Fc switchblade to the Fc switchblade (before activation) and trastuzumab. We tested activity using the same cell based assay as FIG. 16. The protease activated sample had higher activity than trastuzumab. Without activation, the Fc switchblade does not activate the Jurkat cells. The protease activated molecule includes FAB light chain is directly fused to the Fc. In other embodiments, the Fab heavy chain is directly fused to the Fc, which might explain the higher activation of the protease activated molecule compared to trastuzumab (left panel). To test this, we made a 'scarred' version, where the Fc is connected the light chain thereby corresponding to the protease activated molecule. The 'scarred' molecule includes the residues that would remain to be attached to the C and N terminus of the heavy and light chain after protease treatment. In other words, the scarred molecule is a recreation of the activated/proteolytically cleaved switchblade. In the right panel (effectively a repeat of the left panel but with the scarred control), the activation (luminescence) is the same for the scarred and trastuzumab. Thus, the alternative fusion is not the issue.
Figure 22:
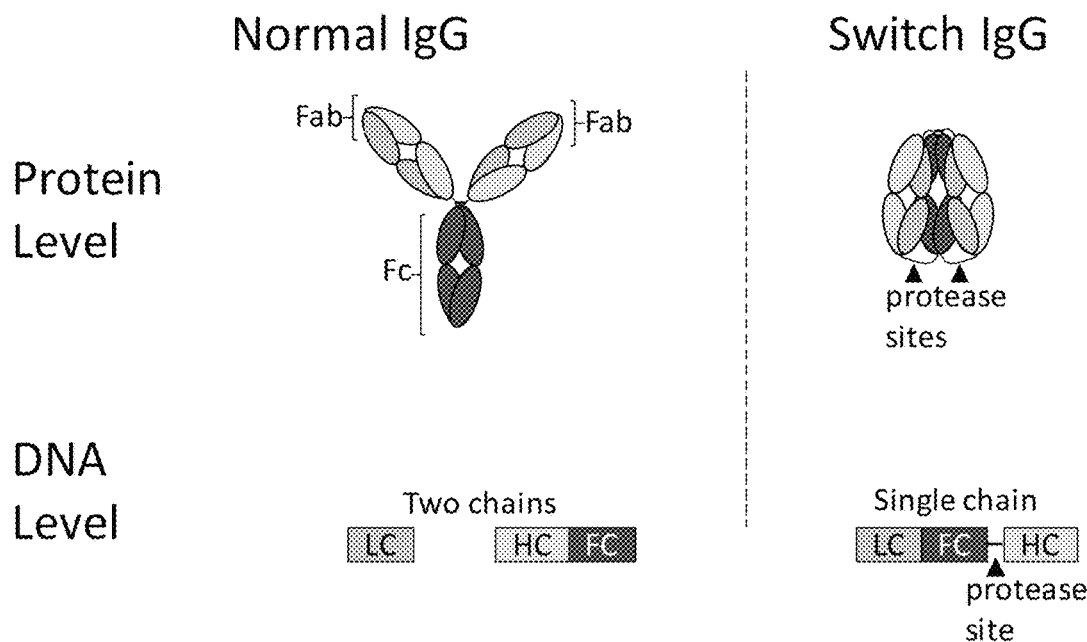
FIG. 22. Cartoon depiction of masking the Fc switchblade at the protein level and DNA level.
Figure 23:
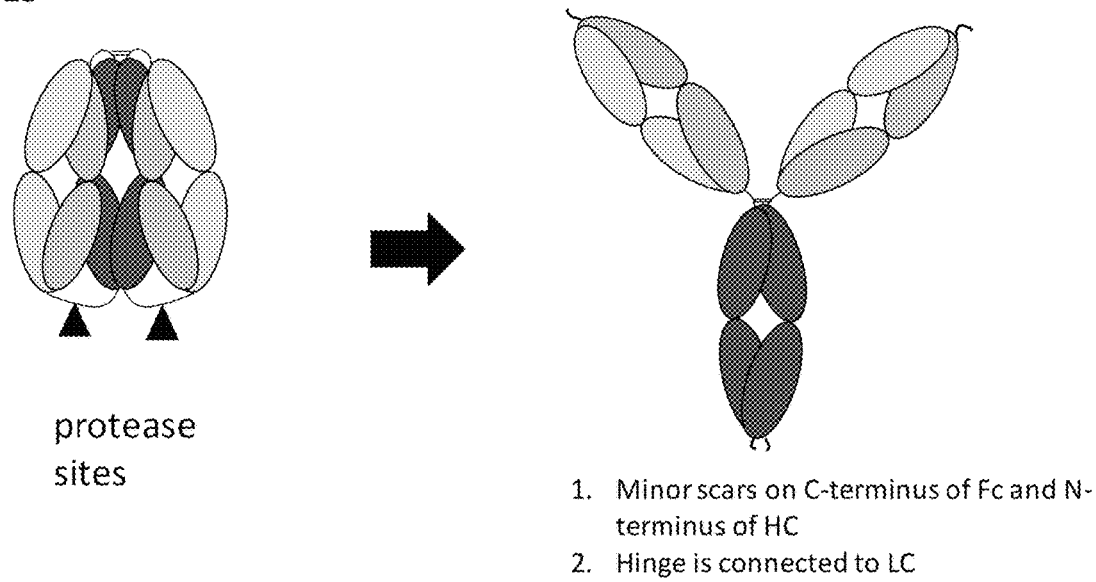
FIG. 23. Cartoon depiction of the Fc switchblade before and after cleavage, where the peptide is antibody-like after cleavage.
Figure 24:
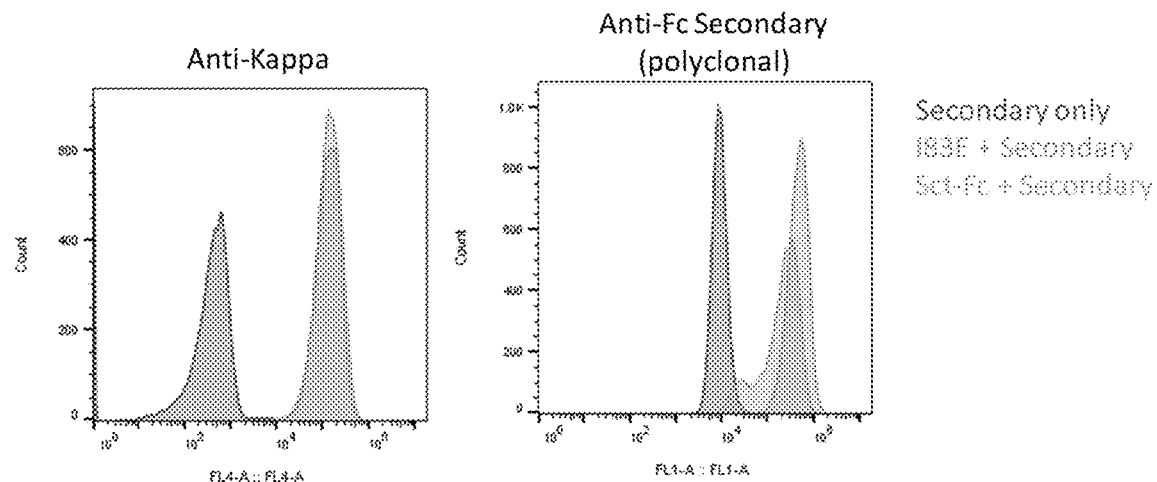
FIG. 24. Some binding sites on the Switch Fc are sterically blocked. Analytical cytometry was used to determine whether the light chain or Fc domains were sterically restricted. The left panel shows the binding interface between the light chain and an anti-kappa antibody is unrestricted. The shift observed upon anti-kappa antibody exposure to trastuzumab and the Fc switchblade is indistinguishable. Using a polyclonal anti-FC antibody shows a different distribution between trastuzumab and the Fc switchblade (right panel). This difference indicates that some members within the polyclonal anti-Fc pool cannot bind to the Fc.
Figure 25:
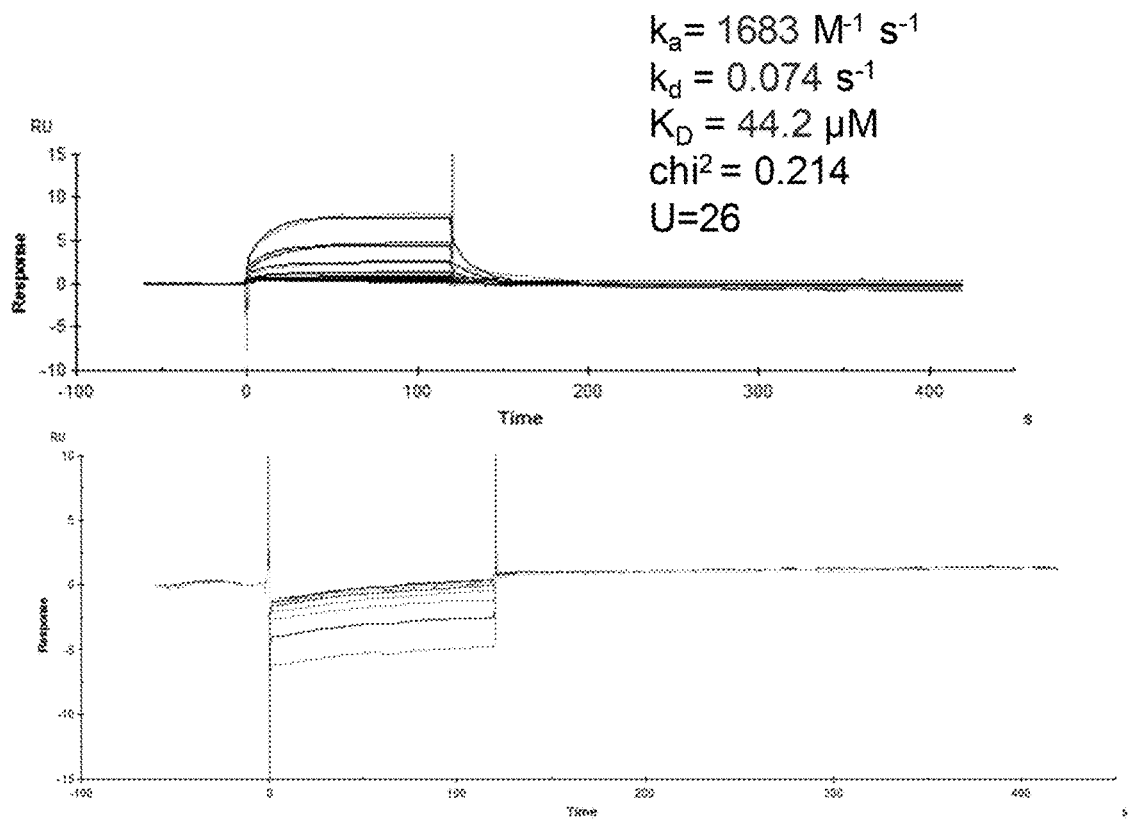
FIG. 25. Only cleaved switch is capable of binding the Fc receptor CD16. A critical interaction, particularly for NK cell activity is between CD16 and the Fc of a therapeutic mAb. Surface plasmon resonance was used to show differential CD16 binding of the FC switchblade before and after protease activation. The top traces show the cleaved FC switchblade binds to CD16. The bottom traces indicate the uncleaved material does not bind to CD16.

As described above the peptides provided herein including embodiments thereof may form a complex, wherein a first peptide is bound to a second peptide through binding of the first Fc dimerizing domain forming part of the first peptide to the second Fc dimerzing domain forming part of the second peptide. Upon binding of the first Fc dimerizing domain to the second Fe dimerizing domain an Fc region is formed and the first peptide and the second peptide form a dimerized peptide complex also referred to herein as "IgG switchblade" or "Ig switchblade." Upon cleavage of the linker connecting the first Fc dimerizing domain with the second protein dimerizing domain and the second Fc dimerzing domain with the fourth protein dimerzing domain, the antibody Fc region, the second ligand binding domain and the third ligand binding domain are no longer occluded and able to bind to their corresponding ligands. Further, upon cleavage, cleaved peptide linker moieties (peptide sequences formed by cleavage of the peptide linker) remain attached to the N-terminus of the second ligand binding domain, the N-terminus of the third ligand binding domain, the C-terminus of the first Fc dimerizing domain and the C-terminus of the second Fc dimerzing domain, respectively. A peptide including cleaved peptide linker moieties formed by cleavage of the second or fifth chemical linker are also referred to herein as "scarred molecules" as shown, for example, in FIG. 21.

In embodiments, the first ligand binding domain is a first Fc dimerzing domain. An "Fc dimerzing domain: as provided herein is a polypeptide capable of forming an antibody Fc region through covalent and non-covalent interaction with a corresponding second Fc dimerzing domain. Therefore, an Fc dimerzing domain may include a CH2 domain and a CH3 domain. The peptides provided herein may include aN Fc dimerzing domain as first ligand binding domain. Where the peptides provided herein including embodiments thereof include an Fc dimerzing domain, the Fc dimerzing of one peptide may bind to the Fc dimerzing of another peptide provided herein and thereby form a peptide dimer complex, which may include, for example, two Fab domains and an antibody Fc region, all of which are sterically occluded.

In embodiments, the first Fc dimerzing domain is bound to a second peptide including: (i) a third protein dimerizing domain bound to a second Fc dimerzing domain through a fourth chemical linker; and (ii) a fourth protein dimerizing domain bound to the second Fc dimerzing domain through a fifth chemical linker; wherein the third protein dimerizing domain is capable of non-covalently binding to the fourth protein dimerizing domain to form a third ligand binding domain; and wherein the first Fc dimerzing domain and the second Fc dimerzing domain are covalently bound together thereby binding the first peptide to the second peptide.

In embodiments, the first protein dimerizing domain and the third protein dimerizing domain are independently an antibody light chain or an antibody heavy chain. In embodiments, the first protein dimerizing domain and the third protein dimerizing domain are independently an antibody light chain. In embodiments, the second protein dimerizing domain and the fourth protein dimerizing domain are independently an antibody heavy chain or an antibody light chain. In embodiments, the second protein dimerizing domain and the fourth protein dimerizing domain are independently an antibody heavy chain.

In embodiments, the fourth chemical linker is bound to the N-terminus of the second Fc dimerzing domain and the fifth chemical linker is bound to the C-terminus of the Fc dimerzing domain. In embodiments, the first linker and the fourth linker are independently a bond. In embodiments, the second linker and the fifth linker are independently a cleavable linker. In embodiments, the second linker and the fifth linker independently include the sequence of SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61 or SEQ ID NO:63. In embodiments, the second linker and the fifth linker independently are the sequence of SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61 or SEQ ID NO:63.

In embodiments, the first peptide and the second peptide are chemically different or the same. In embodiments, the first Fc dimerzing domain includes a first constant heavy chain 2 (CH2) domain and a first constant heavy chain 3 (CH3) domain. In embodiments, the second Fc dimerzing domain includes a second CH2 domain and a second CH3 domain. In embodiments, the first CH2 domain is covalently bound to the second CH2 domain. In embodiments, the first CH2 domain is covalently bound to the second CH2 domain through a disulfide linkage. In embodiments, the first CH3 domain is non-covalently bound to the second CH3 domain. In embodiments, the Fc dimerzing domain and the second Fc dimerzing domain form an antibody Fc region. In embodiments, the second ligand binding domain and the third ligand binding domain are independently a Fab or an scFv. In embodiments, the second ligand binding domain and the third ligand binding domain are a Fab. In embodiments, the second ligand binding domain and the third ligand binding domain are an anti-HER2 Fab.

Any of the ligand binding domains provided herein including embodiments are contemplated for the peptide dimerizing complexes provided herein. Thus, in embodiments, the first protein dimerzing domain and the third protein dimerzing domain include the sequence of SEQ ID NO:4. In embodiments, the second protein dimerzing domain and the fourth protein dimerzing domain include the sequence of SEQ ID NO: 8.

In embodiments, the second constant heavy chain 3 (CH3) domain and the second constant heavy chain 2 (CH2) form part of the sequence of SEQ ID NO:17. In embodiments, the first constant heavy chain 3 (CH3) domain and the first constant heavy chain 2 (CH2) are the polypeptide of the sequence of SEQ ID NO:17. In embodiments, the second constant heavy chain 3 (CH3) domain and the second constant heavy chain 2 (CH2) are the polypeptide of the sequence of SEQ ID NO:17.

The peptide compositions provided herein may be multi-specific and bind two or more ligands. Therefore, the peptide compositions provided herein may include a plurality of ligand binding domains (e.g., a first ligand binding domain, a second ligand binding domain, a third ligand binding domain, a fourth ligand binding domain). Wherein the peptide compositions provided herein include more than two ligand binding domains the first and/or second chemical linker (e.g., first and/or second chemical linker) may be a peptidyl linker and said peptidyl linker may include further ligand binding domains. Thus, in embodiments the first chemical linker and the second chemical linker are independently a peptidyl linker. In embodiments, the first chemical linker further includes a third ligand binding domain. In embodiments, the third ligand binding domain is bound to the first ligand binding domain through a fourth chemical linker. In embodiments, the second chemical linker further includes a fourth ligand binding domain. In embodiments, the fourth ligand binding domain is bound to the first ligand binding domain through a fifth chemical linker. The first ligand binding domain, the second ligand binding domain, the third ligand binding domain and the fourth ligand binding domain may be independently different or the same. Accordingly, the ligand binding domains provided herein, including embodiments thereof, may be chemically different or the same. In embodiments, the peptide includes from the N-terminus to the C-terminus a first protein dimerizing domain, a first chemical linker, a third ligand binding domain, a fourth chemical linker, a first ligand binding domain, a second chemical linker and a second protein dimerizing domain. In embodiments, the peptide includes from the N-terminus to the C-terminus a first protein dimerizing domain, a first chemical linker, a first ligand binding domain, a second chemical linker, a third ligand binding domain, a fourth chemical linker and a second protein dimerizing domain.

The ligand binding domains provided herein (e.g., the first, second, third and fourth ligand binding domain), including embodiments thereof, may bind to the same or a different ligand. Thus, in embodiments, the ligand binding domains provided herein, including embodiments thereof, bind the same ligand. In embodiments, the ligand binding domains provided herein, including embodiments thereof, bind to different ligands from one another. The ligand binding domains provided herein, including embodiments thereof, may bind different regions (e.g., different epitopes) of the same ligand.

In embodiments, the first ligand binding domain, the second ligand binding domain, the third ligand binding domain and the fourth ligand binding domain are independently a tumor binding domain, a T-cell activating domain (e.g., an antibody Fc region formed by the Fc dimerizing domains provided herein) or an interleukin domain.

In embodiments, the first ligand binding domain, the second ligand binding domain, the third ligand binding domain and the fourth ligand binding domain independently include a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain or a 41BB binding domain. In embodiments, the first ligand binding domain, the second ligand binding domain, the third ligand binding domain and the fourth ligand binding domain independently are a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain or a 41BB binding domain. A CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain or a 41BB binding domain as provided herein refer to peptide domains capable of binding CD3, CD16, Her2, CD123, CD20, tumor-associated glycoprotein 72 (TAG72), carcinoembryonic antigen (CEA), CD252, glucocorticoid-induced tumor necrosis factor receptor (GITR), 41BB or any functional fragment, or homolog thereof.

In embodiments, the first ligand binding domain, the second ligand binding domain, the third ligand binding domain and the fourth ligand binding domain compete for antigen-binding with, specifically bind to the same antigen or epitope as, and/or contains one, more, or all CDRs (or CDRs comprising at least at or about 75, 80, 85, 90, 91, 92, 93, 94, 95, 96, 97, 98, or 99% identity to the CDRs), e.g., including a heavy chain CDR 1, 2, and/or 3 and/or a light chain CDR1, 2, and/or 3, of one or more known antibodies, including any commercially available antibody, such as abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benraliuzmab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, Fbta05, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, Trbs07, ustekinumab, visilizumab, votumumab, zalutumumab, and/or brodalumab; and/or anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, the antibody produced by the hybridoma 10B5 (see Edelson & Unanue, *Curr Opin Immunol*, 2000 August;

12(4):425-31), B6H12.2 (abcam) or other anti-CD47 antibody (see Chao et al., *Cell,* 142, 699-713, Sep. 3, 2010).

In embodiments, the first ligand binding domain, the second ligand binding domain, the third ligand binding domain and the fourth ligand binding domain independently specifically bind to an antigen selected from the group consisting of CA-125, glycoprotein (GP) IIb/IIIa receptor, TNF-alpha, CD52, TAG-72, Carcinoembryonic antigen (CEA), interleukin-6 receptor (IL-6R), IL-2, interleukin-2 receptor a-chain (CD25), CD22, B-cell activating factor, interleukin-5 receptor (CD125), VEGF, VEGF-A, CD30, IL-1beta, prostate specific membrane antigen (PSMA), CD3, EpCAM, EGF receptor (EGFR), MUC1, human interleukin-2 receptor, Tac, RANK ligand, a complement protein, e.g., $C_5$, EpCAM, CD11a, e.g., human CD11a, an integrin, e.g., alpha-v beta-3 integrin, vitronectin receptor alpha v beta 3 integrin, HER2, neu, CD3, CD15, CD20 (small and/or large loops), Interferon gamma, CD33, CA-IX, TNF alpha, CTLA-4, carcinoembryonic antigen, IL-5, CD3 epsilon, CAM, Alpha-4-integrin, IgE, e.g., IgE Fc region, an RSV antigen, e.g., F protein of respiratory syncytial virus (RSV), TAG-72, NCA-90 (granulocyte cell antigen), IL-6, GD2, GD3, IL-12, IL-23, IL-17, CTAA16.88, IL13, interleukin-1 beta, beta-amyloid, IGF-1 receptor (IGF-1R), delta-like ligand 4 (DLL4), alpha subunit of granulocyte macrophage colony stimulating factor receptor, hepatocyte growth factor, IFN-alpha, nerve growth factor, IL-13, CD326, Programmed cell death 1 ligand 1 (PD-L1, a.k.a. CD274, B7-H1), CD47, and CD137.

In embodiments, the first ligand binding domain includes a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain or a 41BB binding domain. In embodiments, the first ligand binding domain is a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain or a 41BB binding domain. In embodiments, the first ligand binding domain includes a CD33 binding domain. In embodiments, the first ligand binding domain includes an PSMA binding domain. In embodiments, the first ligand binding domain includes the sequence of SEQ ID NO:6. In embodiments, the first ligand binding domain is the sequence of SEQ ID NO:6. In embodiments, the first ligand binding domain includes the sequence of SEQ ID NO: 11. In embodiments, the first ligand binding domain is the sequence of SEQ ID NO: 11. In embodiments, the first ligand binding domain includes the sequence of SEQ ID NO: 13. In embodiments, the first ligand binding domain is the sequence of SEQ ID NO: 13.

In embodiments, the second ligand binding domain includes a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain or a 41BB binding domain. In embodiments, the second ligand binding domain is a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain, a CD33 binding domain, a PSMA binding domain or a 41BB binding domain. In embodiments, the second ligand binding domain includes the sequences of SEQ ID NOs:4 and 8. In embodiments, the second ligand binding domain is from 5' to 3' the sequence of SEQ ID NOs:4 and 8. In embodiments, the second ligand binding domain includes the sequences of SEQ ID NOs:9 and 15. In embodiments, the second ligand binding domain is from 5' to 3' the sequence of SEQ ID NOs:9 and 15.

In embodiments, the third ligand binding domain includes a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain or a 41BB binding domain. In embodiments, the third ligand binding domain is a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain, a CD33 binding domain, a PSMA binding domain or a 41BB binding domain. In embodiments, the third ligand binding domain includes the sequence of SEQ ID NO: 6. In embodiments, the third ligand binding domain is the sequence of SEQ ID NO: 6. In embodiments, the third ligand binding domain includes the sequence of SEQ ID NO: 11. In embodiments, the third ligand binding domain is the sequence of SEQ ID NO: 11. In embodiments, the third ligand binding domain includes the sequence of SEQ ID NO: 13. In embodiments, the third ligand binding domain is the sequence of SEQ ID NO: 13.

In embodiments, the fourth ligand binding domain includes a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain or a 41BB binding domain. In embodiments, the fourth ligand binding domain is a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain, a CD33 binding domain, a PSMA binding domain or a 41BB binding domain. In embodiments, the fourth ligand binding domain includes the sequence of SEQ ID NO:6 In embodiments, the fourth ligand binding domain is the sequence of SEQ ID NO: 6. In embodiments, the fourth ligand binding domain includes the sequence of SEQ ID NO: 11. In embodiments, the fourth ligand binding domain is the sequence of SEQ ID NO: 11. In embodiments, the fourth ligand binding domain includes the sequence of SEQ ID NO: 13. In embodiments, the fourth ligand binding domain is the sequence of SEQ ID NO: 13.

In embodiments, the first ligand binding domain, the third ligand binding domain and the fourth ligand binding domain independently include a single domain antibody domain.

In embodiments, the first chemical linker, the second chemical linker, the third chemical linker, the fourth chemical linker, and the fifth chemical linker are independently a covalent linker or a non-covalent linker. In embodiments, the first chemical linker, the second chemical linker, the third chemical linker, the fourth chemical linker, and the fifth chemical linker are independently a peptidyl linker. In embodiments, the first chemical linker, the second chemical linker, the third chemical linker, the fourth chemical linker, and the fifth chemical linker are independently a cleavable peptide linker. In embodiments, the first chemical linker, the second chemical linker, the third chemical linker, the fourth chemical linker, and the fifth chemical linker are independently an enzymatically cleavable linker. In embodiments, the first chemical linker, the second chemical linker, the third chemical linker, the fourth chemical linker, and the fifth chemical linker are independently a protease cleavable linker.

In embodiments, the first chemical linker, the second chemical linker, the third chemical linker, the fourth chemical linker, and the fifth chemical linker are independently a cleavable peptide linker, including a protease cleavage site. A "cleavage site" as used herein, refers to a recognizable site for cleavage of a portion of a linker described herein. Thus, a cleavage site may be found in the sequence of a cleavable peptide linker as described herein, including embodiments thereof. In embodiments, the cleavage site is an amino acid sequence that is recognized and cleaved by a cleaving agent (e.g., a peptidyl sequence). Exemplary cleaving agents include proteins, enzymes, DNAzymes, RNAzymes, metals, acids, and bases. In embodiments, the protease cleavage site is a tumor-associated protease cleavage site. A "tumor-associated protease cleavage site" as provided herein is an amino acid sequence recognized by a protease, whose expression is specific for a tumor cell or tumor cell environment thereof. In embodiments, the protease cleavage site is a matrix metalloprotease (MMP) cleavage site, a disintegrin and metalloprotease domain-containing (ADAM) metalloprotease cleavage site, a prostate specific antigen (PSA) protease cleavage site, a urokinase-type plasminogen activator (uPA) protease cleavage site, a membrane type serine protease 1 (MT-SP1) protease cleavage site or a legumain protease cleavage site. In embodiments, the matrix metalloprotease (MMP) cleavage site is a MMP 9 cleavage site, a MMP 13 cleavage site or a MMP 2 cleavage site. In embodiments, the disintegrin and metalloprotease domain-containing (ADAM) metalloprotease cleavage site is a ADAM 9 metalloprotease cleavage site, a ADAM 10 metalloprotease cleavage site or a ADAM 17 metalloprotease cleavage site. In embodiments, the cleavable peptide linker includes the sequence set forth by SEQ ID NO:5.

Further exemplary cleavage sites include the cleavage site of ABHD12, ADAM12, ABHD12B, ABHD13, ABHD17A, ADAM19, ADAM20, ADAM21, ADAM28, ADAM30, ADAM33, ADAM8, ABHD17A, ADAMDEC1, ADAMTS1, ADAMTS10, ADAMTS12, ADAMTS13, ADAMTS14, ADAMTS15, ADAMTS16, ADAMTS17, ADAMTS18, ADAMTS19, ADAMTS2, ADAMTS20, ADAMTS3, ADAMTS4, ABHD17B, ADAMTS5, ADAMTS6, ADAMTS7, ADAMTS8, ADAMTS9, ADAMTSL1, ADAMTSL2, ADAMTSL3, ABHD17C, ADAMTSL5, ASTL, BMP1, CELA1, CELA2A, CELA2B, CELA3A, CELA3B, ADAM10, ADAM15, ADAM17, ADAM9, ADAMTS4, CTSE, CTSF, ADAMTSL4, CMA1, CTRB1, CTRC, CTSO, CTR1, CTSA, CTSW, CTSB, CTSC, CTSD, ESP1, CTSG, CTSH, GZMA, GZMB, GZMH, CTSK, GZMM, CTSL, CTSS, CTSV, CTSZ, HTRA4, KLK10, KLK11, KLK13, KLK14, KLK2, KLK4, DPP4, KLK6, KLK7, KLKB1, ECE1, ECE2, ECEL1, MASP2, MEP1A, MEP1B, ELANE, FAP, GZMA, MMP11, GZMK, HGFAC, HPN, HTRA1, MMP11, MMP16, MMP17, MMP19, HTRA2, MMP20, MMP21, HTRA3, HTRA4, KEL, MMP23B, MMP24, MMP25, MMP26, MMP27, MMP28, KLK5, MMP3, MMP7, MMP8, MMP9, LGMN, LNPEP, MASP1, PAPPA, PAPPA2, PCSK1, NAPSA, PCSK5, PCSK6, MME, MMP1, MMP10, PLAT, PLAU, PLG, PRSS1, PRSS12, PRSS2, PRSS21, PRSS3, PRSS33, PRSS4, PRSS55, PRSS57, MMP12, PRSS8, PRSS9, PRTN3, MMP13, MMP14, ST14, TMPRSS10, TMPRSS11A, TMPRSS11D, TMPRSS11E, TMPRSS11F, TMPRSS12, TMPRSS13, MMP15, TMPRSS15, MMP2, TMPRSS2, TMPRSS3, TMPRSS4, TMPRSS5, TMPRSS6, TMPRSS7, TMPRSS9, NRDC, OVCH1, PAMR1, PCSK3, PHEX, TINAG, TPSAB1, TPSD1, or TPSG1.

In embodiments, the first chemical linker, the second chemical linker, the third chemical linker, the fourth chemical linker, and the fifth chemical linker independently include the sequence set forth by SEQ ID NO:7. In embodiments, the first chemical linker, the second chemical linker, the third chemical linker, the fourth chemical linker, and the fifth chemical linker independently include the sequence set forth by SEQ ID NO:10. In embodiments, the first chemical linker, the second chemical linker, the third chemical linker, the fourth chemical linker, and the fifth chemical linker independently include the sequence set forth by SEQ ID NO:12. In embodiments, the first chemical linker, the second chemical linker, the third chemical linker, the fourth chemical linker, and the fifth chemical linker independently include the sequence set forth by SEQ ID NO:14. In embodiments, the first chemical linker, the second chemical linker, the third chemical linker, the fourth chemical linker, and the fifth chemical linker independently are the sequence set forth by SEQ ID NO: 7. In embodiments, the first chemical linker, the second chemical linker, the third chemical linker, the fourth chemical linker, and the fifth chemical linker independently are the sequence set forth by SEQ ID NO:10. In embodiments, the first chemical linker, the second chemical linker, the third chemical linker, the fourth chemical linker, and the fifth chemical linker independently are the sequence set forth by SEQ ID NO:12. In embodiments, the first chemical linker, the second chemical linker, the third chemical linker, the fourth chemical linker, and the fifth chemical linker independently are the sequence set forth by SEQ ID NO:14. In embodiments, the first chemical linker, the second chemical linker, the third chemical linker, the fourth chemical linker, and the fifth chemical linker independently include the sequence set forth by SEQ ID NO:5.

The chemical linkers provided herein, including embodiments thereof, may have different lengths (e.g., include varying numbers of amino acid residues). Thus, in embodiments, the first chemical linker, the second chemical linker, the third chemical linker, the fourth chemical linker, and the fifth chemical linker independently have a length of about 0 to about 15 amino acid residues. In embodiments, the first chemical linker, the second chemical linker, the third chemical linker, the fourth chemical linker, and the fifth chemical linker independently have a length of about 0 to about 10 amino acid residues. In embodiments, the first chemical linker, the second chemical linker, the third chemical linker, the fourth chemical linker, and the fifth chemical linker independently have a length of about 0 to about 9 amino acid residues. In embodiments, the first chemical linker, the second chemical linker, the third chemical linker, the fourth chemical linker, and the fifth chemical linker independently have a length of about 0 to about 8 amino acid residues. In embodiments, the first chemical linker, the second chemical linker, the third chemical linker, the fourth chemical linker, and the fifth chemical linker independently have a length of about 0 to about 7 amino acid residues. In embodiments, the first chemical linker, the second chemical linker, the third chemical linker, the fourth chemical linker, and the fifth chemical linker independently have a length of about 0 to about 6 amino acid residues. In embodiments, the first chemical linker, the second chemical linker, the third chemical linker, the fourth chemical linker, and the fifth chemical linker independently have a length of about 0 to about 5 amino acid residues. In embodiments, the first chemical linker, the second chemical linker, the third chemical linker, the fourth chemical linker, and the fifth chemical linker independently have a length of about 0 to about 4 amino acid residues. In embodiments, the first chemical linker, the second chemical linker, the third chemical linker, the fourth chemical linker, and the fifth chemical linker independently have a length of about 0 to about 3 amino acid residues. In embodiments, the first chemical linker, the second chemical linker, the third chemical linker, the fourth chemical linker, and the fifth chemical linker independently have a length of about 0 to about 2 amino acid residues. In embodiments, the first chemical linker, the second chemical linker, the third chemical linker, the fourth chemical linker, and the fifth chemical linker independently have a length of about 0 to about 1 amino acid residues.

In embodiments, the first chemical linker, the second chemical linker, the third chemical linker, the fourth chemical linker, and the fifth chemical linker independently have a length of 0 to 15 amino acid residues. In embodiments, the first chemical linker, the second chemical linker, the third chemical linker, the fourth chemical linker, and the fifth chemical linker independently have a length of 0 to 10 amino acid residues. In embodiments, the first chemical linker, the second chemical linker, the third chemical linker, the fourth chemical linker, and the fifth chemical linker independently have a length of 0 to 9 amino acid residues. In embodiments, the first chemical linker, the second chemical linker, the third chemical linker, the fourth chemical linker, and the fifth chemical linker independently have a length of 0 to 8 amino acid residues. In embodiments, the first chemical linker, the second chemical linker, the third chemical linker, the fourth chemical linker, and the fifth chemical linker independently have a length of 0 to 7 amino acid residues. In embodiments, the first chemical linker, the second chemical linker, the third chemical linker, the fourth chemical linker, and the fifth chemical linker independently have a length of 0 to 6 amino acid residues. In embodiments, the first chemical linker, the second chemical linker, the third chemical linker, the fourth chemical linker, and the fifth chemical linker independently have a length of 0 to 5 amino acid residues. In embodiments, the first chemical linker, the second chemical linker, the third chemical linker, the fourth chemical linker, and the fifth chemical linker independently have a length of 0 to 4 amino acid residues. In embodiments, the first chemical linker, the second chemical linker, the third chemical linker, the fourth chemical linker, and the fifth chemical linker independently have a length of 0 to 3 amino acid residues. In embodiments, the first chemical linker, the second chemical linker, the third chemical linker, the fourth chemical linker, and the fifth chemical linker independently have a length of 0 to 2 amino acid residues. In embodiments, the first chemical linker, the second chemical linker, the third chemical linker, the fourth chemical linker, and the fifth chemical linker independently have a length of 0 to 1 amino acid residues.

In embodiments, the first chemical linker, the second chemical linker, the third chemical linker, the fourth chemical linker, and the fifth chemical linker independently have a length of 15 amino acid residues. In embodiments, the first chemical linker, the second chemical linker, the third chemical linker, the fourth chemical linker, and the fifth chemical linker independently have a length of 10 amino acid residues. In embodiments, the first chemical linker, the second chemical linker, the third chemical linker, the fourth chemical linker, and the fifth chemical linker independently have a length of 9 amino acid residues. In embodiments, the first chemical linker, the second chemical linker, the third chemical linker, the fourth chemical linker, and the fifth chemical linker independently have a length of 8 amino acid residues. In embodiments, the first chemical linker, the second chemical linker, the third chemical linker, the fourth chemical linker, and the fifth chemical linker independently have a length of 7 amino acid residues. In embodiments, the first chemical linker, the second chemical linker, the third chemical linker, the fourth chemical linker, and the fifth chemical linker independently have a length of 6 amino acid residues. In embodiments, the first chemical linker, the second chemical linker, the third chemical linker, the fourth chemical linker, and the fifth chemical linker independently have a length of 5 amino acid residues. In embodiments, the first chemical linker, the second chemical linker, the third chemical linker, the fourth chemical linker, and the fifth chemical linker independently have a length of 4 amino acid residues. In embodiments, the first chemical linker, the second chemical linker, the third chemical linker, the fourth chemical linker, and the fifth chemical linker independently have a length of 3 amino acid residues. In embodiments, the first chemical linker, the second chemical linker, the third chemical linker, the fourth chemical linker, and the fifth chemical linker independently have a length of 2 amino acid residues. In embodiments, the first chemical linker, the second chemical linker, the third chemical linker, the fourth chemical linker, and the fifth chemical linker independently have a length of 1 amino acid residues. In embodiments, the first chemical linker, the second chemical linker, the third chemical linker, the fourth chemical linker, and the fifth chemical linker independently have a length of 0 amino acid residues.

In embodiments, the peptide includes from the N-terminus to the C-terminus a variable light chain domain, a constant light chain domain, a first chemical linker, a single domain antibody, a second chemical linker, a variable heavy chain domain, and a constant heavy chain domain.

In embodiments, the peptide includes from the N-terminus to the C-terminus a variable light chain domain, a constant light chain domain, a first chemical linker, a first Fc dimerizing domain, a second chemical linker, a variable heavy chain domain, and a constant heavy chain domain. In further embodiments, the first chemical linker is a bond. In further embodiments, the first Fc dimerizing domain is bound (covalently and/or non-covalently) to a second Fc dimerzing domain of a second peptide.

In embodiments, the peptide includes from the N-terminus to the C-terminus a variable heavy chain domain, a constant heavy chain domain, a first chemical linker, a single domain antibody, a second chemical linker, a variable light chain domain, and a constant light chain domain. In further embodiments, the first chemical linker is a bond.

In embodiments, the peptide includes from the N-terminus to the C-terminus a variable heavy chain domain, a constant heavy chain domain, a first chemical linker, a first Fc dimerizing domain, a second chemical linker, a variable light chain domain, and a constant light chain domain.

In one embodiment, the peptide includes from the N-terminus to the C-terminus a trastuzumab variable light chain domain, a trastuzumab constant light chain domain, a first peptidyl linker, an anti-CD16 single domain antibody, a second peptidyl linker, a trastuzumab variable heavy chain domain, and a trastuzumab constant heavy chain domain. A "trastuzumab light chain" as provided herein refers to an antibody light chain capable of binding the same epitope as any of the recombinant or naturally-occurring forms of the trastuzumab light chain or variants or homologs thereof that comprise the trastuzumab light chain (e.g. within at least 50%, 80%, 90%, 95%, 96%, 97%, 98%, 99% or 100% activity compared to trastuzumab). Likewise, a "trastuzumab heavy chain" as provided herein refers to an antibody heavy chain capable of binding activity as any of the recombinant or naturally-occurring forms of the trastuzumab heavy chain or variants or homologs thereof that comprise the trastuzumab heavy chain (e.g. within at least 50%, 80%, 90%, 95%, 96%, 97%, 98%, 99% or 100% activity compared to trastuzumab). In one embodiment, the peptide includes the sequence of SEQ ID NO: 1. In one embodiment, the peptide is the sequence of SEQ ID NO:1. In embodiments, the peptide includes from the N-terminus to the C-terminus a trastuzumab variable light chain domain, a trastuzumab constant light chain domain, an Fc region, a trastuzumab variable heavy chain domain, and a trastuzumab constant heavy chain domain. In embodiments, the peptide includes from the N-terminus to the C-terminus a trastuzumab variable light chain domain, a trastuzumab constant light chain domain, a first Fc dimerzing domain, a trastuzumab variable heavy chain domain, and a trastuzumab constant heavy chain domain. In embodiments, the peptide includes the sequence of SEQ ID NO:74. In embodiments, the peptide is the sequence of SEQ ID NO:74.

In one embodiment, the peptide includes from the N-terminus to the C-terminus an anti-CD3 variable light chain domain, an anti-CD3 constant light chain domain, a first peptidyl linker, an anti-Her2 single domain antibody, a second peptidyl linker, anti-CD3 variable heavy chain domain, and anti-CD3 constant heavy chain domain.

In one embodiment, the peptide includes from the N-terminus to the C-terminus an anti-CD3 variable light chain domain, an anti-CD3 constant light chain domain, a first peptidyl linker, an anti-CD20 single domain antibody, a second peptidyl linker, anti-CD3 variable heavy chain domain, and anti-CD3 constant heavy chain domain.

In one embodiment, the peptide includes from the N-terminus to the C-terminus an anti-CD3 variable light chain domain, an anti-CD3 constant light chain domain, a first peptidyl linker, an anti-TAG72 single domain antibody, a second peptidyl linker, anti-CD3 variable heavy chain domain, and anti-CD3 constant heavy chain domain.

In one embodiment, the peptide includes from the N-terminus to the C-terminus an anti-CD3 variable light chain domain, an anti-CD3 constant light chain domain, a first peptidyl linker, an anti-CEA single domain antibody, a second peptidyl linker, anti-CD3 variable heavy chain domain, and anti-CD3 constant heavy chain domain.

In one embodiment, the peptide includes from the N-terminus to the C-terminus an anti-CD16 variable light chain domain, an anti-CD16 constant light chain domain, a first peptidyl linker, an anti-Her2 single domain antibody, a second peptidyl linker, anti-CD16 variable heavy chain domain, and anti-CD16 constant heavy chain domain.

In one embodiment, the peptide includes from the N-terminus to the C-terminus an anti-CD16 variable light chain domain, an anti-CD16 constant light chain domain, a first peptidyl linker, an anti-CD20 single domain antibody, a second peptidyl linker, anti-CD16 variable heavy chain domain, and anti-CD16 constant heavy chain domain.

In one embodiment, the peptide includes from the N-terminus to the C-terminus an anti-CD16 variable light chain domain, an anti-CD16 constant light chain domain, a first peptidyl linker, an anti-TAG72 single domain antibody, a second peptidyl linker, anti-CD16 variable heavy chain domain, and anti-CD16 constant heavy chain domain.

In one embodiment, the peptide includes from the N-terminus to the C-terminus an anti-CD16 variable light chain domain, an anti-CD16 constant light chain domain, a first peptidyl linker, an anti-CEA single domain antibody, a second peptidyl linker, anti-CD16 variable heavy chain domain, and anti-CD16 constant heavy chain domain.

In one embodiment, the peptide includes from the N-terminus to the C-terminus an anti-CD3 variable light chain domain, an anti-CD3 constant light chain domain, a first peptidyl linker, an anti-PSMA single domain antibody, a second peptidyl linker, anti-CD3 variable heavy chain domain, and anti-CD3 constant heavy chain domain.

In one embodiment, the peptide includes from the N-terminus to the C-terminus an anti-4-1BB variable light chain domain, an anti-4-1BB constant light chain domain, a first peptidyl linker, an anti-Her2 affibody antibody, a second peptidyl linker, anti-4-1BB variable heavy chain domain, and anti-4-1BB constant heavy chain domain.

In an aspect is provided a peptide including: (i) a first protein dimerizing domain bound to a first multivalent ligand binding domain through a first chemical linker; and (ii) a second protein dimerizing domain bound to the first multivalent ligand binding domain through a second chemical linker; wherein the first protein dimerizing domain is capable of non-covalently binding to the second protein dimerizing domain to form a second ligand binding domain. In embodiments, the first ligand binding domain (first multivalent ligand binding domain) is different from the second ligand binding domain.

The term "multivalent ligand binding domain" as provided herein refers to a multivalent polypeptide including at least two binding domains, wherein each of the binding domains binds to a ligand. The ligand binding domains included in the multivalent ligand binding domain may be bound to each other non-covalently or covalently through chemical linkers. In embodiments, the first multivalent ligand binding domain includes two or more ligand binding domains connected through one or more chemical linkers. In embodiments, the two or more ligand binding domains bind different ligands. In embodiments, the two or more ligand binding domains bind the same ligand. In embodiments, the two or more ligand binding domains bind different epitopes of the same ligand. In embodiments, the multivalent ligand binding domain is capable of binding tumor necrosis factor receptor (TNFR). In embodiments, the multivalent ligand binding domain is a trimeric peptide domain.

In embodiments, the first multivalent ligand binding domain includes a third ligand binding domain and a fourth ligand binding domain. In embodiments, the third ligand binding domain is bound to the fourth ligand binding domain through a third chemical linker. In embodiments, the third ligand binding domain is bound to the first protein dimerizing domain through the first chemical linker and the fourth ligand binding domain is bound to the second protein dimerizing domain through the second chemical linker. In embodiments, the peptide includes from the N-terminus to the C-terminus a first protein dimerizing domain, a first chemical linker, a third ligand binding domain, a third chemical linker, a fourth ligand binding domain, a second chemical linker and a second protein dimerizing domain.

As described above the first multivalent ligand binding domain, the second ligand binding domain, the third ligand binding domain and the fourth ligand binding domain are independently different or the same. In embodiments, the first multivalent ligand binding domain, the second ligand binding domain, the third ligand binding domain and the fourth ligand binding domain are chemically the same or different. In embodiments, the first multivalent ligand binding domain, the second ligand binding domain, the third ligand binding domain and the fourth ligand binding domain bind the same ligand. In embodiments, the first multivalent ligand binding domain, the second ligand binding domain, the third ligand binding domain and the fourth ligand binding domain bind different ligands. In embodiments, the first multivalent ligand binding domain, the second ligand binding domain, the third ligand binding domain and the fourth ligand binding domain bind different regions (e.g., epitopes) of the same ligand.

In embodiments, the first multivalent ligand binding domain, the second ligand binding domain, the third ligand binding domain and the fourth ligand binding domain are independently a tumor binding domain, a T-cell activating domain or an interleukin domain.

In embodiments, the first multivalent ligand binding domain, the second ligand binding domain, the third ligand binding domain and the fourth ligand binding domain independently include a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain, a CD33 binding domain, a PSMA binding domain or a 41BB binding domain.

In embodiments, the first multivalent ligand binding domain includes a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain, a CD33 binding domain, a PSMA binding domain or a 41BB binding domain.

In embodiments, the second ligand binding domain includes a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain, a CD33 binding domain, a PSMA binding domain or a 41BB binding domain.

In embodiments, the third ligand binding domain includes a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain, a CD33 binding domain, a PSMA binding domain or a 41BB binding domain.

In embodiments, the fourth ligand binding domain includes a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain, a CD33 binding domain, a PSMA binding domain or a 41BB binding domain.

In embodiments, the peptide includes from the N-terminus to the C-terminus a variable light chain domain, a constant light chain domain, a first chemical linker, a first single domain antibody, a second chemical linker, a second single domain antibody, a third chemical linker, a variable heavy chain domain, and a constant heavy chain domain.

In embodiments, the peptide includes from the N-terminus to the C-terminus a variable light chain domain, a constant light chain domain, a first chemical linker, a first single domain antibody, a second chemical linker, a second single domain antibody, a third chemical linker, a third single domain antibody, a fourth chemical linker, a variable heavy chain domain, and a constant heavy chain domain.

In embodiments, the peptide includes from the N-terminus to the C-terminus a variable light chain domain, a constant light chain domain, a first chemical linker, a first single domain antibody, a second chemical linker, a second single domain antibody, a third chemical linker, a third single domain antibody, a fourth chemical linker, a fourth single domain antibody, a fifth chemical linker, a variable heavy chain domain, and a constant heavy chain domain.

In embodiments, the peptide includes from the N-terminus to the C-terminus a variable heavy chain domain, a constant heavy chain domain, a first chemical linker, a first single domain antibody, a second chemical linker, a second single domain antibody, a third chemical linker, a variable light chain domain, and a constant light chain domain.

In embodiments, the peptide includes from the N-terminus to the C-terminus a variable heavy chain domain, a constant heavy chain domain, a first chemical linker, a first single domain antibody, a second chemical linker, a second single domain antibody, a third chemical linker, a third single domain antibody, a fourth chemical linker, a variable light chain domain, and a constant light chain domain.

In embodiments, the peptide includes from the N-terminus to the C-terminus a variable heavy chain domain, a constant heavy chain domain, a first chemical linker, a first single domain antibody, a second chemical linker, a second single domain antibody, a third chemical linker, a third single domain antibody, a fourth chemical linker, a fourth single domain antibody, a fifth chemical linker, a variable light chain domain, and a constant light chain domain.

In one embodiment, the peptide includes from the N-terminus to the C-terminus an anti-CD33 variable light chain domain, an anti-CD33 constant light chain domain, a first peptidyl linker, an anti-CD20 single domain antibody, a second peptidyl linker, an anti-CD123 single domain antibody, a third peptidyl linker, an anti-CD33 variable heavy chain domain, and an anti-CD33 constant heavy chain domain. In one embodiment, the peptide sequence includes the sequence of SEQ ID NO:2. In one embodiment, the peptide sequence is the sequence of SEQ ID NO:2.

It is contemplated that the peptides provided herein, including embodiments thereof, may be useful for multiple types of immunotherapy (e.g., CAR therapy). Accordingly, in embodiments, the peptide provided herein, including embodiments thereof, forms part of a chimeric antigen receptor (CAR). Where the peptide provided herein forms part of a CAR, the remainder of the peptide may be bound to the transmembrane domain of the CAR through said second protein dimerizing domain.

In embodiments, the CAR includes a transmembrane domain. A "transmembrane domain" as provided herein refers to a polypeptide forming part of a biological membrane. The transmembrane domain provided herein is capable of spanning a biological membrane (e.g., a cellular membrane) from one side of the membrane through to the other side of the membrane. In embodiments, the transmembrane domain spans from the intracellular side to the extracellular side of a cellular membrane. Transmembrane domains may include non-polar, hydrophobic residues, which anchor the proteins provided herein including embodiments thereof in a biological membrane (e.g., cellular membrane of a T cell). Any transmembrane domain capable of anchoring the proteins provided herein including embodiments thereof are contemplated. In embodiments, the transmembrane domain is L-selectin. The term "L-selectin" as provided herein includes any of the recombinant or naturally-occurring forms of the L-selectin protein, also known as CD62L, or variants or homologs thereof that maintain L-selectin activity (e.g. within at least 50%, 80%, 90%, 95%, 96%, 97%, 98%, 99% or 100% activity compared to L-selectin). In embodiments, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring L-selectin polypeptide. In embodiments, L-selectin is the protein as identified by the NCBI sequence reference GI.262206315, homolog or functional fragment thereof. Non-limiting examples of transmembrane domains include, the transmembrane domains of CD28, CD8, CD4 or CD3-zeta.

In embodiments, the transmembrane domain is a CD4 transmembrane domain. The term "CD4 transmembrane domain" as provided herein includes any of the recombinant or naturally-occurring forms of the transmembrane domain of T-cell surface glycoprotein CD4, or variants or homologs thereof that maintain CD4 transmembrane domain activity (e.g. within at least 50%, 80%, 90%, 95%, 96%, 97%, 98%, 99% or 100% activity compared to the CD4 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD4 transmembrane domain polypeptide. In embodiments, CD4 is the protein as identified by UniProt reference number P01730 or a variant or homolog having substantial identity thereto.

In embodiments, the transmembrane domain is a CD28 transmembrane domain. The term "CD28 transmembrane domain" as provided herein includes any of the recombinant or naturally-occurring forms of the transmembrane domain of CD28, or variants or homologs thereof that maintain CD28 transmembrane domain activity (e.g. within at least 50%, 80%, 90%, 95%, 96%, 97%, 98%, 99% or 100% activity compared to the CD28 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 transmembrane domain polypeptide. In embodiments, CD28 is the protein as identified by the NCBI sequence reference GI:340545506, homolog or functional fragment thereof.

In embodiments, the CAR includes a spacer region. In embodiments, the spacer region is between the transmembrane domain and the peptide as provided herein, including embodiments thereof. A "spacer region" as provided herein is a polypeptide connecting the peptide as provided herein, including embodiments thereof, with the transmembrane domain. In embodiments, the spacer region connects the heavy chain constant region of the peptide provided herein, including embodiments thereof, with the transmembrane domain. In embodiments, the spacer region includes an Fc region. In embodiments, the spacer region is an Fc region. Examples of spacer regions contemplated for the peptide compositions provided herein include without limitation, immunoglobulin molecules or fragments thereof (e.g., IgG1, IgG2, IgG3, IgG4) and immunoglobulin molecules or fragments thereof (e.g., IgG1, IgG2, IgG3, IgG4) including mutations affecting Fc receptor binding. In embodiments, the spacer region is a hinge region. In embodiments, the spacer region is an IgG4 hinge region. In embodiments, the spacer region is a modified IgG4 hinge region.

In embodiments, the CAR further includes an intracellular co-stimulatory signaling domain. An "intracellular co-stimulatory signaling domain" as provided herein includes amino acid sequences capable of providing co-stimulatory signaling in response to binding of an antigen to the antibody region provided herein including embodiments thereof. In embodiments, the signaling of the co-stimulatory signaling domain results in production of cytokines and proliferation of the T cell expressing the same. In embodiments, the intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain. In embodiments, the intracellular co-stimulatory signaling domain is a CD28 intracellular co-stimulatory signaling domain. In embodiments, the intracellular co-stimulatory signaling domain is a 4-1BB intracellular co-stimulatory signaling domain. In embodiments, the intracellular co-stimulatory signaling domain is a ICOS intracellular co-stimulatory signaling domain. In embodiments, the intracellular co-stimulatory signaling domain is an OX-40 intracellular co-stimulatory signaling domain.

In embodiments, the CAR further includes an intracellular T-cell signaling domain. An "intracellular T-cell signaling domain" as provided herein includes amino acid sequences capable of providing primary signaling in response to binding of an antigen to the peptide provided herein including embodiments thereof. In embodiments, the signaling of the intracellular T-cell signaling domain results in activation of the T cell expressing the same. In embodiments, the signaling of the intracellular T-cell signaling domain results in proliferation (cell division) of the T cell expressing the same. In embodiments, the signaling of the intracellular T-cell signaling domain results expression by said T cell of proteins known in the art to characteristic of activated T cell (e.g., CTLA-4, PD-1, CD28, CD69). In embodiments, the intracellular T-cell signaling domain includes the signaling domain of the zeta chain of the human CD3 complex. In embodiments, the intracellular T-cell signaling domain is a CD3 (intracellular T-cell signaling domain.

In embodiments, the CAR further includes a linker domain. In embodiments, the linker domain is between the transmembrane domain and the intracellular T-cell signaling domain. In embodiments, the linker domain is between the intracellular T-cell signaling domain and the intracellular co-stimulatory signaling domain. In embodiments, the linker domain includes the sequence GGCGG or GGG.

In embodiments, the CAR further includes a self-cleaving peptidyl sequence. In embodiments, the self-cleaving peptidyl linker sequence is a T2A sequence or a 2A sequence. In embodiments, the self-cleaving peptidyl linker sequence is a T2A sequence. In embodiments, the self-cleaving peptidyl linker sequence is a 2A sequence.

In embodiments, the peptide forms part of a T cell.

Nucleic Acid Compositions

In an aspect is provided an isolated nucleic acid encoding a peptide as described herein, including embodiments thereof. The nucleic acid provided herein, including embodiments thereof, may be loaded into an expression vector such that the nucleic acid may be delivered to cells. Thus, in an aspect, an expression vector including the nucleic acid provided herein, including embodiments thereof, is provided. It is contemplated that the nucleic acid may be loaded into any expression vector useful for delivering the nucleic acid to cells either in vivo or in vitro. It is further contemplated that viruses, for example, lentivirus and onco-retrovirus, may serve as suitable expression vectors. Accordingly, in embodiments, the expression vector is a viral vector. In embodiments, the viral vector is a lentiviral vector or an onco-retroviral vector. In embodiments, the viral vector is a lentiviral vector. In embodiments, the viral vector is an onco-retroviral vector. In embodiments, the virus is a lentivirus or an onco-retrovirus. In embodiments, the virus is a lentivirus. In embodiments, the virus is an onco-retrovirus.

Pharmaceutical Compositions

In an aspect is provided a pharmaceutical composition including a peptide as described herein, including embodiments thereof, and pharmaceutically acceptable excipient Methods of Treatment The compositions provided herein, including embodiments thereof, are contemplated as providing effective treatments for diseases such as cancer. Thus, in an aspect is provided a method including administering to a subject in need thereof a therapeutically effective amount of a peptide as described herein, including embodiments thereof.

Methods of Detecting

The compositions provided herein, including embodiments thereof, are contemplated as diagnostic tools for detecting cancer in vivo. Thus, in an aspect is provided a method of detecting a cancer cell in a subject in need thereof the method including administering to a subject in need thereof a peptide as described herein, including embodiments thereof and a detecting agent. In embodiments, the agent is a labeled peptide. In embodiments, the labeled peptide is bound by the peptide provided herein including embodiments thereof thereby detecting the cancer in said subject.

In embodiments, the peptide includes a detectable moiety. In embodiments, the detectable moiety is bound (covalently or non-covalently) to the second ligand biding domain. In embodiments, the second ligand binding domain includes a detectable moiety.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: Fab-Based Switch Blades

A single chain Fab is created where the linker between the light chain and the heavy chain is a single domain anti-CD16 Fab with a tumor specific protease site between the C-terminus of the light chain and N-terminus of the anti-CD16. Cleavage of this protease substrate will free the anti-CD16 to bind to its target, the FcRIIIa/b, creating an activated 'bispecific' NK cell engager (FIG. 1).

Previously, investigators developed a single chain Fab, much like a single chain Fv (scFv) (presumably for CAR T cells to take advantage of the affinity and stability of a Fab, but avoid the assembly of the Fab due to different expression levels of the each chain). This indicates that it is possible to make a single chain Fab using a longer flexible linker. This concept is significantly different.

Using the structure of the trastuzumab Fab, Applicants decided on the following order: light chain—protease site—antiCD16—linker—heavy chain (SEQ ID NO:1). The order of the Fab light and heavy chains could be flipped. Broadly, Applicants can swap out the anti-CD16 for other molecules such as IL2, anti-CD3 (scFv), lipocalin, etc. Applicants anticipate that some of these constructs would need to be optimized to 'improve' steric restriction (before activation) and that the cleavage site may need to be optimized for the micro-environment. Applicants note that they can add the Fc to make this a full IgG. Applicants also note that this could be employed on a CAR T cell, could be spit out of a disease tropic cell.

Example 2: Molecular Switchblades

Disease-activated, bi-specific antibodies to improve the safety of immunotherapeutics and other applications. Through protein engineering, a biologic (e.g., bispecific T-cell engager) is sterically occluded as part of a single chain Fab/mAb. A protease site within the chain is cut by a disease-specific protease thereby removing the steric constraint and activating the molecule.

Adding a domain between the light and heavy chains has not been done to the best of Applicants' knowledge. Furthermore, PK/PD issues can be addressed, as well as Immune Related Adverse side effects, which are a significant clinical issue (up to 50% grade 3/4 events). In addition, manufacturing issues can be significantly reduced, which are one of the biggest hurdles in producing a clinical candidate. This technology is applicable to CAR T cells and other biologics. Applicants have generated a proof of concept. Applicants will optimize the steric occlusion and activation.

Adverse side effects remain a problem with all therapeutics. Manufacturing of multispecific biologics also remains an industry wide challenge. Thus, disease site specificity and ease of manufacturing across multiple biologics is attractive to all pharma/biotech for multiple indications.

Molecular switchblades can address two unmet needs: (1) production of bispecific molecules and (2) adverse side effects. Bispecifics can be used as therapeutics by targeting two antigens simultaneously (e.g., Her2/Her3), sequestering multiple ligands (e.g., TNF-α/IL17A), transport (e.g., transferrin arm to cross the blood brain barrier (BBB)), bispecific T cell engagers (one arm to CD3/CD16 of T cells or NK cells and the other arm to tumor target (e.g., CD19)). There are 47 CD3/NK cell engagers in clinical trials.

Figure 4:
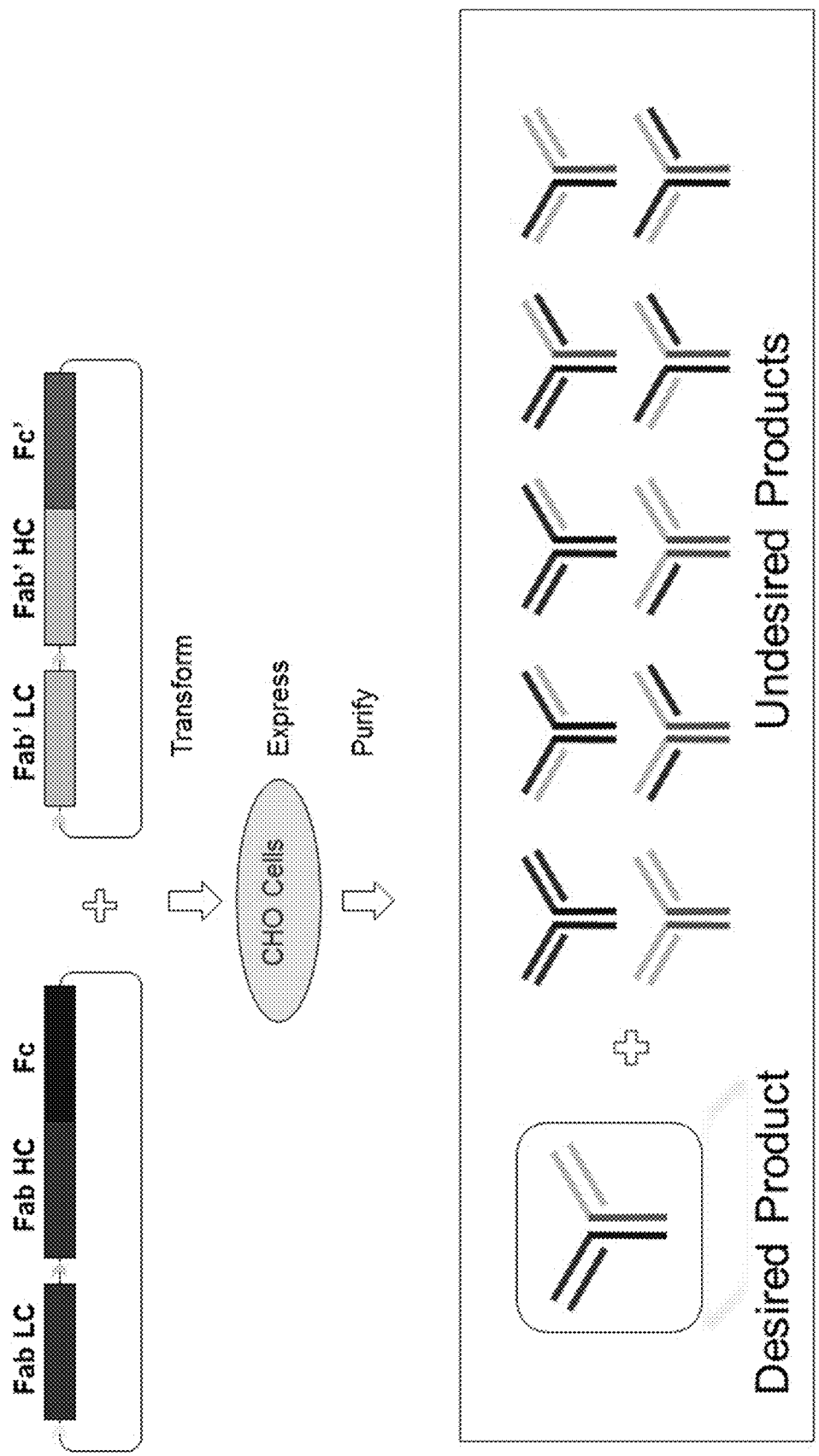
FIG. 4. Schematic illustrating traditional bispecific mAb generation.
Figure 5:
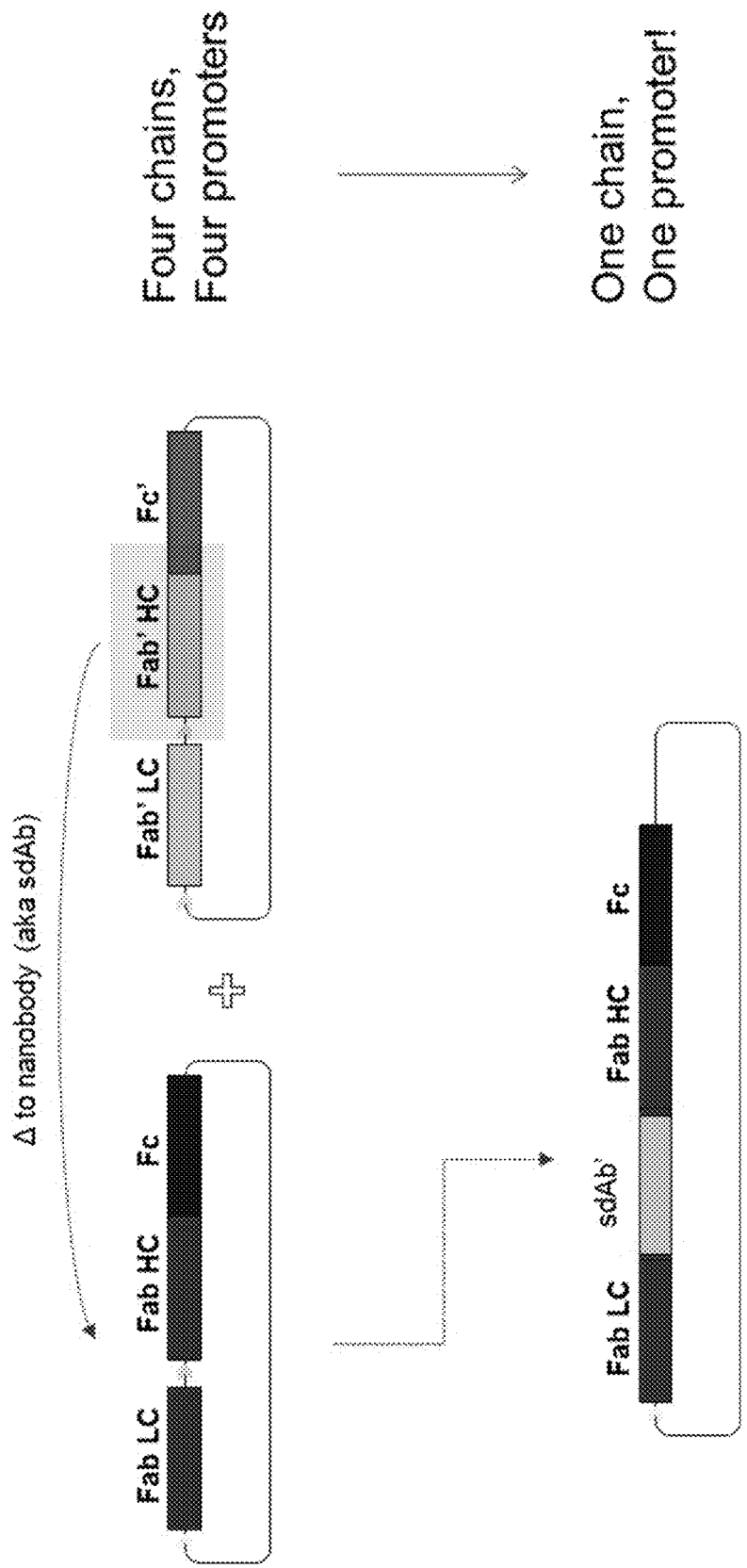
FIG. 5. Schematic illustrating Applicants' novel method of generating bispecifics (peptide compositions provided herein also referred to herein as switchblade or bionic binders). In the new method, only one chain and one promoter are required for expression of the peptides.
Figure 6:
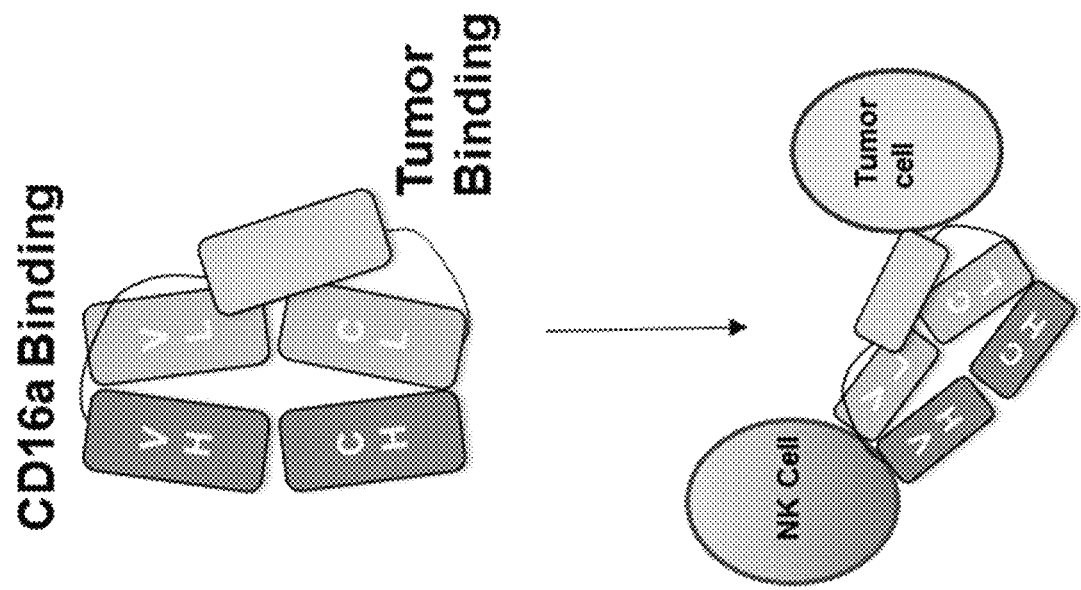
FIG. 6. Exemplary representation of peptides provided herein and modes of action. The peptides depicted include a first and a second ligand binding domain connected through a first and second chemical linker and both ligand binding domains are constitutively active (able to bind to their respective ligand) and do not require cleavage of one of the chemical linkers to be able to bind to their respective ligand. They are also referred to herein as "bionics." Alternatively, the peptide includes a cleavable linker (first or second chemical linker) and unless this linker is cleaved the first ligand binding domain remains occluded and does not bind to its respective ligand. Peptides including a cleavable linker and a first ligand binding domain which is occluded unless the linker is cleaved are also referred to herein as "switchblade."
Figure 6:
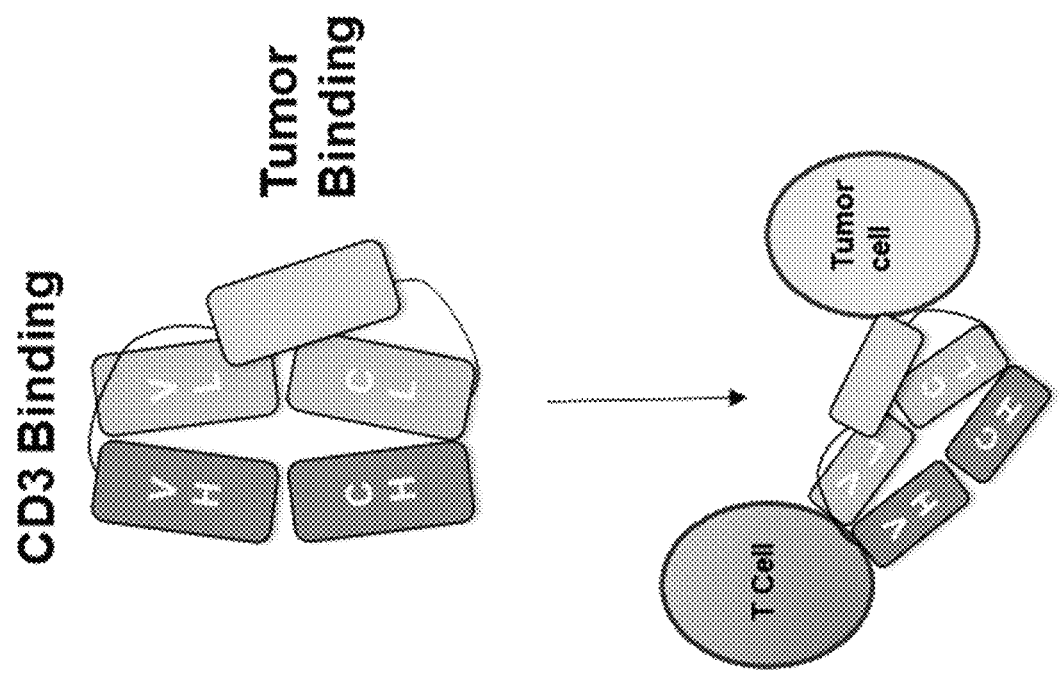
Figures 7, 8:
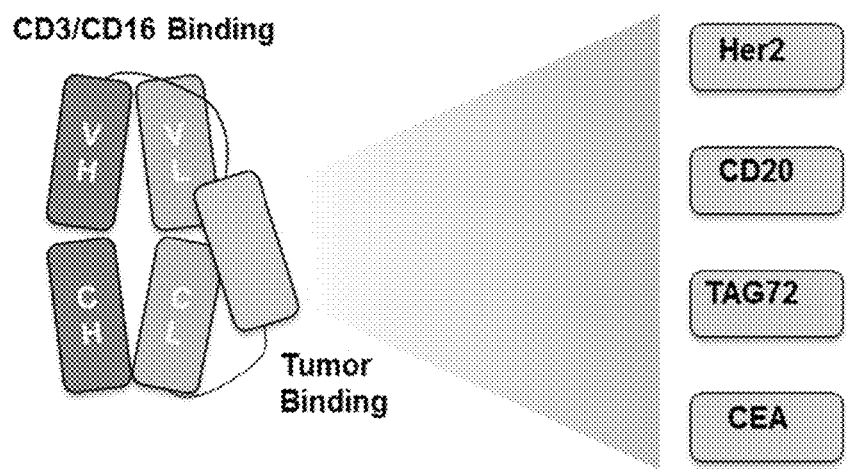
FIG. 7. Exemplary representation of peptides provided herein including nanobody options for tumor binding (e.g., Her2, CD20, TAG72, and CEA). The peptides depicted include a first and a second ligand binding domain connected through a first and second chemical linker and both ligand binding domains are constitutively active (able to bind to their respective ligands). The first ligand binding domain in FIG. 7 are nanobodies capable of binding Her2, CD20, TAG72 or CEA, while the second ligand binding domain are an anti-CD3 Fab or an anti-CD16 Fab.
FIG. 8. Exemplary representation of peptides provided herein including other immune-engaging antibodies (e.g., T cell activators (e.g., OX40, GITR, 41BB; left image) and interleukins (right image)). The peptides depicted include a first and a second ligand binding domain connected through a first and second chemical linker and both ligand binding domains are constitutively active (able to bind to their respective ligands). The first ligand binding domain in FIG. 8 are T-cell activators such as OX40, GITR and 4-1BB, while the second ligand binding domain binds a tumor antigen.

Traditional bispecific mAb generation requires 4 different genes that need to be assembled properly, which can be problematic (FIG. 4). Other technologies to create bispecific mAbs include heavy chain pairing, which relies on knobs-in-holes technology to help Fc pairing, however this may reduce stability; light chain 'knobs-n-holes'; irrelevant light chains (shift all binding to heavy chain); CrossFabs; κ-/λ-bodies (shift all binding to light chains/irrelevant heavy chain); and scaffolds such as DVDs and fusions of scFvs. Because there is such a demand to make bispecifics there have been a tremendous number of engineering efforts to make them. The new technology presented herein, including embodiments thereof, may be the fastest means to get to the clinic. This new technology moves from using 4 chains and 4 promoters to 1 chain and 1 promoter (FIG. 5). In FIG. 5, it can be seen that the heavy chain is changed to a nanobody, also referred to as a single domain antibody (sdAb), and inserted between the heavy and light chain. Even without tumor activation (e.g., disease site activation), the bispecific T cell engagers (BiTEs) are tremendously useful (FIG. 6). Many nanobodies for many targets are already available for targeting an array of tumors (FIG. 7).

Other immune-engaging antibodies can be rapidly engineered (FIG. 8). 41BB and other agonist have attracted a lot of attention. Many mAbs have not been very effective. The idea is that the mAbs need to be clustered by macrophages through the Fc interaction to induce the signal. However, this likely leads to liver toxicity (in animal models as well). Switching out the Fc with a Fab/IgG that recognizes a highly expressed tumor associated antigen can effectively replace the clustering while mitigating liver toxicity. Applicants have started with OX40. The DNA will be cloned into the trastuzumab Fab.

Disease Site Activation.

There has been observed a 1000× difference between N-terminal and C-terminal fusion, strongly suggesting that access to CDRs affects affinity and that access can be achieved by protease activation. Thus, geometry plays an important role.

Figure 2:
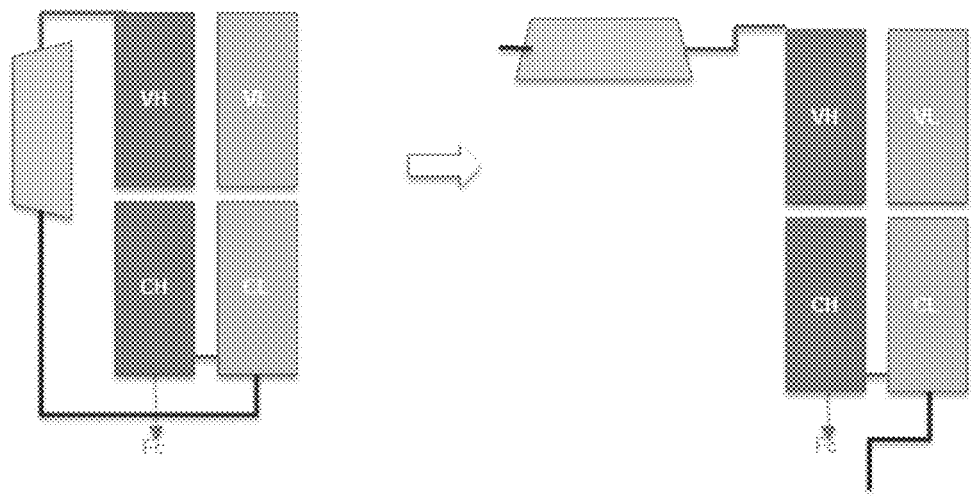
FIG. 2. Cartoon of a Fab-based switchblade including an Fc domain sterically inactive (left cartoon) and active (right cartoon) following cleavage. Shown is a peptide provided herein including from the N-terminus to the C-terminus: an antibody light chain (first protein dimerizing domain), a first chemical linker, a first ligand binding domain, a second chemical linker and and an antibody heavy chain (second protein dimerzing domain). The left panel is a representation of the uncleaved peptide, while the right panel shows the peptide after proteolytic cleavage of the first chemical linker. The gray arrow at the bottom denotes binding of antibody heavy chain to the Fc region.

FIG. 2 shows an example of a method of action of the disease activated bispecific Fab.

Note that there is a naturally occurring disulfide bond found between the light and heavy chains that ensures the Fab stays together after cleavage.

Figure 9A:
FIGS. 9A-9B.
Figure 9B:
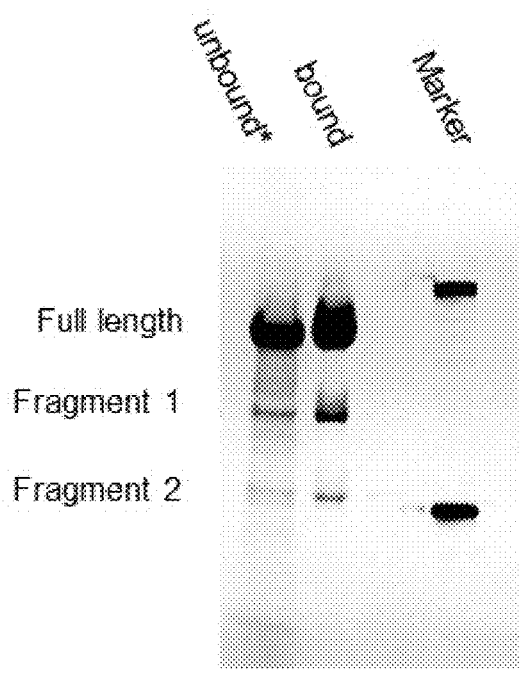
Figure 10A:
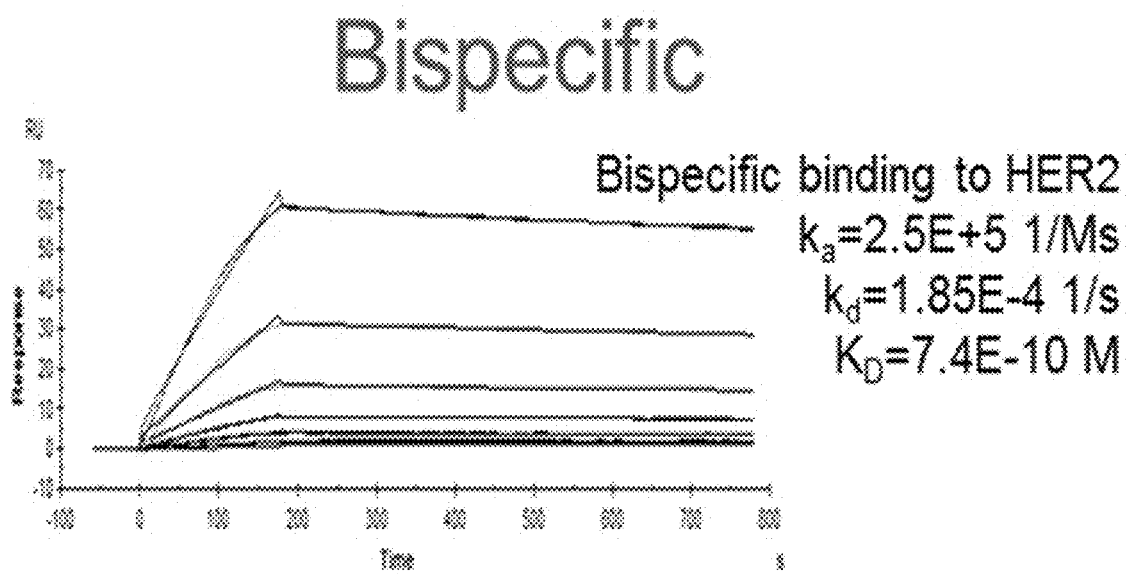
FIGS. 10A-10D. Surface plasmon resonance traces comparing antigen binding behavior of nanobody and Fab.
Figure 10B:
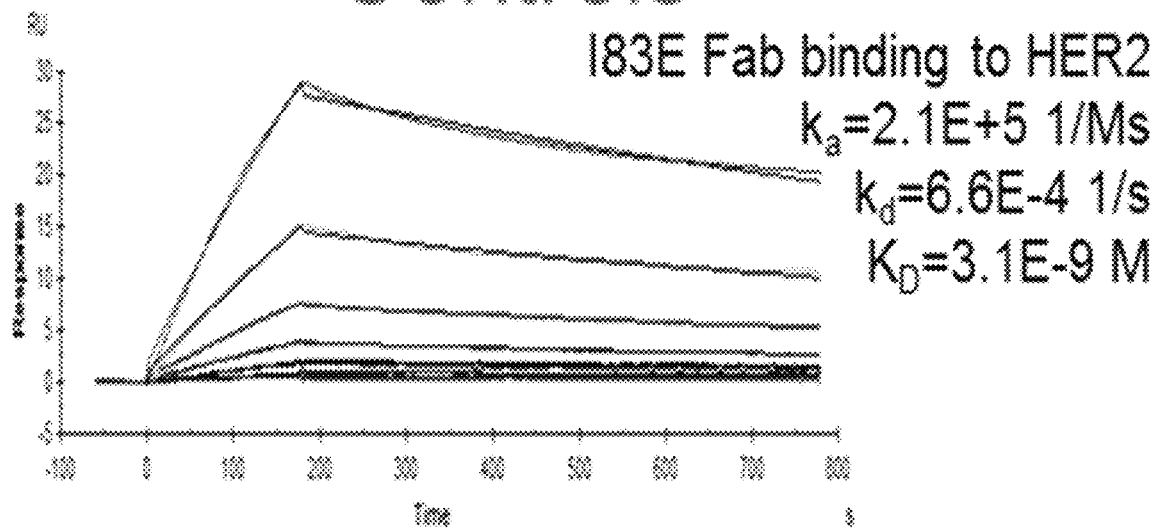
Figure 10C:
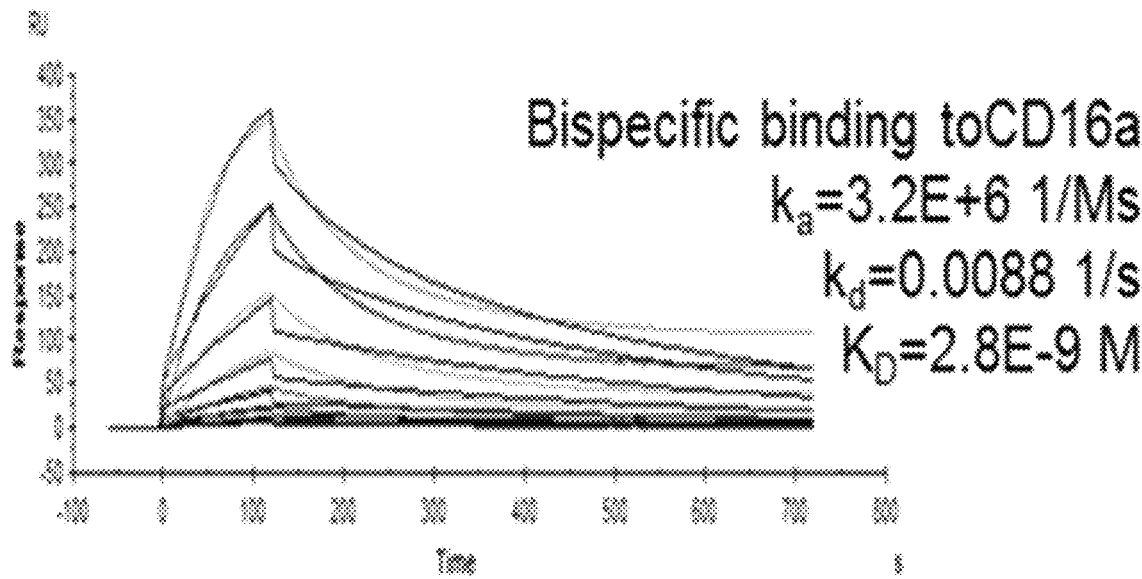
Figure 10D:
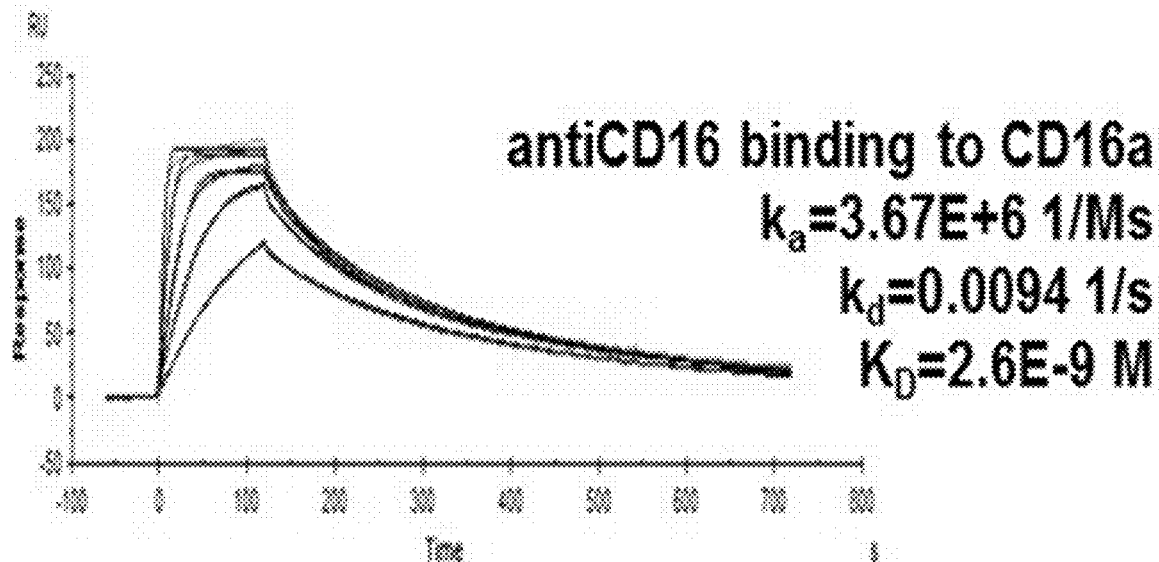

FIG. 9A shows the order of an example construct. This construct was synthesized and purified as a 'normal' mAb. For the unbound sample, so much material was produced that the purification column was saturated immediately, preventing the retention of additional material in the media (FIG. 9B). It was estimated that ~1-3 grams/L was produced through transient transfection. This is ~10 times better than Applicants' very best expressing mAb and 10-40 mg/L is respected place to start (n.b., samples on gel are derived from unconcentrated media (FIG. 9B)). The main fragment has been isolated.

Insertion of a nanobody between the light and heavy chain does not affect antigen binding of the Fab or the nanobody (FIGS. 10A-10D). This indicates that the engineering does not affect the binding affinity. Applicants will optimize the linker to control the local conformation.

Figure 11:
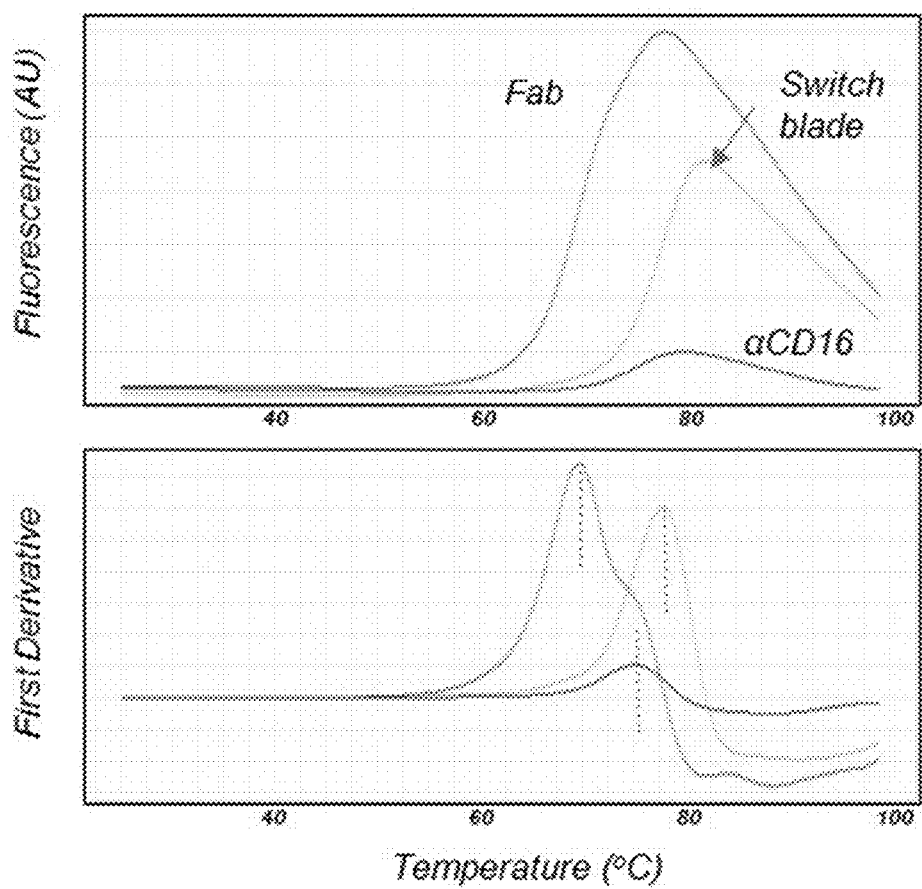
FIG. 11. Differential scanning fluorometry. Plots show effect of temperature on stability of the construct and the individual components (αCD16 is a nanobody. Top plot shows fluorescence as a function of temperature and bottom plot shows the first derivative of the fluorescence traces as a function of temperature. See also Table 1.

The current switchblade is stable (Table 1, FIG. 11). Most bispecifics lower the stability. Knobs-on-holes originally created by Genentech to improve the pairing of the Fc lowers the melting temperature by 15° C. Applicants observe an increase ~3 degrees considered significant for many mAb engineering efforts.

TABLE 1

Melting temperature for constructs.

| Construct | Melting Temp (° C.) | Std Error (° C.) |
|---|---|---|
| Fab only | 69.6 | 0.0 |
| αCD16 | 75.2 | 0.02 |
| Switchblade | 78.0 | 0.03 |

Figure 12A:
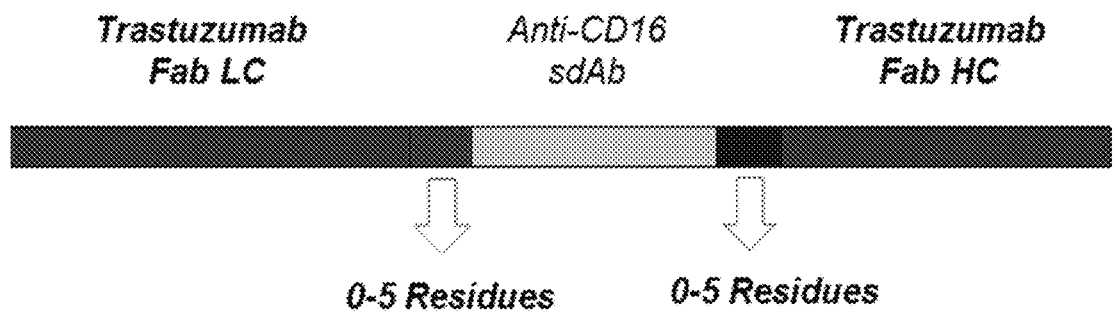
FIG. 12A-12B.
Figure 12B:
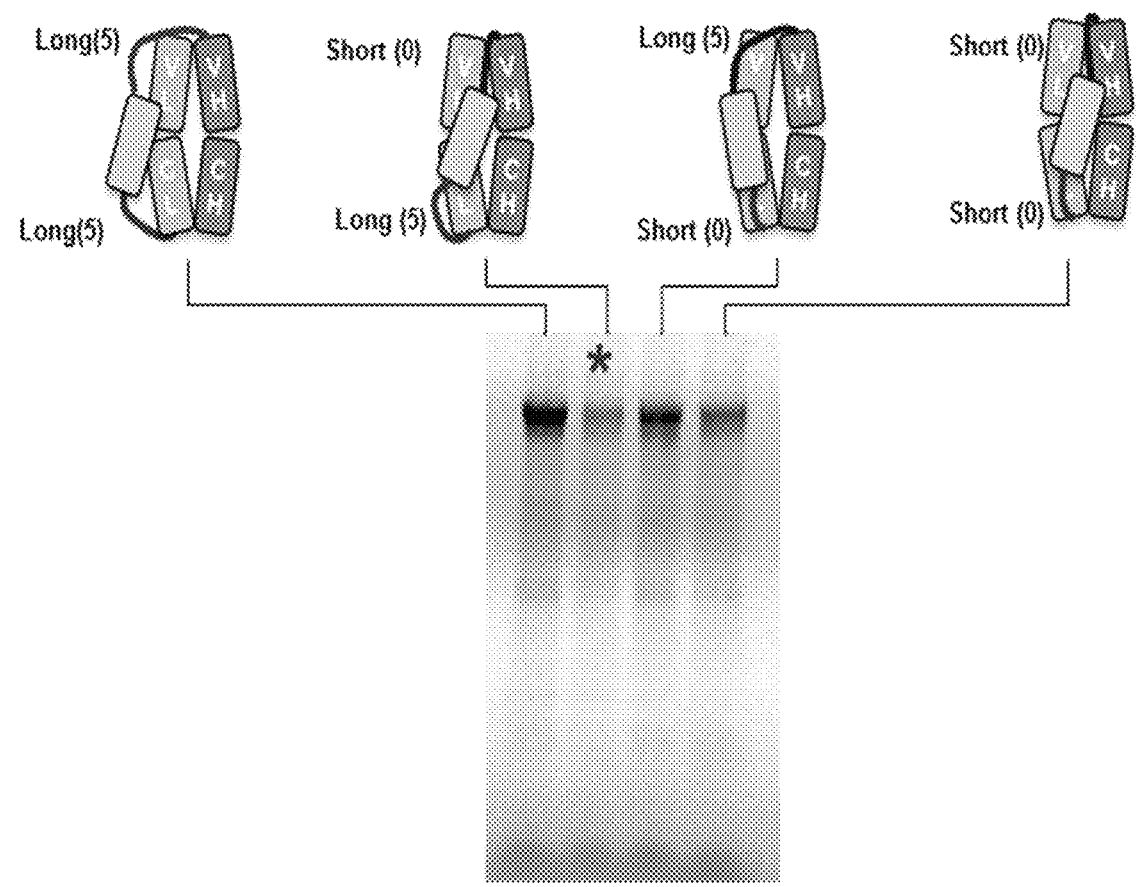

FIG. 12A shows examples of the parameters for positioning the nanobody domain. All 36 constructs have been made and the extreme constructs have been expressed (FIG. 12B). DNA and construction of other switchblades targeting other clinically relevant targets have been initiated (e.g., anti-CD3 (fab) and Tag72, as well as OX40). IL2 has been constructed. 31 other constructs are also being expressed.

Figure 13:
FIG. 13. Cartoon showing embodiment of a peptide provided herein including a multimeric ligand binding domain including an anti-CD20 and anti-CD123 domain and an anti-CD33 Fab (SEQ ID NOs:2 and 3).
Figure 14:
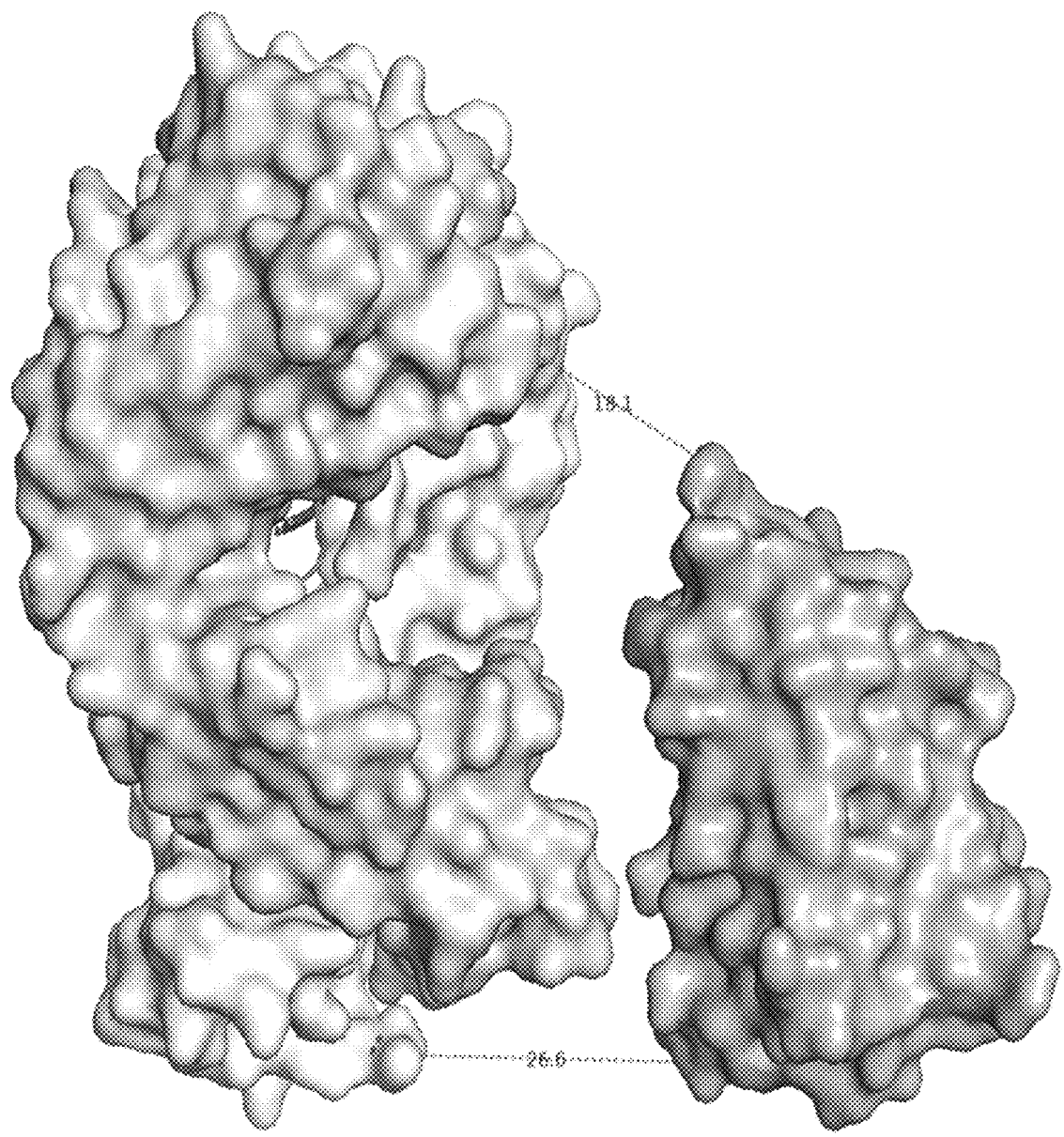
FIG. 14. Structure of an embodiment of a peptide provided herein. This is a simple modelling exercise. Shown is the distance between the C- and N-termini of the Fab and biologic (nanobody; first ligand binding domain). Short peptides can be used for as first and/or second linker for the peptides provided herein and the length and composition of the linker can be altered to sterically occlude the binding site of the inserted biologic (first ligand binding domain).
Figure 15A:
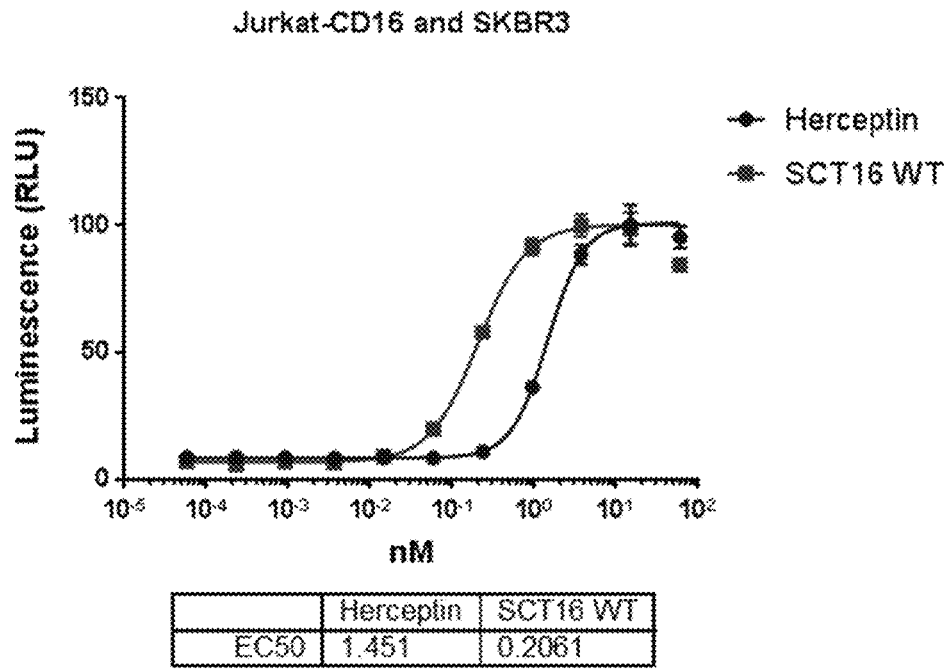
FIG. 15A-15C.
Figure 15B:
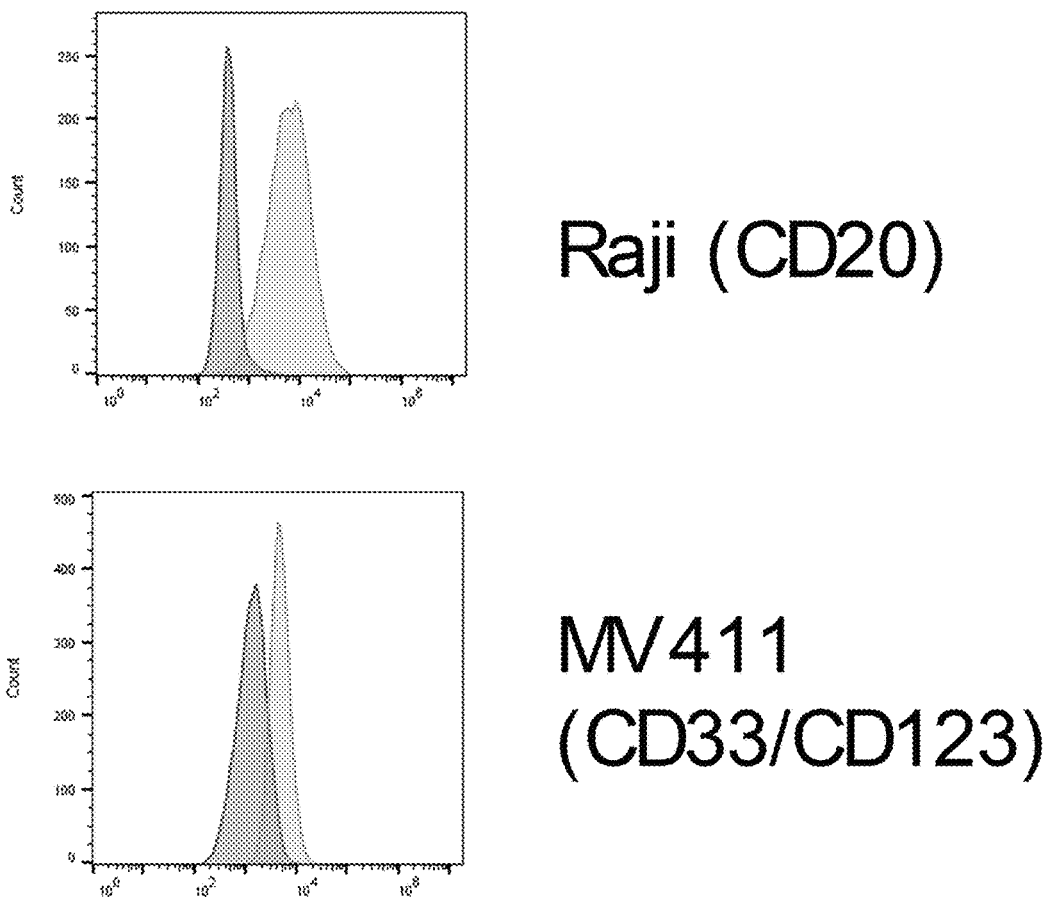
Figure 15C:
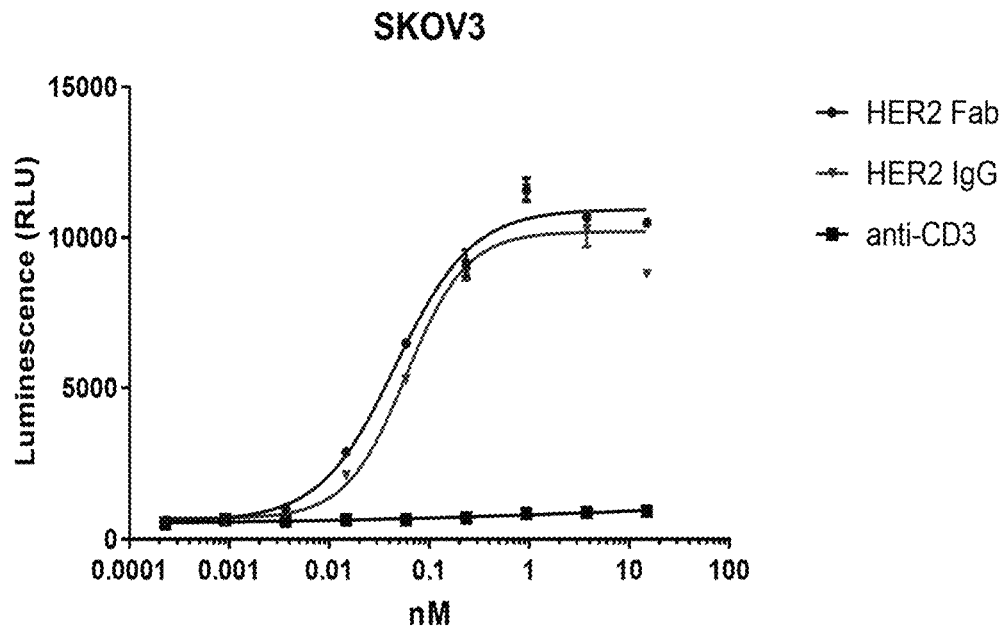
Figure 16:
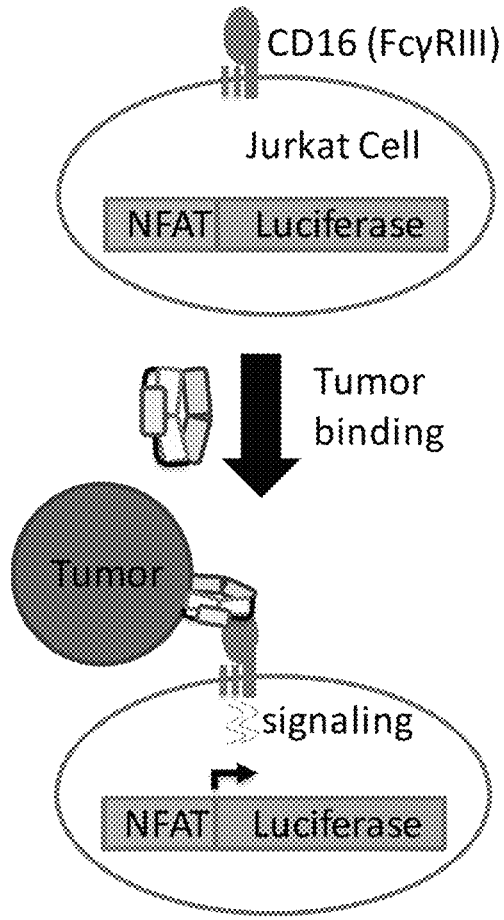
FIG. 16. Jurkat activation assay of anti-HER2 Fab-anti-CD16 nanobody. Cell based assay used to test activation, in vitro. Jurkat cells expressing luciferase under the control of the NFAT promoter were transduced with FcgRIIIa. When a synapse is formed between the tumor cells and the Jurkat cells, luciferase is produced as a result of NFAT activation. No luciferase is produced without tumor cells or antibody. Likewise, the parental Jurkat cells (i.e. without the FCgRIIIa gene) also won't produce luciferase in the presence of antibody.

Applicants are also constructing an anti-CD33/CD20/CD123 Fab loop (SEQ ID NOs:2 and 3; FIG. 13). This was made to be inserted into a CAR T Cell (e.g., there is no effector function).

Applicants will further establish tolerance/boundaries by generating 384 Fab variants, purify, and characterize thermal stability and binding affinity/kinetics to CD3/CD16 and to TAA (e.g., anti-CEA nanobody and others). Applicants will also add three different tumor-associated protease substrate sites into the linker to N-terminal and C-terminal of most sterically restricted constructs and produce, purify, and characterize thermal stability, binding affinity/kinetics, and kinetics of protease activation. Applicants will also characterize effector function of constructs (with and without activation), establish EC50 on different cell lines, establish serum stability, and perform animal studies to determine PK/PD, biodistribution, and tumor efficacy.

The technology disclosed herein has numerous advantages over current technology. The constructs are highly stable and can be made with high yield (initial expression trials produced ~1-3 g/L transient). Multiple domains are possible (two sdAbs, cytokines sdAb and cytokine, etc). Further, these constructs can be used with CAR T cells. For example, Applicants are designing an anti-CD33/anti-CD123/anti-CD20 CAR T cell.

Applicants' technology as disclosed herein is meeting currently unmet medical needs. Specifically, Applicants' technology is meeting two distinct unmet needs: (1) adverse side effects and (2) manufacturing issues. Adverse side effects remain one of the most significant issues with all therapeutics, especially with checkpoint inhibitors, BiTEs, and CAR T cells. These are further exasperated when combined (Nivo/Ipi combo produces grade irAEs—54-64%). The technology disclosed herein seeks to reduce/eliminate these. Manufacturing of bispecific molecules at clinical scale has severely limited the introduction of these potent therapeutics into the clinic. Applicants' preliminary data indicates this issue will be solved. To the best of Applicants' knowledge, the technology disclosed herein is an entirely new approach to create Tumor-activated, bispecifics biologics.

Example 3: Novel Bispecific T-Cell Engagers (Bites) and Site-Specific Activation of Switchblade Mabs Bispecifics mAbs are known. Historical examples include BiTEs targeting two antigens simultaneously (e.g., Her2/Her3), BiTEs sequestering multiple ligands (e.g. TNF-a/IL17A), BiTEs effecting transport (e.g., transferrin arm to cross blood-brain-barrier), and Bispecific T cell engagers (one arm to CD3/CD16 of T cells or NK cells and the other arm to tumor target e.g., CD19). 47 CD3/NK cell engagers are in clinical trials. Blinatumomab (Blincyto®) is a successful example with significantly longer overall survival among adult patients with relapsed or refractory B-cell precursor and approved since 2014.

Figure 17:
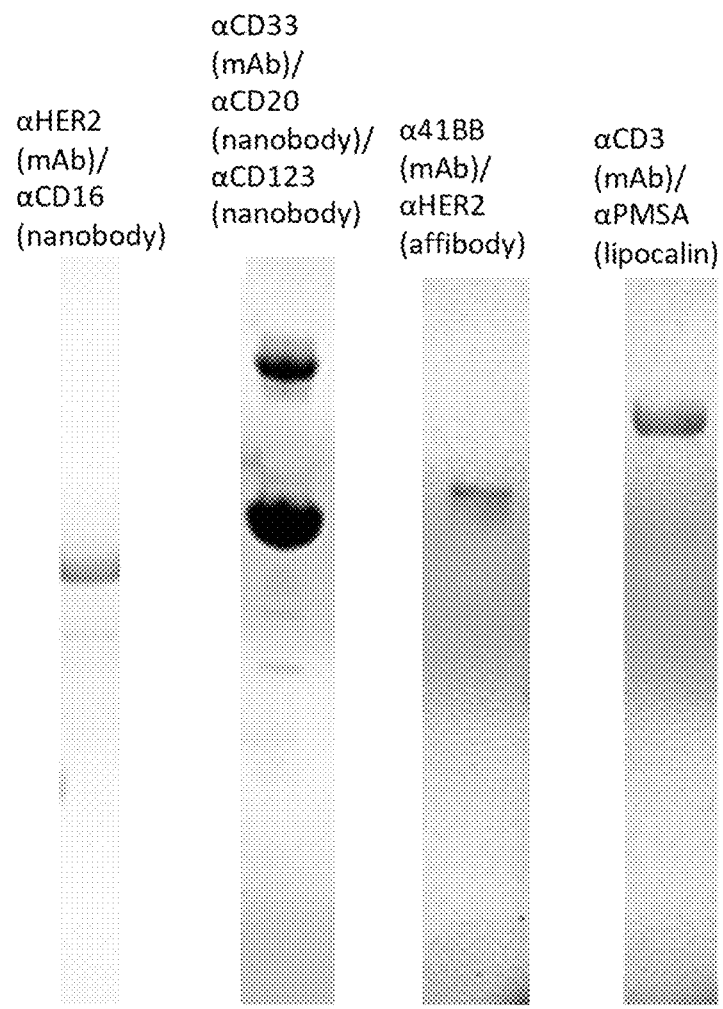
FIG. 17. Representative constructs were run on an SDS-PAGE gel after size exclusion. The major band in each lane corresponds to the expected mass. From left to right the exemplary embodiments of peptides provided herein are: anti-HER2 Fab (second ligand binding domain) bound to anti-CD16 nanobody (first ligand binding domain); anti-CD33 Fab (second ligand binding domain) bound to anti-CD20 nanobody (first ligand binding domain) and anti-CD123 nanobody (third ligand binding domain); anti-4-1BB Fab (second ligand binding domain) bound to an anti-HER2 affibody (first ligand binding domain); and anti-CD3 Fab (second ligand binding domain) bound to an anti-PSMA (lipocalin) (first ligand binding domain).
Figure 18:
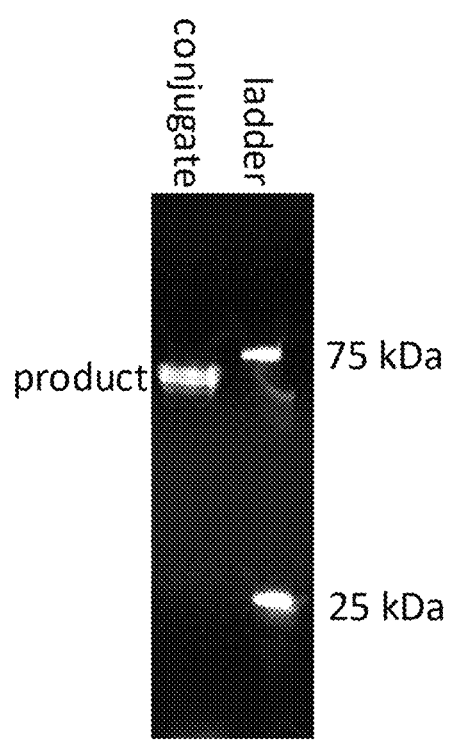
FIG. 18. In vitro evidence of binding of trispecific bionic. See also FIG. 12B which shows the binding efficiency of this trispecific bionic. It was tested whether two nanbodies (first ligand binding domains) could be added between the light and heavy Fab chains (first and second protein dimerizing domain). The 175C meditope version was used to be able to add functionality using the meditope technology. Here, a cysteine meditope bearing fluorescein was added the trispecific bionic. The conjugated molecule separated using a non-reducing SDS-PAGE gel and then imaged using the fluorescent signal from the fluorescein. The fluorescent band is at the expected mass for the product. Non-conjugated fluorescein would run off the gel.
Figure 19:
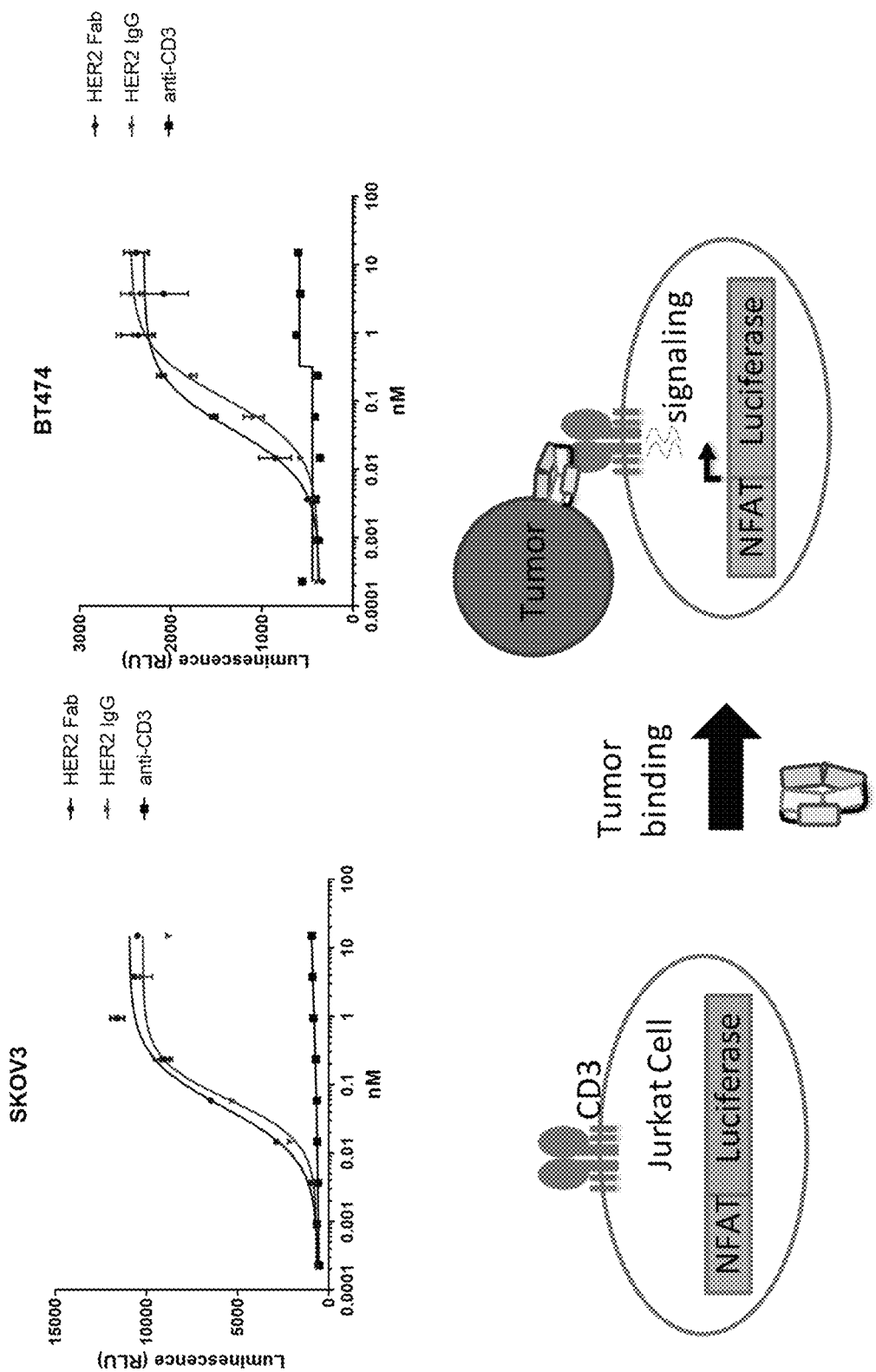
FIG. 19. αHER2 Nanobody inserted to anti-CD3 IgG or Fab is active using our in vitro T cell activation assay. This is a similar assay as shown in FIG. 16. Two different Her2 presenting cells. The activity is not affected by the format. The Fab is monovalent to antigen binding to both CD3 and Her2. The IgG format is tetravalent, where two sites bind to Her2 and two sites to bind to CD3.
Figure 20:
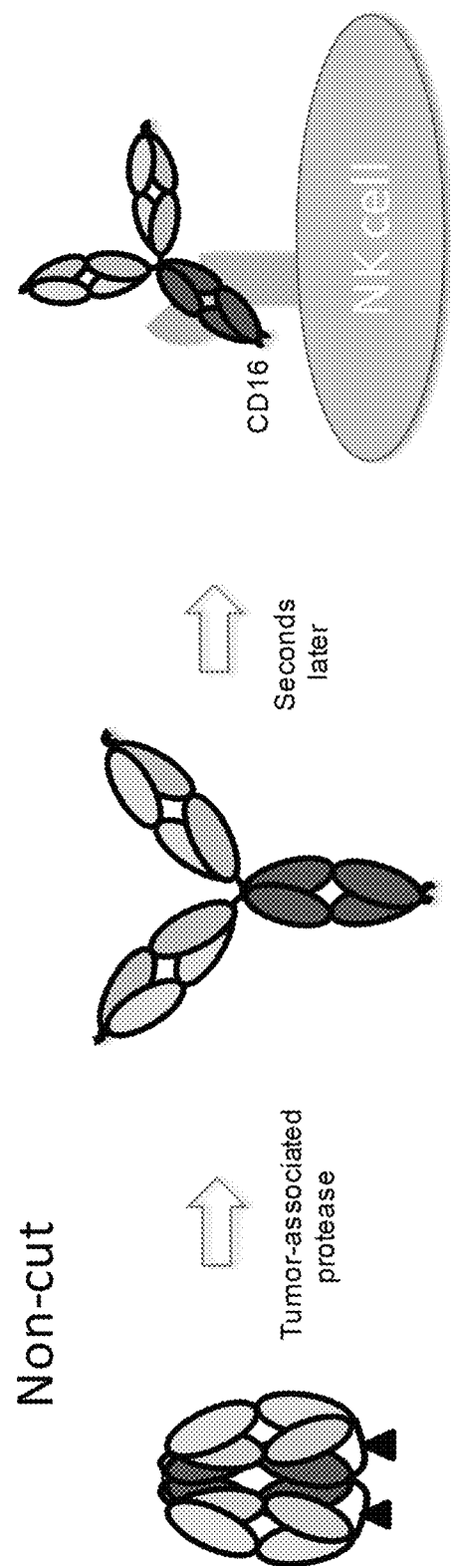
FIG. 20. The figure shows the mechanism of action for the Fc switchblade (exemplary embodiment of the peptide provided herein) and the steric occlusion of the first and second ligand binding domain prior to cleavage of the first or second chemical linker.

Traditional bispecific mAb generation is inefficient (FIG. 4). The novel BiTEs created by Applicants include e.g., a Fab and a nanobody domain and are available in multiple configurations (FIG. 17). Applicants' BiTEs recognize T- or NK cells via their Fab domains and tumor cells by binding to tumor-specific antigens via their nanobody domains, which are readily available against many tumor targets. T/NK cell proximity to tumor cells then initiates tumor cell killing.

Figure 3:
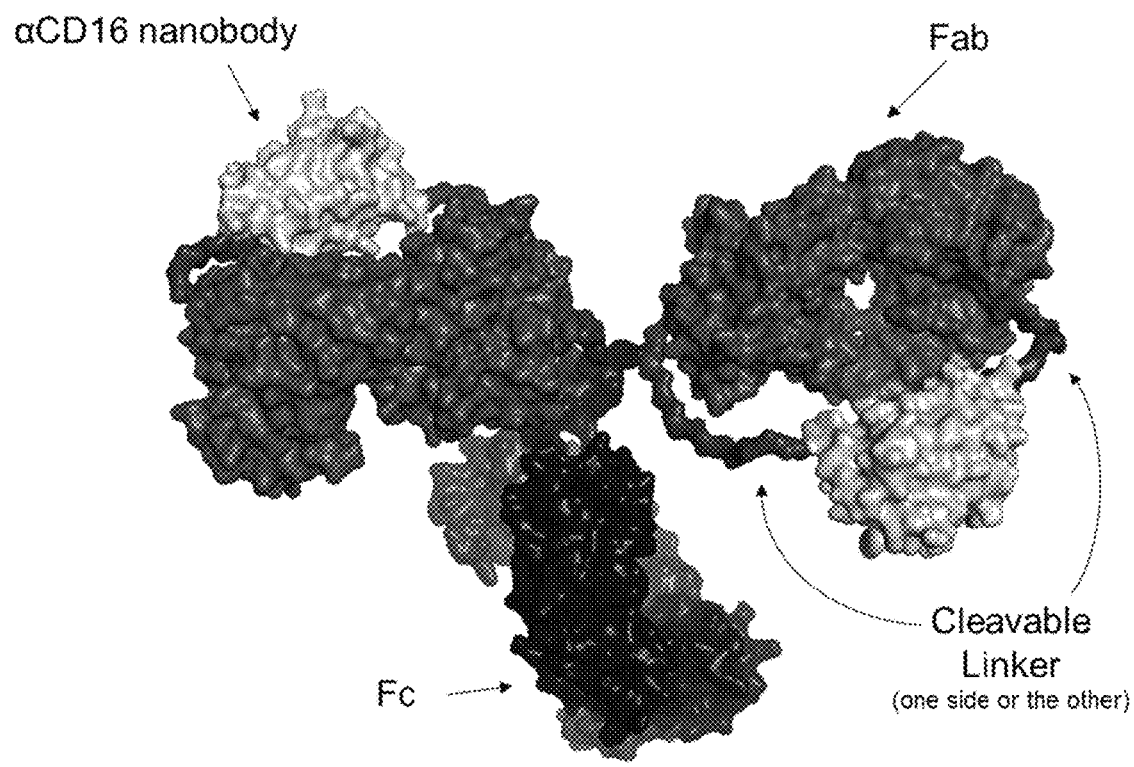
FIG. 3. Structure of an exemplary peptide provided herein also referred to as molecular switchblade.

Applicants have created a new class of bispecifics (FIG. 5). Through appropriate linkers the nanobody can be positioned to sterically prevent the antibody from binding to its target (FIG. 3). Disease-specific proteases can cleave the linker and thus activates the antibody in the correct tissue (reminiscent of a switchblade).

There are numerous advantages to the novel BiTEs and molecular switch blades disclosed herein. Applicants are constructing disease-activated, bi-specific antibodies to improve the safety of immuno-therapeutics and other applications. The mechanism includes a biologic (e.g., a first ligand binding domain) such as a bispecific T-cell engager that is sterically masked as part of a single chain Fab/mAb. A sequence within the chain is cut by a disease-specific protease, thereby removing the steric constraint and activating the molecule (switchblade). A domain between light and heavy chains is novel. These novel peptides are addressing PK/PD issues as well as immune-related adverse events. The peptides provided herein including embodiments thereof further reducing manufacturing issues, are high yield, and are highly stable. They are also applicable to CAR-T cells and other biologics.

Applicants will be performing binding assays and analyze tumor killing in vitro and in vivo.

Example 4

Figure 26:
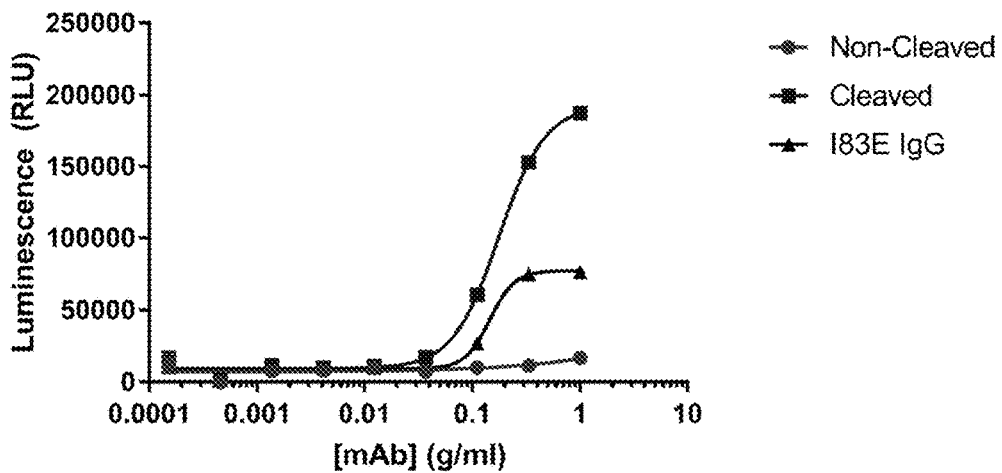
FIG. 26. Only the cleaved switch is able to potentiate an ADCC response.
Figure 27:
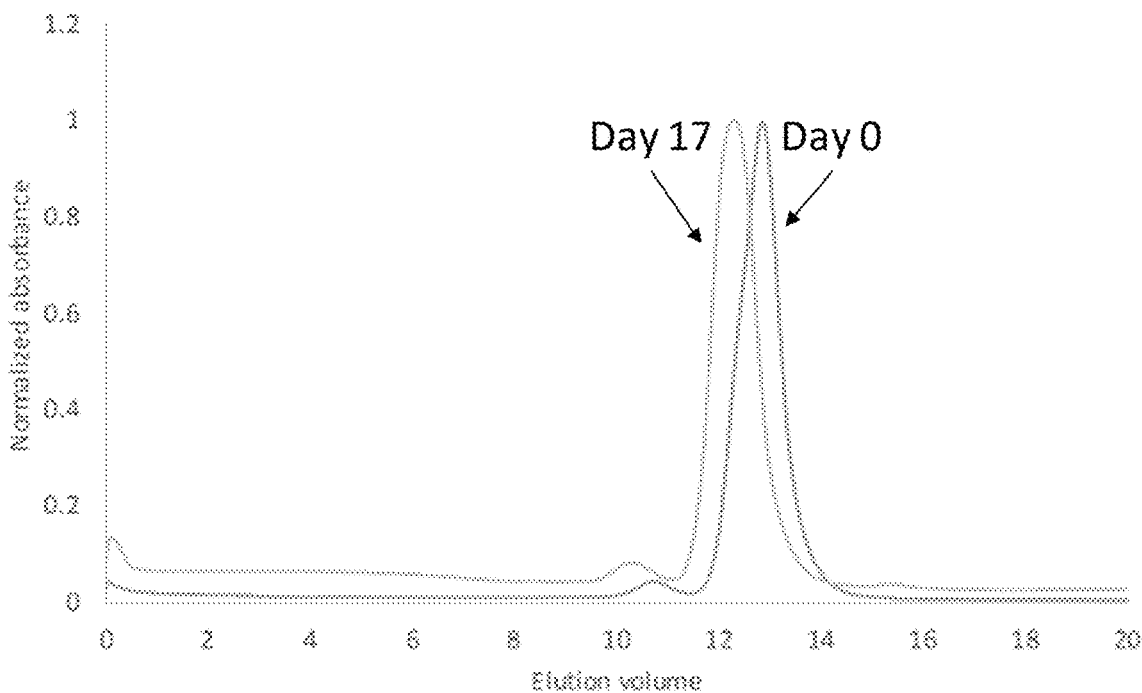
FIG. 27. IgG Switch does not aggregate after 17 days at 37° C. Size exclusion chromatography of the bionic Fc switchblade was conducted immediately after purification and 17 days after purification. The bionic switchblade was stored in PBS at 37° C. over the 17 day period.

The ability to locally active potent molecules at the site of disease is expected to mitigate adverse side effects due to on-target, off-tissue toxicities. In this example, we used the switchblade technology to conditionally activate the Fc domain of an IgG mAb (see FIG. 26). SPR showed that the Fc switchblade binds to the Fc receptor CD16 once cleaved by MMP9 protease. MMP9 cleavage of the Fc switchblade was required for T cell activation in vitro. The compound was stable for 17 days in PBS at 37° C. Collectively, these data are consistent with the 'switchblade' mechanism described herein.

Example 5

The bionic molecules and bionic switchblade molecules can be used for diagnostic purposes as well. In one instance, an imaging agent can be added to the bionic Fab, mAb or variant and used to image disease sites. The bi-specificity (multi-specificity) increases specificity as well as the residence time at the disease site. Likewise, combining disease specific activation of the bionic is expected to enhance specificity. The imaging agents could be used for PET imaging. These include 19F, 64Cu, 177Lu and others. Imaging agents could also include dyes either for optical imaging or for fluorescent guided surgical resection (also known as intraoperative optical imaging). Finally, the bionic and bionic switchblade variants are compatible with pre-targeted imaging methodologies. Any of the methods described in the below publications listed under the reference section are contemplated for the diagnostic use of the peptides provided herein.

REFERENCES

Theranostics Using Antibodies and Antibody-Related Therapeutics. Moek K L, Giesen D, Kok I C, de Groot D J A, Jalving M, Fehrmann R S N, Lub-de Hooge M N, Brouwers A H, de Vries E G E. J Nucl Med. 2017 September; 58(Suppl 2):83S-90S. doi: 10.2967/jnumed.116.186940. Review. PMID: 28864618.

Engineered antibodies for molecular imaging of cancer. Wu A M. Methods. 2014 Jan. 1; 65(1):139-47. doi: 10.1016/j.ymeth.2013.09.015. Epub 2013 Oct. 1. Review. PMID: 24091005

Advantages of patient-derived orthotopic mouse models and genetic reporters for developing fluorescence-guided surgery. Lwin T M, Hoffman R M, Bouvet M. J Surg Oncol. 2018 August; 118(2):253-264. doi: 10.1002/jso.25150. Epub 2018 Aug. 6. Review.

Pretargeted Imaging and Therapy. Altai M, Membreno R, Cook B, Tolmachev V, Zeglis B M. J Nucl Med. 2017 October; 58(10):1553-1559. doi: 10.2967/jnumed.117.189944. Epub 2017 Jul. 7. Review. PMID: 28687600

TABLE 2

Exemplified embodiments of the peptides provided herein including linker embodiments.

| SEQ ID NO: | Biologic (peptide embodiments) |
|---|---|
| | Sc tras cd16 nanobody |
| 19 | WT |
| 20 | D |
| 21 | E |
| 22 | 1E |
| 23 | 2E |
| 24 | 3E |
| 25 | 4E |
| 26 | 5E |
| 27 | 6D |
| 28 | 7E |
| 29 | 8E |
| 30 | 9E |
| 31 | 10E |
| 32 | 11E |
| | Other Bionics (peptide embodiments) |
| 33 | sc 41bb zher2 |
| 34 | sc CD33 CD20 nanobody CD123 nanobody |
| 35 | sc CD3 PSMA lipocalin |
| 36 | sc tras zher3 |
| 37 | sc 1050 (CD3) her2 IgG |
| 38 | sc 1050 (CD3) her2 Fab |
| | Switch-Fc constructs (Ig switchblade embodiments, Trastuzumab-based) |
| 39 | Switch_Fc-WT Linker |
| 40 | Switch_Fc-WT Full Sequence |
| 41 | Switch_Fc-ANQLKG Linker |
| 42 | Switch_Fc-ANQLKG Full Sequence |
| 43 | Switch_Fc-DSGGFMLT Linker |
| 44 | Switch_Fc-DSGGFMLT Full Sequence |
| 45 | Switch_Fc-HEQLTV Linker |
| 46 | Switch_Fc-HEQLTV Full Sequence |
| 47 | Switch_Fc-PAPGVYPGP Linker |

TABLE 2-continued

Exemplified embodiments of the peptides provided herein including linker embodiments.

| SEQ ID NO: | Biologic (peptide embodiments) |
|---|---|
| | Switch-Fc constructs (Ig switchblade embodiments, Trastuzumab-based) |
| 48 | Switch_Fc-PAPGVYPGP Full Sequence |
| 49 | Switch_Fc-QSQLKE Linker |
| 50 | Switch_Fc-QSQLKE Full Sequence |
| 51 | Switch_Fc-RAAAVKSP Linker |
| 52 | Switch_Fc-RAAAVKSP Full Sequence |
| 53 | Switch_Fc-TSVLMAAP Linker |
| 54 | Switch_Fc-TSVLMAAP Full Sequence |
| 55 | Switch_Fc-VANLLYE Linker |
| 56 | Switch_Fc-VANLLYE Full Sequence |
| 57 | Switch_Fc-VGNLNF Linker |
| 58 | Switch_Fc-VGNLNF Full Sequence |
| 59 | Switch_Fc-Non-cleavable Linker |
| 60 | Switch_Fc-Non-cleavable Full Sequence |
| 61 | Switch_Fc-WT plus 3 Linker |
| 62 | Switch_Fc-WT plus 3 Full Sequence |
| 63 | Switch_Fc-WT plus 6 Linker |
| 64 | Switch_Fc-WT plus 6 Full Sequence |
| 65 | meditope-enabled Trastuzumab Heavy Chain |
| 66 | meditope-enabled Trastuzumab Light Chain |
| 67 | I83E meditope-enabled Trastuzumab Light Chain |
| 68 | Switch-Fc Scar chain 1 |
| 69 | Switch-FC Scar chain 2 |
| | Switch-Fc constructs (Ganitumab) |
| 70 | Ganitumab (anti-IGF1R) Light Chain |
| 71 | Ganitumab (anti-IGF1R) Heavy Chain |
| 72 | SC-FC Ganitumab-Non-cleavable |
| 73 | SC-FC Ganitumab-VPLSLY |

```
INFORMAL SEQUENCE LISTING

SEQ ID NO: 1 (trastuzumab light chain - protease site -
antiCD16 - linker - trastuzumab heavy chain)
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECGGAGGSTSTSGRSANPRGGEVQLTE
SGGEDVQAGGSLRLSCSASGLTFSSYNMGWFRRAPGKEREFVASITWSGRDTFYADSV
KGRFTISRDNAKNTVYLQMSSLKPEDTATYYCAANPWPVAAPRSGTYWGEGTQVTVA
SGAGASEVQLVESGGGLVQPGGSLRLSCAASGFNIKDTYIHWVRQSPGKGLEWVARIYP
TNGYTRYADSVKGRFTISADTSKNTAYLQMNSLRAEDTAIYYCSRWGGDGFYAMDYW
GQGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSC*

SEQ ID NO: 2 (anti-CD33-LC/anti-CD20/anti-CD123/anti-CD33-HC
Fab loop, polypeptide)
DIQMTQSPSILSASVGDRVTITCRASESVDNYGISFMNWFQQRTNKAPRLLIYAASNQGS
GVPSRFSGSGSGTDFTLTISSLQPDDEADYYCQQSKEVPWTFGAGTKLEIKRTVAAPSVFI
FPPSDEQLKSGTASVVCLLNNFYPREAKVQWKVDNALQSGNSQESVTEQDSKDSTYSLS
STLTLSKADYEKHKVYACEVTHQGLSSPVTKSFNRGEGGGSSGEVQLVESGGGLVQAG
GSLRLSCAASGSIFSGNVMGWYRRQAPGKEREWVAAIASGGSIYYRDSVKGRFTISRDN
AKNTVYLQMNSLKPEDTAVYYCNSHPPTLPYWGLGTQVTVSSGSEVQLVESGGGLVQP
GGSLRLSCTFSGGTFSSYTMGWFRQAPGKEREFVAEVRWGGVTTYSNSLKDRFSISEDS
VKNAVYLQMNSLKPEDTAVYYCAAVRQMYMTVVPDYWGQGTLVTSSGGGSSGEVQ
LVQSGAEVKKPGSSVKVSCKASGYTFTDYNMHWVRQSPGQGLEWIGYIYPYNGGTGY
NQKFKSKATITADESTNTAYMELSSLRSEDTAIYYCARGRPAMDYWGQGTLVTVSSAST
KGPSVFPLAPSSKSTSGGTAALGCLVKDYFPEPVTVSWNSGALTSGVHTFPCVLQSSGLY
SLSSVVTVPSSSLGTQTYICNVNHKPSNTKVDKKVEPKSGDKTHT SEQ ID NO: 3 (anti-CD33-LC/anti-CD20/anti-CD123/anti-CD33-HC
Fab loop DNA)
ATGGACATGAGGGTCCCCGCTCAGCTCCTGGGGCTCCTGCTGCTCTGGCTCCCAGGT
GCCAAATGTGATATCCAGATGACCCAGTCGCCTTCAATCCTGTCGGCATCCGTCGGA
GACAGAGTGACCATCACTTGCCGGGCCAGCGAATCCGTGGATAACTACGGAATTTC
CTTCATGAATTGGTTCCAGCAGCGGACCAACAAGGCCCCGCGCCTGCTGATCTACGC
GGCCAGCAACCAAGGGTCCGGAGTGCCTTCACGGTTCTCCGGCTCCGGGTCCGGCA
CCGACTTCACCCTGACCATTTCCTCCCTGCAACCGGACGACGAAGCCGATTACTACT
GCCAGCAGTCCAAGGAAGTGCCGTGGACCTTCGGAGCGGGAACCAAGCTCGAGATT
AAGCGGACCGTGGCAGCACCCATCAGTGTTTATTTTCCCCCCGTCCGACGAGCAGCTG
AAGTCGGGTACTGCGAGCGTGGTCTGCCTGCTGAACAATTTCTATCCGCGGGAGGCC
AAGGTCCAGTGGAAAGTCGACAACGCCCTCCAGAGCGGAAACTCTCAGGAGAGCGT
GACCGAACAGGACTCCAAGGACAGCACCTACTCGCTGTCCTCCACGCTCACTCTGTC
CAAGGCCGATTACGAGAAGCACAAGGTCTACGCATGCGAAGTGACCCACCAGGGTC
TTTCCTCCCCTGTGACTAAGTCGTTCAATCGCGGGGAGGGAGGGGGATCCTCGGGAG
AAGTGCAGCTTGTGGAGAGCGGCGGAGGATTGGTGCAGGCCGGGGGATCCCTGAGA
CTGTCCTGTGCCGCGAGCGGCTCGATCTTCTCCGGAAACGTGATGGGCTGGTACCGG
CGACAGGCACCGGGAAAGGAAAGGGAATGGGTGGCCGCCATCGCCTCGGGAGGCA
GCATCTACTACCGGGATTCTGTGAAGGGACGGTTCACCATCTCCCGGGATAACGCCA
AGAACACTGTGTACCTCCAGATGAACTCACTCAAGCCAGAGGATACCGCGGTCTATT
ACTGCAATTCCCACCCTCCCACCCTGCCCTACTGGGGCTTGGTACCCAAGTCACCG
TGTCCTCGGGCTCCGAGGTGCAACTGGTGGAATCTGGGGCGGCCTGGTCCAGCCTG
GCGGCTCCTTGCGGCTGTCATGCACATTCAGCGGTGGAACCTTCAGCTCCTACACCA
TGGGCTGGTTCCGCCAAGCGCCAGGAAAGGAACGGGAGTTCGTGGCCGAAGTGCGC
TGGGGCGGAGTGACTACCTACTCGAACTCCCTGAAAGACCGGTTCAGCATTTCCGAG
```

-continued

INFORMAL SEQUENCE LISTING

```
GACAGCGTGAAGAACGCCGTGTACTTGCAAATGAACTCCCTTAAGCCTGAGGACAC
TGCTGTGTATTACTGTGCCGCCGTGCGCCAGATGTACATGACCGTGGTGCCGGACTA
TTGGGGCCAGGGCACCCTGGTCACCGTCAGCTCGGGCGGCGGAAGCTCCGGAGAGG
TCCAGCTGGTGCAGTCGGGAGCCGAAGTGAAGAAGCCCGGCTCGTCCGTGAAAGTG
TCCTGCAAGGCCTCGGGCTACACCTTTACCGACTACAATATGCATTGGGTCAGACAA
TCACCGGGCCAGGGACTCGAATGGATTGGCTACATCTACCCCTACAACGGTGGAAC
TGGCTACAACCAAAGTTTAAGTCTAAGGCTACTATTACCGCCGACGAAAGCACTA
ACACCGCCTACATGGAACTGAGCTCCCTGAGATCCGAGGACACCGCGATCTACTACT
GTGCCCGCGGGCGCCCTGCGATGGACTACTGGGGCCAAGGCACTCTCGTGACTGTGT
CATCGGCGTCAACTAAGGGACCGAGCGTCTTTCCGCTGGCACCCAGCTCCAAGTCCA
CTTCCGGTGGCACGGCCGCTCTCGGTTGCCTCGTGAAGGATTACTTCCCTGAACCCG
TGACCGTGTCCTGGAACTCCGGAGCGCTGACCTCCGGAGTGCACACTTTCCCCTGCG
TGCTTCAAAGCTCCGGGCTGTACTCCCTGAGCTCGGTCGTGACCGTGCCCTCATCCT
CGTTGGGTACTCAGACGTACATCTGCAACGTGAACCACAAGCCGTCGAATACCAAG
GTCGACAAGAAGGTCGAACCCAAATCGGGAGATAAGTAA

SEQ ID NO: 4 (trastuzumab light chain sequence from SEQ ID NO: 1)
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC SEQ ID NO: 5 (protease site sequence from SEQ ID NO: 1)
GGAGGSTSTSGRSANPRGG SEQ ID NO: 6 (antiCD16 sequence from SEQ ID NO: 1)
EVQLTESGGEDVQAGGSLRLSCSASGLTFSSYNMGWFRRAPGKEREFVASITWSGRDTF
YADSVKGRFTISRDNAKNTVYLQMSSLKPEDTATYYCAANPWPVAAPRSGTYWGEGT
QVTV SEQ ID NO: 7 (linker sequence from SEQ ID NO: 1)
ASGAGAS SEQ ID NO: 8 (trastuzumab heavy chain sequence from SEQ ID NO: 1)
EVQLVESGGGLVQPGGSLRLSCAASGFNIKDTYIHWVRQSPGKGLEWVARIYPTNGYTR
YADSVKGRFTISADTSKNTAYLQMNSLRAEDTAIYYCSRWGGDGFYAMDYWGQGTLV
TVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSC SEQ ID NO: 9 (antiCD33-LC sequence from SEQ ID NO: 2)
DIQMTQSPSILSASVGDRVTITCRASESVDNYGISFMNWFQQRTNKAPRLLIYAASNQGS
GVPSRFSGSGSGTDFTLTISSLQPDDEADYYCQQSKEVPWTFGAGTKLEIKRTVAAPSVFI
FPPSDEQLKSGTASVVCLLNNFYPREAKVQWKVDNALQSGNSQESVTEQDSKDSTYSLS
STLTLSKADYEKHKVYACEVTHQGLSSPVTKSFNRGE SEQ ID NO: 10 (first linker sequence from SEQ ID NO: 2)
GGGSSG SEQ ID NO: 11 (anti-CD20 sequence from SEQ ID NO: 2)
EVQLVESGGGLVQAGGSLRLSCAASGSIFSGNVMGWYRRQAPGKEREWVAAIASGGSI
YYRDSVKGRFTISRDNAKNTVYLQMNSLKPEDTAVYYCNSHPPTLPYWGLGTQVTV SEQ ID NO: 12 (second linker sequence from SEQ ID NO: 2)
SSGS SEQ ID NO: 13 (anti-CD123 sequence from SEQ ID NO: 2)
EVQLVESGGGLVQPGGSLRLSCTFSGGTFSSYTMGWFRQAPGKEREFVAEVRWGGVTT
YSNSLKDRFSISEDSVKNAVYLQMNSLKPEDTAVYYCAAVRQMYMTVVPDYWGQGTL
VTVSS SEQ ID NO: 14 (third linker sequence from SEQ ID NO: 2)
GGGSSG SEQ ID NO: 15 (antiCD33-HC sequence from SEQ ID NO: 2)
EVQLVQSGAEVKKPGSSVKVSCKASGYTFTDYNMHWVRQSPGQGLEWIGYIYPYNGG
TGYNQKFKSKATITADESTNTAYMELSSLRSEDTAIYYCARGRPAMDYWGQGTLVTVS
SASTKGPSVFPLAPSSKSTSGGTAALGCLVKDYFPEPVTVSWNSGALTSGVHTFPCVLQS
SGLYSLSSVVTVPSSSLGTQTYICNVNHKPSNTKVDKKVEPKSGDKTHT SEQ ID NO: 16
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
```

FSCSVMHEALHNHYTQKSLSLSPGKGGSGVPLSLYSGGEVQLVESGGGLVQPGGSLRLS
CAASGFNIKDTYIHWVRQSPGKGLEWVARIYPTNGYTRYADSVKGRFTISADTSKNTAY
LQMNSLRAEDTAIYYCSRWGGDGFYAMDYWGQGTLVTVSSASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC

SEQ ID NO: 17 (an Fc dimerizing domain; Fc region)
DKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

SEQ ID NO: 18
GGSGVPLSLYSGG

SEQ ID NO: 19. ScTras cd16 nanobody WT
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECGGAGGSTSTSGRSANPRGGEVQLTE
SGGEDVQAGGSLRLSCSASGLTFSSYNMGWFRRAPGKEREFVASITWSGRDTFYADSV
KGRFTISRDNAKNTVYLQMSSLKPEDTATYYCAANPWPVAAPRSGTYWGEGTQVTVA
SGAGASEVQLVESGGGLVQPGGSLRLSCAASGFNIKDTYIHWVRQSPGKGLEWVARIYP
TNGYTRYADSVKGRFTISADTSKNTAYLQMNSLRAEDTAIYYCSRWGGDGFYAMDYW
GQGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSC SEQ ID NO: 20. ScTras cd16 nanobody D
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECGGAGGSTSTSGRSANPRGGEVQLTE
SGGEDVQAGGSLRLSCSASGLTFSSYNMGWFRRAPGKEREFVASITWSGRDTFYADSV
KGRFTISRDNAKNTVYLQMSSLKPEDTATYYCAANPWPVAAPRSGTYWGEGTQVTVA
ASEVQLVESGGGLVQPGGSLRLSCAASGFNIKDTYIHWVRQSPGKGLEWVARIYPTNGY
TRYADSVKGRFTISADTSKNTAYLQMNSLRAEDTAIYYCSRWGGDGFYAMDYWGQGT
LVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSC SEQ ID NO: 21. ScTras cd16 nanobody E
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECGGAGGSTSTSGRSANPRGGEVQLTE
SGGEDVQAGGSLRLSCSASGLTFSSYNMGWFRRAPGKEREFVASITWSGRDTFYADSV
KGRFTISRDNAKNTVYLQMSSLKPEDTATYYCAANPWPVAAPRSGTYWGEGTQVTVA
SEVQLVESGGGLVQPGGSLRLSCAASGFNIKDTYIHWVRQSPGKGLEWVARTYPTNGYT
RYADSVKGRFTISADTSKNTAYLQMNSLRAEDTAIYYCSRWGGDGFYAMDYWGQGTL
VTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSC SEQ ID NO: 22. ScTras cd16 nanobody 1E
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECGGAGSTSTSGRSANPRGGEVQLTES
GGEDVQAGGSLRLSCSASGLTFSSYNMGWFRRAPGKEREFVASITWSGRDTFYADSVK
GRFTISRDNAKNTVYLQMSSLKPEDTATYYCAANPWPVAAPRSGTYWGEGTQVTVASE
VQLVESGGGLVQPGGSLRLSCAASGFNIKDTYIHWVRQSPGKGLEWVARTYPTNGYTR
YADSVKGRFTISADTSKNTAYLQMNSLRAEDTAIYYCSRWGGDGFYAMDYWGQGTLV
TVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSC SEQ ID NO: 23. ScTras cd16 nanobody 2E
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECGGASTSTSGRSANPRGGEVQLTESG
GEDVQAGGSLRLSCSASGLTFSSYNMGWFRRAPGKEREFVASITWSGRDTFYADSVKG
RFTISRDNAKNTVYLQMSSLKPEDTATYYCAANPWPVAAPRSGTYWGEGTQVTVASEV
QLVESGGGLVQPGGSLRLSCAASGFNIKDTYIHWVRQSPGKGLEWVARIYPTNGYTRY
ADSVKGRFTISADTSKNTAYLQMNSLRAEDTAIYYCSRWGGDGFYAMDYWGQGTLVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSC

INFORMAL SEQUENCE LISTING

SEQ ID NO: 24. ScTras cd16 nanobody 3E
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECGGSTSTSGRSANPRGGEVQLTESGGE
DVQAGGSLRLSCSASGLTFSSYNMGWFRRAPGKEREFVASITWSGRDTFYADSVKGRFT
ISRDNAKNTVYLQMSSLKPEDTATYYCAANPWPVAAPRSGTYWGEGTQVTVASEVQL
VESGGGLVQPGGSLRLSCAASGFNIKDTYIHWVRQSPGKGLEWVARIYPTNGYTRYADS
VKGRFTISADTSKNTAYLQMNSLRAEDTAIYYCSRWGGDGFYAMDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSC SEQ ID NO: 25. ScTras cd16 nanobody 4E
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECGSTSTSGRSANPRGGEVQLTESGGED
VQAGGSLRLSCSASGLTFSSYNMGWFRRAPGKEREFVASITWSGRDTFYADSVKGRFTI
SRDNAKNTVYLQMSSLKPEDTATYYCAANPWPVAAPRSGTYWGEGTQVTVASEVQLV
ESGGGLVQPGGSLRLSCAASGFNIKDTYIHWVRQSPGKGLEWVARTYPTNGYTRYADSV
KGRFTISADTSKNTAYLQMNSLRAEDTAIYYCSRWGGDGFYAMDYWGQGTLVTVSSA
STKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSC SEQ ID NO: 26. ScTras cd16 nanobody 5E
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECSTSTSGRSANPRGGEVQLTESGGEDV
QAGGSLRLSCSASGLTFSSYNMGWFRRAPGKEREFVASITWSGRDTFYADSVKGRFTIS
RDNAKNTVYLQMSSLKPEDTATYYCAANPWPVAAPRSGTYWGEGTQVTVASEVQLVE
SGGGLVQPGGSLRLSCAASGFNIKDTYIHWVRQSPGKGLEWVARIYPTNGYTRYADSV
KGRFTISADTSKNTAYLQMNSLRAEDTAIYYCSRWGGDGFYAMDYWGQGTLVTVSSA
STKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSC SEQ ID NO: 27. ScTras cd16 nanobody 6D
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC
STSTGRSANPRGGEVQLTESGGEDVQAGGSLRLSCSASGLTFSSYNMGWFRRAPGKERE
FVASITWSGRDTFYADSVKGRFTISRDNAKNTVYLQMSSLKPEDTATYYCAANPWPVA
APRSGTYWGEGTQVTVAASEVQLVESGGGLVQPGGSLRLSCAASGFNIKDTYIHWVRQ
SPGKGLEWVARTYPTNGYTRYADSVKGRFTISADTSKNTAYLQMNSLRAEDTAIYYCSR
WGGDGFYAMDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVD
KKVEPKSC SEQ ID NO: 28. ScTras cd16 nanobody 7E
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECSTSGRSANPRGGEVQLTESGGEDVQ
AGGSLRLSCSASGLTFSSYNMGWFRRAPGKEREFVASITWSGRDTFYADSVKGRFTISR
DNAKNTVYLQMSSLKPEDTATYYCAANPWPVAAPRSGTYWGEGTQVTVASEVQLVES
GGGLVQPGGSLRLSCAASGFNIKDTYIHWVRQSPGKGLEWVARTYPTNGYTRYADSVK
GRFTISADTSKNTAYLQMNSLRAEDTAIYYCSRWGGDGFYAMDYWGQGTLVTVSSAST
KGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSC SEQ ID NO: 29. ScTras cd16 nanobody 8E
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECSTGRSANPRGGEVQLTESGGEDVQA
GGSLRLSCSASGLTFSSYNMGWFRRAPGKEREFVASITWSGRDTFYADSVKGRFTISRD
NAKNTVYLQMSSLKPEDTATYYCAANPWPVAAPRSGTYWGEGTQVTVASEVQLVESG
GGLVQPGGSLRLSCAASGFNIKDTYIHWVRQSPGKGLEWVARIYPTNGYTRYADSVKG
RFTISADTSKNTAYLQMNSLRAEDTAIYYCSRWGGDGFYAMDYWGQGTLVTVSSASTK
GPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSC SEQ ID NO: 30. ScTras cd16 nanobody 9E
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD

INFORMAL SEQUENCE LISTING

EQLKSGTASVVCLLNNFYPREAKVQWKVDNALQSGNSQESVTEQDSKDSTYSLSSTLTL
SKADYEKHKVYACEVTHQGLSSPVTKSFNRGECGRSANPRGGEVQLTESGGEDVQAG
GSLRLSCSASGLTFSSYNMGWFRRAPGKEREFVASITWSGRDTFYADSVKGRFTISRDN
AKNTVYLQMSSLKPEDTATYYCAANPWPVAAPRSGTYWGEGTQVTVASEVQLVESGG
GLVQPGGSLRLSCAASGFNIKDTYIHWVRQSPGKGLEWVARIYPTNGYTRYADSVKGR
FTISADTSKNTAYLQMNSLRAEDTAIYYCSRWGGDGFYAMDYWGQGTLVTVSSASTK
GPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSC

SEQ ID NO: 31. ScTras cd16 nanobody 10E
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECGRSANPRGGEVQLTESGGEDVQAGG
SLRLSCSASGLTFSSYNMGWFRRAPGKEREFVASITWSGRDTFYADSVKGRFTISRDNA
KNTVYLQMSSLKPEDTATYYCAANPWPVAAPRSGTYWGEGTQVTVASEVQLVESGGG
LVQPGGSLRLSCAASGFNIKDTYIHWVRQSPGKGLEWVARIYPTNGYTRYADSVKGRFT
ISADTSKNTAYLQMNSLRAEDTAIYYCSRWGGDGFYAMDYWGQGTLVTVSSASTKGPS
VFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSC SEQ ID NO: 32. ScTras cd16 nanobody 11E
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECGRSANPRGGEVQLTESGGEDVQAGGS
LRLSCSASGLTFSSYNMGWFRRAPGKEREFVASITWSGRDTFYADSVKGRFTISRDNAK
NTVYLQMSSLKPEDTATYYCAANPWPVAAPRSGTYWGEGTQVTVASEVQLVESGGGL
VQPGGSLRLSCAASGFNIKDTYIHWVRQSPGKGLEWVARIYPTNGYTRYADSVKGRFTI
SADTSKNTAYLQMNSLRAEDTAIYYCSRWGGDGFYAMDYWGQGTLVTVSSASTKGPS
VFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSC SEQ ID NO: 33. Sc41BB zher2
EVQLVQSGAEVKKPGESLRISCKGSGYSFSTYWISWVRQMPGKGLEWMGKIYPGDSYT
NYSPSFQGQVTISADKSISTAYLQWSSLKASDTAMYYCARGYGIFDYWGQGTLVTVSSA
STKGPSVFPLAPCSRSTSESTAALGCLVKDYFPEPVTVSWNSGALTSGVHTFPAVLQSSG
LYSLSSVVTVPSSNFGTQTYTCNVDHKPSNTKVDKTVERKSCGGSAASSPSGGGPASVD
NKFNKEMRNAYWEIALLPNLNNQQKRAFIRSLYDDPSQSANLLAEAKKLNDAQAPKGG
PASGAPSSASYELTQPPSVSVSPGQTASITCSGDNIGDQYAHWYQQKPGQSPVLVIYQDK
NRPSGIPERFSGSNSGNTATLTISGTQAMDEADYYCATYTGFGSLAVFGGGTKLTVLGQ
PKAAPSVTLFPPSSEELQANKATLVCLISDFYPGAVTVAWKADSSPVKAGVETTTPSKQS
NNKYAASSYLSLTPEQWKSHRSYSCQVTHEGSTVEKTVAPTECS SEQ ID NO: 34. scCD33 CD20 nanobody CD123 nanobody
DIQMTQSPSILSASVGDRVTITCRASESVDNYGISFMNWFQQRTNKAPRLLIYAASNQGS
GVPSRFSGSGSGTDFTLTISSLQPDDEADYYCQQSKEVPWTFGAGTKLEIKRTVAAPSVFI
FPPSDEQLKSGTASVVCLLNNFYPREAKVQWKVDNALQSGNSQESVTEQDSKDSTYSLS
STLTLSKADYEKHKVYACEVTHQGLSSPVTKSFNRGECGGGSGEVQLVESGGGLVQA
GGSLRLSCAASGSIFSGNVMGWYRRQAPGKEREWVAAIASGGSIYYRDSVKGRFTISRD
NAKNTVYLQMNSLKPEDTAVYYCNSHPPTLPYWGLGTQVTVSSGSEVQLVESGGGLV
QPGGSLRLSCTFSGGTFSSYTMGWFRQAPGKEREFVAEVRWGGVTTYSNSLKDRFSISE
DSVKNAVYLQMNSLKPEDTAVYYCAAVRQMYMTVVPDYVVGQGTLVTVSSGGGSSGE
VQLVQSGAEVKKPGSSVKVSCKASGYTFTDYNMHWVRQSPGQGLEWIGYIYPYNGGT
GYNQKFKSKATITADESTNTAYMELSSLRSEDTAIYYCARGRPAMDYWGQGTLVTVSS
ASTKGPSVFPLAPSSKSTSGGTAALGCLVKDYFPEPVTVSWNSGALTSGVHTFPCVLQSS
GLYSLSSVVTVPSSSLGTQTYICNVNHKPSNTKVDKKVEPKSGDK SEQ ID NO: 35. sc CD3 PSMA lipocalin
CRHDQPMLCGGSGVPLSLYSGGDIQMTQSPILLSASVGDRVTITCSASSSVSYMNVVYQQ
RTNGSPRLLIYDTSKLASGVPSRFSGSRSGTDFTLTISSLQPEDEADYYCQQWSSNPFTFG
AGTKVEIKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGECAGP
SSGASGSQDSTSDLIPAPPLSKVPLQQNFQDNQFHGKWYVVGLAGNVILREDKDPYKMS
ATIYELKEDKSYNVTNVRFYLNKCYYTIATFVPGSRPGEFTLGTIKSGPGKTSGLVRVVS
TNYSQHAMVFFKEVQQNREWFIITLYGRTKELTSKLKENFIRFSKSLGLPENHIVPPVPID
QCIDGSSAGPGEVQLVESGGGLVQPGGSLRLSCAASGYTFTRYTMHWVRQSPGKGLEW
VAYINPSRGYTNYADSVKGRFTISADKSKNTAYLQMNSLRAEDTAIYYCSRYYDDHYC
LDYWGQGTLVTVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDKKVEPKSCDK
THT SEQ ID NO: 36. sc tras zher3
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECGGAGGSTSTSSSSGSSVVDNKFNKER

INFORMAL SEQUENCE LISTING

YLAYYEIWQLPNLNRTQKAAFIGSLQDDPSQSANLLAEAKKLNDAQAPKGGSGRLIEDI
CLPRWGCLWEDDSSGSSGSSGSSGEVQLVESGGGLVQPGGSLRLSCAASGFNIKDTYIH
WVRQSPGKGLEWVARIYPTNGYTRYADSVKGRFTISADTSKNTAYLQMNSLRAEDTAI
YYCSRWGGDGFYAMDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPS
NTKVDKKVEPKSC

SEQ ID NO: 37. sc 1050 (CD3) her2 IgG
DIQMTQSPILLSASVGDRVTITCRASQSISSYLNWYQQRTNGSPRLLIYAASSLQSGVPSR
FSGSGSGTDFTLTISSLQPEDADYYCQQSYSTPPITFGAGTRLEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGECSSASGSTSTSGSSASSSGGQVQLQESG
GGSVQAGGSLKLTCAASGYIFNSCGMGWYRQSPGRERELVSRISGDGDTWHKESVKGR
FTISQDNVKKTLYLQMNSLKPEDTAVYFCAVCYNLETYWGQGTQVTVSSASGAGASEV
QLVESGGGLVQPGRSLRLSCAASGFTFADYTMHWVRQAPGKGLEWVSDISWNSGSIAY
ADSVKGRFTISRDNAKNSLYLQMNSLRTEDTAIYYCAKDSRGYGHYKYLGLDVWGQG
TTVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK SEQ ID NO: 38. sc 1050 (CD3) her2 Fab
DIQMTQSPILLSASVGDRVTITCRASQSISSYLNWYQQRTNGSPRLLIYAASSLQSGVPSR
FSGSGSGTDFTLTISSLQPEDADYYCQQSYSTPPITFGAGTRLEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGECSSASGSTSTSGSSASSSGGQVQLQESG
GGSVQAGGSLKLTCAASGYIFNSCGMGWYRQSPGRERELVSRISGDGDTWHKESVKGR
FTISQDNVKKTLYLQMNSLKPEDTAVYFCAVCYNLETYWGQGTQVTVSSASGAGASEV
QLVESGGGLVQPGRSLRLSCAASGFTFADYTMHWVRQAPGKGLEWVSDISWNSGSIAY
ADSVKGRFTISRDNAKNSLYLQMNSLRTEDTAIYYCAKDSRGYGHYKYLGLDVWGQG
TTVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH SEQ ID NO: 39. Switch_Fc-WT linker
GGSGVPLSLYSGG SEQ ID NO: 40. Switch_Fc-WT full sequence
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGGSGVPLSLYSGGEVQLVESGGGLVQPGGSLRLS
CAASGFNIKDTYIHWVRQSPGKGLEWVARIYPTNGYTRYADSVKGRFTISADTSKNTAY
LQMNSLRAEDTAIYYCSRWGGDGFYAMDYWGQGTLVTVSSASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC SEQ ID NO: 41. Switch_Fc-ANQLKG linker
GSGSANQLKGS SG SEQ ID NO: 42. Switch_Fc-ANQLKG full sequence
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGSGSANQLKGSSGEVQLVESGGGLVQPGGSLRLS
CAASGFNIKDTYIHWVRQSPGKGLEWVARIYPTNGYTRYADSVKGRFTISADTSKNTAY
LQMNSLRAEDTAIYYCSRWGGDGFYAMDYWGQGTLVTVSSASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC SEQ ID NO: 43. Switch_Fc-DSGGFMLT linker
GSSDSGGFMLTSG SEQ ID NO: 44. Switch_Fc-DSGGFMLT full sequence
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGSSDSGGFMLTSGEVQLVESGGGLVQPGGSLRLS
CAASGFNIKDTYIHWVRQSPGKGLEWVARIYPTNGYTRYADSVKGRFTISADTSKNTAY
LQMNSLRAEDTAIYYCSRWGGDGFYAMDYWGQGTLVTVSSASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC SEQ ID NO: 45. Switch_Fc-HEQLTV linker
GSGSHEQLTVSSG SEQ ID NO: 46. Switch_Fc-HEQLTV full sequence
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGSGSHEQLTVSSGEVQLVESGGGLVQPGGSLRLS
CAASGFNIKDTYIHWVRQSPGKGLEWVARIYPTNGYTRYADSVKGRFTISADTSKNTAY
LQMNSLRAEDTAIYYCSRWGGDGFYAMDYWGQGTLVTVSSASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC SEQ ID NO: 47. Switch_Fc-PAPGVYPGP linker
GSPAPGVYPGPSG SEQ ID NO: 48. Switch_Fc-PAPGVYPGP full sequence
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGSPAPGVYPGPSGEVQLVESGGGLVQPGGSLRLS
CAASGFNIKDTYIHWVRQSPGKGLEWVARIYPTNGYTRYADSVKGRFTISADTSKNTAY
LQMNSLRAEDTAIYYCSRWGGDGFYAMDYWGQGTLVTVSSASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC SEQ ID NO: 49. Switch_Fc-QSQLKE linker
GSGSQSQLKESSG SEQ ID NO: 50. Switch_Fc-QSQLKE full sequence
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGSGSQSQLKESSGEVQLVESGGGLVQPGGSLRLS
CAASGFNIKDTYIHWVRQSPGKGLEWVARIYPTNGYTRYADSVKGRFTISADTSKNTAY
LQMNSLRAEDTAIYYCSRWGGDGFYAMDYWGQGTLVTVSSASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC SEQ ID NO: 51. Switch_Fc-RAAAVKSP linker
GSSRAAAVKSPSG SEQ ID NO: 52. Switch_Fc-RAAAVKSP full sequence
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGSSRAAAVKSPSGEVQLVESGGGLVQPGGSLRLS
CAASGFNIKDTYIHWVRQSPGKGLEWVARIYPTNGYTRYADSVKGRFTISADTSKNTAY
LQMNSLRAEDTAIYYCSRWGGDGFYAMDYWGQGTLVTVSSASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC

INFORMAL SEQUENCE LISTING

SEQ ID NO: 53. Switch_Fc-TSVLMAAP linker
GSSTSVLMAAPSG

SEQ ID NO: 54. Switch_Fc-TSVLMAAP full sequence
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGSSTSVLMAAPSGEVQLVESGGGLVQPGGSLRLS
CAASGFNIKDTYIHWVRQSPGKGLEWVARIYPTNGYTRYADSVKGRFTISADTSKNTAY
LQMNSLRAEDTAIYYCSRWGGDGFYAMDYWGQGTLVTVSSASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC SEQ ID NO: 55. Switch_Fc-VANLLYE linker
GSSVANLLYESSG SEQ ID NO: 56. Switch_Fc-VANLLYE full sequence
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGSSVANLLYESSGEVQLVESGGGLVQPGGSLRLS
CAASGFNIKDTYIHWVRQSPGKGLEWVARIYPTNGYTRYADSVKGRFTISADTSKNTAY
LQMNSLRAEDTAIYYCSRWGGDGFYAMDYWGQGTLVTVSSASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC SEQ ID NO: 57. Switch_Fc-VGNLNF linker
GSGSVGNLNFSSG SEQ ID NO: 58. Switch_Fc-VGNLNF full sequence
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGSGSVGNLNFSSGEVQLVESGGGLVQPGGSLRLS
CAASGFNIKDTYIHWVRQSPGKGLEWVARIYPTNGYTRYADSVKGRFTISADTSKNTAY
LQMNSLRAEDTAIYYCSRWGGDGFYAMDYWGQGTLVTVSSASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC SEQ ID NO: 59. Switch_Fc-Non-cleavable linker
GGSGGSSGSSSGG SEQ ID NO: 60. Switch_Fc-Non-cleavable full sequence
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGGSGGSSGSSSGGEVQLVESGGGLVQPGGSLRLS
CAASGFNIKDTYIHWVRQSPGKGLEWVARIYPTNGYTRYADSVKGRFTISADTSKNTAY
LQMNSLRAEDTAIYYCSRWGGDGFYAMDYWGQGTLVTVSSASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC SEQ ID NO: 61. Switch_Fc-WT plus 3 linker
GGSGVPLSLYSGGSSG SEQ ID NO: 62. Switch_Fc-WT plus 3 full sequence
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS -continued

INFORMAL SEQUENCE LISTING

VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGGSGVPLSLYSGGSSGEVQLVESGGGLVQPGGSL
RLSCAASGFNIKDTYIHWVRQSPGKGLEWVARTYPTNGYTRYADSVKGRFTISADTSKN
TAYLQMNSLRAEDTAIYYCSRWGGDGFYAMDYWGQGTLVTVSSASTKGPSVFPLAPSS
KSTSGGTAALGCLVKDYFPEPVTVSWNSGALTSGVHTFPAVLQSSGLYSLSSVVTVPSSS
LGTQTYICNVNHKPSNTKVDKKVEPKSC

SEQ ID NO: 63. Switch_Fc-WT plus 6 linker
GGSGVPLSLYSGGSSGSSG

SEQ ID NO: 64. Switch_Fc-WT plus 6 full sequence
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGGSGVPLSLYSGGSSGSSGEVQLVESGGGLVQPG
GSLRLSCAASGFNIKDTYIHWVRQSPGKGLEWVARIYPTNGYTRYADSVKGRFTISADT
SKNTAYLQMNSLRAEDTAIYYCSRWGGDGFYAMDYWGQGTLVTVSSASTKGPSVFPL
APSSKSTSGGTAALGCLVKDYFPEPVTVSWNSGALTSGVHTFPAVLQSSGLYSLSSVVT
VPSSSLGTQTYICNVNHKPSNTKVDKKVEPKSC SEQ ID NO: 65. meditope-enabled Trastuzumab Heavy Chain
EVQLVESGGGLVQPGGSLRLSCAASGFNIKDTYIHWVRQSPGKGLEWVARIYPTNGYTR
YADSVKGRFTISADTSKNTAYLQMNSLRAEDTAIYYCSRWGGDGFYAMDYWGQGTLV
TVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPE
LLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPGK SEQ ID NO: 66. meditope-enabled Trastuzumab Light Chain
DIQMTQSPILLSASVGDRVTITCRASQDVNTAVAWYQQRTNGSPRLLIYSASFLYSGVPS
RFSGSRSGTDFTLTIS SLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC SEQ ID NO: 67. I83E meditope-enabled Trastuzumab Light Chain
DIQMTQSPILLSASVGDRVTITCRASQDVNTAVAWYQQRTNGSPRLLIYSASFLYSGVPS
RFSGSRSGTDFTLTISSLQPEDEADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC SEQ ID NO: 68. Switch-Fc Scar chain 1
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGGSGVPLS SEQ ID NO: 69. Switch-FC Scar chain 2
LYSGGEVQLVESGGGLVQPGGSLRLSCAASGFNIKDTYIHWVRQSPGKGLEWVARIYPT
NGYTRYADSVKGRFTISADTSKNTAYLQMNSLRAEDTAIYYCSRWGGDGFYAMDYWG
QGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSC SEQ ID NO: 70. Ganitumab (anti-IGF1R) Light Chain
DVVMTQSPLSLPVTPGEPASISCRSSQSLLHSNGYNYLDWYLQKPGQSPQLLIYLGSNRA
SGVPDRFSGSGSGTDFTLKISRVEAEDVGVYYCMQGTHWPLTFGQGTKVEIKRTVAAPS
VFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 71. Ganitumab (anti-IGF1R) Heavy Chain
QVQLQESGPGLVKPSGTLSLTCAVSGGSISSSNWWSWVRQPPGKGLEWIGEIYHSGSTN
YNPSLKSRVTISVDKSKNQFSLKLSSVTAADTAVYYCARWTGRTDAFDIWGQGTMVTV
SSASTKGPSVFPLAPSSKSTSGGTAALGCLVKDYFPEPVTVSWNSGALTSGVHTFPCVLQ
SSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGSFFLYSKLTV

```
DKSRWQQGNVFSCSVMHEALHNHYTQKSLSLSPGK

SEQ ID NO: 72. SC-FC Ganitumab-non-cleavable
DVVMTQSPLSLPVTPGEPASISCRSSQSLLHSNGYNYLDWYLQKPGQSPQLLIYLGSNRA
SGVPDRFSGSGSGTDFTLKISRVEAEDVGVYYCMQGTHWPLTFGQGTKVEIKRTVAAPS
VFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGECDKTHTCPPCPAPELLGGPD
VFLFPPKPKDTLMISRTPEVTCVVVDVSHEDPEVKFNWYVDGVEVHNAKTKPREEQYN
STYRVVSVLTVLHQDWLNGKEYKCKVSNKALPAPEEKTISKAKGQPREPQVYTLPPSRD
ELTKNQVSLTCLVKGFYPSDIAVEWESNGQPENNYKTTPPVLDSDGSFFLYSKLTVDKS
RWQQGNVFSCSVMHEALHNHYTQKSLSLSPGKGGSGGSSGSSSGGQVQLQESGPGLVK
PSGTLSLTCAVSGGSISSSNWWSWVRQPPGKGLEWIGEIYHSGSTNYNPSLKSRVTISVD
KSKNQFSLKLSSVTAADTAVYYCARWTGRTDAFDIWGQGTMVTVSSASTKGPSVFPLA
PSSKSTSGGTAALGCLVKDYFPEPVTVSWNSGALTSGVHTFPAVLQSSGLYSLSSVVTVP
SSSLGTQTYICNVNHKPSNTKVDKKVEPKSC SEQ ID NO: 73. SC-FC Ganitumab-VPLSLY
DVVMTQSPLSLPVTPGEPASISCRSSQSLLHSNGYNYLDWYLQKPGQSPQLLIYLGSNRA
SGVPDRFSGSGSGTDFTLKISRVEAEDVGVYYCMQGTHWPLTFGQGTKVEIKRTVAAPS
VFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGECDKTHTCPPCPAPELLGGPD
VFLFPPKPKDTLMISRTPEVTCVVVDVSHEDPEVKFNWYVDGVEVHNAKTKPREEQYN
STYRVVSVLTVLHQDWLNGKEYKCKVSNKALPAPEEKTISKAKGQPREPQVYTLPPSRD
ELTKNQVSLTCLVKGFYPSDIAVEWESNGQPENNYKTTPPVLDSDGSFFLYSKLTVDKS
RWQQGNVFSCSVMHEALHNHYTQKSLSLSPGKGGSGVPLSLYSGGQVQLQESGPGLVK
PSGTLSLTCAVSGGSISSSNWWSWVRQPPGKGLEWIGEIYHSGSTNYNPSLKSRVTISVD
KSKNQFSLKLSSVTAADTAVYYCARWTGRTDAFDIWGQGTMVTVSSASTKGPSVFPLA
PSSKSTSGGTAALGCLVKDYFPEPVTVSWNSGALTSGVHTFPAVLQSSGLYSLSSVVTVP
SSSLGTQTYICNVNHKPSNTKVDKKVEPKSC SEQ ID NO: 74 Trastuzumab IgG switchblade
DIQMTQSPILLSASVGDRVTITCRASQDVNTAVAWYQQRTNGSPRLLIYSASFLYSGVPS
RFSGSRSGTDFTLTISSLQPEDIADYYCQQHYTTPPTFGAGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPELLGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNV
FSCSVMHEALHNHYTQKSLSLSPGKGGSGVPLSLYSGGEVQLVESGGGLVQPGGSLRLS
CAASGFNIKDTYIHWVRQSPGKGLEWVARIYPTNGYTRYADSVKGRFTISADTSKNTAY
LQMNSLRAEDTAIYYCSRWGGDGFYAMDYWGQGTLVTVSSASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC
```

EMBODIMENTS

Embodiment 1. A peptide comprising: (i) a first protein dimerizing domain bound to a first ligand binding domain through a first chemical linker; and (ii) a second protein dimerizing domain bound to said first ligand binding domain through a second chemical linker; wherein said first protein dimerizing domain is capable of non-covalently binding to said second protein dimerizing domain to form a second ligand binding domain.

Embodiment 2. The peptide of embodiment 1, wherein said first ligand binding domain is different from said second ligand binding domain.

Embodiment 3. The peptide of embodiment 1 or 2, wherein said peptide further comprises a covalent bond connecting said first protein dimerizing domain and said second protein dimerizing domain.

Embodiment 4. The peptide of one of embodiments 1-3, wherein said first protein dimerizing domain is bound to said second protein dimerizing domain.

Embodiment 5. The peptide of one of embodiments 1-4, wherein said first chemical linker is bound to the N-terminus of said first ligand binding domain and said second chemical linker is bound to the C-terminus of said first ligand binding domain.

Embodiment 6. The peptide of one of embodiments 1-4, wherein said first chemical linker is bound to the C-terminus of said first ligand binding domain and said second chemical linker is bound to the N-terminus of said first ligand binding domain.

Embodiment 7. The peptide of one of embodiments 1-6, wherein said first protein dimerizing domain comprises a variable light chain domain.

Embodiment 8. The peptide of one of embodiments 1-7, wherein said first protein dimerizing domain comprises a constant light chain domain.

Embodiment 9. The peptide of embodiment 8, wherein said variable light chain domain is bound to said first ligand binding domain through said constant light chain domain.

Embodiment 10. The peptide of one of embodiments 1-9, wherein said first protein dimerizing domain is an antibody light chain.

Embodiment 11. The peptide of one of embodiments 1-10, wherein said second protein dimerizing domain comprises a variable heavy chain domain.

Embodiment 12. The peptide of one of embodiments 1-11, wherein said second protein dimerizing domain comprises a constant heavy chain domain.

Embodiment 13. The peptide of 12, wherein said constant heavy chain domain is bound to said first ligand binding domain through said variable heavy chain domain.

Embodiment 14. The peptide of one of embodiments 1-13, wherein said second protein dimerizing domain is an antibody heavy chain.

Embodiment 15. The peptide of one of embodiments 1-6, wherein said first protein dimerizing domain comprises a variable heavy chain domain.

Embodiment 16. The peptide of one of embodiments 1-6 or 15, wherein said first protein dimerizing domain comprises a constant heavy chain domain.

Embodiment 17. The peptide of embodiment 16, wherein said variable heavy chain domain is bound to said first ligand binding domain through said constant heavy chain domain.

Embodiment 18. The peptide of one of embodiments 1-6 or 15-17, wherein said second protein dimerizing domain comprises a variable light chain domain.

Embodiment 19. The peptide of one of embodiments 1-6 or 15-18, wherein said second protein dimerizing domain comprises a constant light chain domain.

Embodiment 20. The peptide of embodiment 19, wherein said constant light chain domain is bound to said first ligand binding domain through said variable light chain domain.

Embodiment 21. The peptide of one of embodiments 1-6 or 15-20, wherein said second protein dimerizing domain is an antibody light chain.

Embodiment 22. The peptide of one of embodiments 1-21, wherein said second ligand binding domain is a Fab domain.

Embodiment 23. The peptide of one of embodiments 1-22, wherein said second protein dimerizing domain is bound to an Fc domain through a third chemical linker.

Embodiment 24. The peptide of one of embodiments 1-23, wherein said first chemical linker is a peptidyl linker.

Embodiment 25. The peptide of one of embodiments 1-24, wherein said first chemical linker further comprises a third ligand binding domain.

Embodiment 26. The peptide of embodiment 25, wherein said third ligand binding domain is bound to said first ligand binding domain through a fourth chemical linker.

Embodiment 27. The peptide of one of embodiments 1-26, wherein said second chemical linker is a peptidyl linker.

Embodiment 28. The peptide of one of embodiments 1-27, wherein said second chemical linker further comprises a fourth ligand binding domain.

Embodiment 29. The peptide of embodiment 28, wherein said fourth ligand binding domain is bound to said first ligand binding domain through a fifth chemical linker.

Embodiment 30. The peptide of one of embodiments 1-29, wherein said first ligand binding domain, said second ligand binding domain, said third ligand binding domain and said fourth ligand binding domain are independently different or the same.

Embodiment 31. The peptide of one of embodiments 1-30, wherein said first ligand binding domain, said second ligand binding domain, said third ligand binding domain and said fourth ligand binding domain are independently a tumor binding domain, a T-cell activating domain or an interleukin domain.

Embodiment 32. The peptide of one of embodiments 1-31, wherein said first ligand binding domain, said second ligand binding domain, said third ligand binding domain and said fourth ligand binding domain independently comprise a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain or a 41BB binding domain.

Embodiment 33. The peptide of one of embodiments 1-32, wherein said first ligand binding domain, said third ligand binding domain and said fourth ligand binding domain independently comprise a single domain antibody domain.

Embodiment 34. The peptide of one of embodiments 1-33, wherein said first chemical linker and said second chemical linker are independently a covalent linker or a non-covalent linker.

Embodiment 35. The peptide of one of embodiments 1-34, wherein said first chemical linker and said second chemical linker are independently a cleavable peptide linker.

Embodiment 36. The peptide of one of embodiments 1-35, wherein said first chemical linker and said second chemical linker are independently an enzymatically cleavable linker.

Embodiment 37. The peptide of one of embodiments 1-36, wherein said first chemical linker and said second chemical linker are independently a protease cleavable linker.

Embodiment 38. The peptide of one of embodiments 1-37, wherein said first chemical linker and said second chemical linker independently have a length of about 0 to about 15 amino acid residues.

Embodiment 39. The peptide of one of embodiments 1-38, wherein said first ligand binding domain is a first Fc dimerzing domain.

Embodiment 40. The peptide of embodiment 39, wherein said first Fc dimerzing domain is bound to a second peptide comprising: (i) a third protein dimerizing domain bound to a second Fc dimerzing domain through a fourth chemical linker; and (ii) a fourth protein dimerizing domain bound to said second Fc dimerzing domain through a fifth chemical linker; wherein said third protein dimerizing domain is capable of non-covalently binding to said fourth protein dimerizing domain to form a third ligand binding domain; and wherein said first Fc dimerzing domain and said second Fc dimerzing domain are covalently bound together thereby binding said first peptide to said second peptide.

Embodiment 41. The peptide of embodiment 40, wherein said first protein dimerizing domain and said third protein dimerizing domain are independently an antibody light chain or an antibody heavy chain.

Embodiment 42. The peptide of embodiment 40, wherein said first protein dimerizing domain and said third protein dimerizing domain are independently an antibody light chain.

Embodiment 43. The peptide of any one of embodiments 40-42, wherein said second protein dimerizing domain and said fourth protein dimerizing domain are independently an antibody heavy chain or an antibody light chain.

Embodiment 44. The peptide of any one of embodiments 40-42, wherein said second protein dimerizing domain and said fourth protein dimerizing domain are independently an antibody heavy chain.

Embodiment 45. The peptide of any one of embodiments 40-44, wherein said fourth chemical linker is bound to the N-terminus of said second Fc dimerzing domain and said fifth chemical linker is bound to the C-terminus of said Fc dimerzing domain.

Embodiment 46. The peptide of any one of embodiments 40-45, wherein said first linker and said fourth linker are independently a bond.

Embodiment 47. The peptide of any one of embodiments 40-46, wherein said second linker and said fifth linker are independently a cleavable linker.

Embodiment 48. The peptide of any one of embodiments 40-47, wherein said second linker and said fifth linker independently comprise the sequence of SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61 or SEQ ID NO:63.

Embodiment 49. The peptide of any one of embodiments 40-47, wherein said second linker and said fifth linker independently are the sequence of SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61 or SEQ ID NO:63.

Embodiment 50. The peptide of any one of embodiments 40-49, wherein said first peptide and said second peptide are chemically different or the same.

Embodiment 51. The peptide of any one of embodiments 39-50, wherein said first Fc dimerzing domain comprises a first CH2 domain and a first CH3 domain.

Embodiment 52. The peptide of any one of embodiments 40-51, wherein said second Fc dimerzing domain comprises a second CH2 domain and a second CH3 domain.

Embodiment 53. The peptide of embodiment 51 or 52, wherein said first CH2 domain is covalently bound to said second CH2 domain.

Embodiment 54. The peptide of any one of embodiments 51-53, wherein said first CH2 domain is covalently bound to said second CH2 domain through a disulfide linkage.

Embodiment 55. The peptide of any one of embodiments 51-54, wherein said first CH3 domain is non-covalently bound to said second CH3 domain.

Embodiment 56. The peptide of any one of embodiments 39-54, wherein said first Fc dimerzing domain and said second Fc dimerzing domain form an antibody Fc region.

Embodiment 57. The peptide of any one of embodiments 40-56, wherein said second ligand binding domain and said third ligand binding domain are independently a Fab or an scFv.

Embodiment 58. The peptide of any one of embodiments 40-57, wherein said second ligand binding domain and said third ligand binding domain are a Fab.

Embodiment 59. The peptide of any one of embodiments 40-58, wherein said second ligand binding domain and said third ligand binding domain are an anti-HER2 Fab.

Embodiment 60. A peptide comprising: (i) a first protein dimerizing domain bound to a first multivalent ligand binding domain through a first chemical linker; and (ii) a second protein dimerizing domain bound to said first multivalent ligand binding domain through a second chemical linker; wherein said first protein dimerizing domain is capable of non-covalently binding to said second protein dimerizing domain to form a second ligand binding domain.

Embodiment 61. The peptide of embodiment 60, wherein said first ligand binding domain is different from said second ligand binding domain.

Embodiment 62. The peptide of embodiment 60 or 61, wherein said first multivalent ligand binding domain comprises two or more ligand binding domains connected through one or more chemical linkers.

Embodiment 63. The peptide of one of embodiments 60-64, wherein said two or more ligand binding domains bind different ligands.

Embodiment 64. The peptide of one of embodiments 60-63, wherein said first multivalent ligand binding domain comprises a third ligand binding domain and a fourth ligand binding domain.

Embodiment 65. The peptide of embodiment 64, wherein said third ligand binding domain is bound to said fourth ligand binding domain through a third chemical linker.

Embodiment 66. The peptide of one of embodiments 60-65, wherein said third ligand binding domain is bound to said first protein dimerizing domain through said first chemical linker and said fourth ligand binding domain is bound to said second protein dimerzing domain through said second chemical linker.

Embodiment 67. The peptide of one of embodiments 60-66, wherein said first multivalent ligand binding domain, said second ligand binding domain, said third ligand binding domain and said fourth ligand binding domain are independently different or the same.

Embodiment 68. The peptide of one of embodiments 60-67, wherein said first multivalent ligand binding domain, said second ligand binding domain, said third ligand binding domain and said fourth ligand binding domain are independently a tumor binding domain, a T-cell activating domain or an interleukin domain.

Embodiment 69. The peptide of one of embodiments 60-68, wherein said first multivalent ligand binding domain, said second ligand binding domain, said third ligand binding domain and said fourth ligand binding domain independently comprise a CD3 binding domain, a CD16 binding domain, an Her2 binding domain, a CD123 binding domain, a CD20 binding domain, a tumor-associated glycoprotein 72 (TAG72) binding domain, a carcinoembryonic antigen (CEA) binding domain, a CD252 binding domain, a glucocorticoid-induced tumor necrosis factor receptor (GITR) binding domain or a 41BB binding domain.

Embodiment 70. The peptide of one of embodiments 1-69, wherein said peptide forms part of a chimeric antigen receptor.

Embodiment 71. The peptide of one of embodiments 1-70, wherein said peptide forms part of a T cell.

Embodiment 72. An isolated nucleic acid encoding a peptide of one of embodiments 1-69.

Embodiment 73. An expression vector comprising the nucleic acid of embodiment 72.

Embodiment 74. The expression vector of embodiment 73, wherein said expression vector is a viral vector.

Embodiment 75. The expression vector of embodiment 74, wherein said virus is a lentivirus or onco-retrovirus.

Embodiment 76. A T lymphocyte comprising the expression vector of one of embodiments 73 to 75.

Embodiment 77. A method of treating cancer in a subject in need thereof, said method comprising administering to a subject a therapeutically effective amount of a peptide of one of embodiments 1-69, thereby treating cancer in said subject.

Embodiment 78. A pharmaceutical composition comprising a therapeutically effective amount of a peptide of one of embodiments 1-69 and a pharmaceutically acceptable excipient.

What is claimed is:

1. A single-chain peptide comprising:
   (i) a $V_L$-$C_L$ domain bound to a single domain antibody domain through a first peptidyl linker; and
   (ii) a $V_H$-$C_H$ domain bound to said single domain antibody domain through a second peptidyl linker;
   wherein said $V_L$-$C_L$ domain is capable of non-covalently binding to said $V_H$-$C_H$ domain to form a Fab domain;
   wherein said first peptidyl linker or said second peptidyl linker comprise a proteolytic cleavage site; and
   wherein said $V_L$-$C_L$ domain or said $V_H$-$C_H$ domain are bound to the N-terminus said single domain antibody.

2. The single-chain peptide of claim 1, wherein said first peptidyl linker or said second peptidyl linker is a non-cleavable peptide linker.

3. The single-chain peptide of claim 1, wherein said first peptidyl linker comprises a proteolytic cleavage site and said second peptidyl linker is a non-cleavable peptide linker.

4. The single-chain peptide of claim 1, wherein said first peptidyl linker comprises a non-cleavable peptide linker and said second peptidyl linker is a proteolytic cleavage site.

5. The single-chain peptide of claim 1, wherein said first peptidyl linker and said second peptidyl linker comprise a proteolytic cleavage site.

6. A single-chain peptide comprising:
   (i) a $V_L$-$C_L$ domain bound to a single domain antibody domain through a first peptidyl linker; and
   (ii) a $V_H$-$C_H$ domain bound to said single domain antibody domain through a second peptidyl linker;
   wherein said $V_L$-$C_L$ domain is capable of covalently binding to said $V_H$-$C_H$ domain to form a Fab domain;
   wherein said first peptidyl linker or said second peptidyl linker comprise a proteolytic cleavage site; and
   wherein said $V_L$-$C_L$ domain or said $V_H$-$C_H$ domain are bound to the N-terminus said single domain antibody.

7. The single-chain peptide of claim 6, wherein said first peptidyl linker or said second peptidyl linker is a non-cleavable peptide linker.

8. The single-chain peptide of claim 6, wherein said first peptidyl linker comprises a proteolytic cleavage site and said second peptidyl linker is a non-cleavable peptide linker.

9. The single-chain peptide of claim 6, wherein said first peptidyl linker comprises a non-cleavable peptide linker and said second peptidyl linker is a proteolytic cleavage site.

10. The single-chain peptide of claim 6, wherein said first peptidyl linker and said second peptidyl linker comprise a proteolytic cleavage site.

* * * * *